US012716053B2

(12) United States Patent
Ko

(10) Patent No.: US 12,716,053 B2
(45) Date of Patent: Aug. 25, 2026

(54) METHOD FOR DIFFERENTIATING PLURIPOTENT STEM CELLS INTO DESIRED CELL TYPE

(71) Applicant: KEIO UNIVERSITY, Tokyo (JP)

(72) Inventor: Minoru Ko, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 329 days.

(21) Appl. No.: 18/391,763

(22) Filed: Dec. 21, 2023

(65) Prior Publication Data

US 2024/0124836 A1 Apr. 18, 2024

Related U.S. Application Data

(62) Division of application No. 17/065,541, filed on Oct. 8, 2020, now Pat. No. 11,891,621, which is a division of application No. 15/555,559, filed as application No. PCT/JP2016/057420 on Mar. 9, 2016, now Pat. No. 10,836,997.

(30) Foreign Application Priority Data

Mar. 9, 2015 (JP) ................................ 2015-046318

(51) Int. Cl.

| | |
|---|---|
| ***C12N 5/0793*** | (2010.01) |
| ***C12N 5/07*** | (2010.01) |
| ***C12N 5/071*** | (2010.01) |
| ***C12N 5/0735*** | (2010.01) |
| ***C12N 5/0797*** | (2010.01) |
| ***C12N 5/16*** | (2006.01) |

(52) U.S. Cl.

CPC ............. *C12N 5/0619* (2013.01); *C12N 5/06* (2013.01); *C12N 5/0606* (2013.01); *C12N 5/0623* (2013.01); *C12N 5/067* (2013.01); *C12N 5/0672* (2013.01); *C12N 5/16* (2013.01); *C12N 2501/60* (2013.01); *C12N 2501/65* (2013.01); *C12N 2506/02* (2013.01); *C12N 2506/45* (2013.01); *C12N 2510/00* (2013.01)

(58) Field of Classification Search

CPC .............. C12N 5/0647; C12N 2506/02; C12N 2506/45

See application file for complete search history.

(56) References Cited

U.S. PATENT DOCUMENTS

| | | | |
|---|---|---|---|
| 8,497,124 | B2 | 7/2013 | Angel et al. |
| 10,836,997 | B2 | 11/2020 | Ko |
| 2002/0090603 | A1 | 7/2002 | Lipton et al. |
| 2005/0221487 | A1 | 10/2005 | Zon et al. |
| 2009/0285788 | A1 | 11/2009 | Wilson et al. |
| 2011/0280844 | A1 | 11/2011 | Yu et al. |
| 2014/0037600 | A1 | 2/2014 | Yu et al. |
| 2014/0273211 | A1 | 9/2014 | Slukvin et al. |
| 2016/0046905 | A1 | 2/2016 | Inoue et al. |
| 2018/0127714 | A1 | 5/2018 | Ko |
| 2021/0024887 | A1 | 1/2021 | Ko |

FOREIGN PATENT DOCUMENTS

| | | | |
|---|---|---|---|
| EP | 2495320 | A1 | 9/2012 |
| JP | 2004-016109 | A | 1/2004 |
| JP | 2006061106 | A | 3/2006 |
| JP | 2013-252081 | A | 12/2013 |
| WO | 2013025963 | A2 | 2/2013 |
| WO | 2013163171 | A1 | 10/2013 |

OTHER PUBLICATIONS

Bukrinsky et al (Blood 113(9):2038-2046, 2009). (Year: 2009).*
Kucia et al (Blood 120(21): abstract 4745 2012). (Year: 2012).*
Lynch et al (Nature 480:383-420, 2011). (Year: 2011).*
Tymms and Kola (Molecular Reproduction a n d Development 39:208-214, 1994). (Year: 1994).*
Wang et al. (Animal Genetics 39(3):207-216, 2008, abstract only). (Year: 2008).*
International Search Report and Written Opinion (English Translation) issued in corresponding International Patent Application No. PCT/JP2016/057420 dated Jun. 7, 2016 (14 pages).
Berg et al., "Beta-Catenin Regulates Mesenchymal Progenitor Cell Differentiation During Hepatogenesis," Journal of Surgical Research, 2010, vol. 164, pp. 276-285.
Kim et al., "Overexpression of SOX9 in mouse embryonic stem cells directs the immediate chondrogenic commitment," Experimental and Molecular Medicine, 2005, vol. 37, No. 4, pp. 261-268.
Kim et al., "OVOL2 is a critical regulator of ER71/ETV2 in generating FLK1+, hematopoietic, and endothelial cells from embryonic stem cells," Blood, 2014, vol. 124, No. 19, pp. 2948-2952.
Nakatake et al., "Hito Es-saibo ni Okeru Tensa Inshi Yudo no Morateki Kaiseki," Regenerative Medicine, 2015, vol. 14, Suppl., p. 231 (English translation) (1 page).
Yamamizu et al., "Tensha Inshi o Mochiita Tanosei Kansaibo kara Nin'i Saibo eno Bunka Yudoho no Kaihatsu," Experimental Medicine, 2015, vol. 33, No. 2 (special extra issue), pp. 87-94 (English translation ) (1 page).

(Continued)

*Primary Examiner* — Marcia S Noble

(74) *Attorney, Agent, or Firm* — Kilyk & Bowersox, P.L.L.C.

(57) ABSTRACT

Provided is a method of differentiating a pluripotent stem cell of mammalian origin into a desired cell type by predicting the direction of cell differentiation to be caused by induction of expression of a transcription factor. A human gene expression correlation matrix using human cells has been newly created, and further, it has been confirmed that human pluripotent stem cells can be differentiated into a desired cell type by introducing, into the human pluripotent stem cells, a transcription factor cocktail selected from the matrix.

6 Claims, 21 Drawing Sheets

Specification includes a Sequence Listing.

(56) References Cited

OTHER PUBLICATIONS

Funakoshi Corporation, "Human Umbilical Cord Blood-Derived CD34-Positive Progenitor Cells", PromoCell GmbH dated Jul. 15, 2008, retrieved on Dec. 23, 2022, Internet <https://urldefense.proofpoint.com/v2/url?u=https-3A_web.archive.org_web_20150424011224_https-3A_www.funakoshi.co.jp_contents_3105&d=DwlCaQ&c=euGZstcaTDllvimEN8b7jXrwquOf-v5A_CdpgnVfiiMM&r=UETUGAX4dSIeOEhMy403an7n4fPSuSA1chfMaRQ4l&m=axHBScyn4oNw9OviT2A1_7jlfs8.

* cited by examiner

Fig. 3A
Fetal_brain
Pituitary
Cerebellum_Peduncles
Cerebellum
Whole_Brain
Brain_Thalamus
Hypothalamus
Prefrontal_Cortex
Occipital_Lobe
Brain_Amygdala
Cauda_tenucleus
Cingulate_Cortex
Medulla_Oblongata
Globus_pallidus
Subthalamic_nucleus
Parietal_Lobe
Temporal_Lobe
Pons
Olfactory_Bulb
Spinal_cord
Heart
Skeletal_Muscle_Psoas
Tongue
Skin
Dorsal_root_ganglion
Appendix
Superior_Cervical_Ganglion
Atrioventricular_node
Trigeminal_Ganglion
Ciliary_ganglion
Uterus_Corpus
Ovary
Adrenal_Cortex
Adrenal_gland
Placenta
Lung
Fetal_lung
Trachea
Kidney
Liver
Prostate
Thyroid
Fetal_Thyroid
Cultured_adipocyte
Uterus
Fetal_liver
Salivary_gland
Islet_Cell
Pancreas
Cardiac_Myocytes
Smooth_Muscle
Colorectal_Adenocarc
Bronchial_epithelial_cells(HBEC)
Whole_blood(JJV)
Myeloid(BM_CD33)
Monocytes(PB_CD14)
Lymphnode
Tonsil
Bone_marrow
Thymus
Natural_Killer_Cells(PB_CD56)
Dendritic_Cells(PB_BDCA4)
B_Cells(PB_CD19)
T_Cells(PB_CD8)
T_Cells(PB_CD4)
Early_Erythroid(BM_CD71)
Lymphoma_Raji
B_lymphoblasts(721)
Endothelial_cells(BM_CD105)
Bone_marrow(CD34)
Leukemia_chronic_myelogenous(k562)
Lymphoma_burkitts_Daudi
Leukemia_promyelocytic(hl60)
Leukemia_lymphoblastic(molt4)
Testis
Testis_Leydig_Cell
Testis_Germ_Cell
Testis_Seminiferous_Tubule
Testis_Interstitial

Fig. 4A

| TFs | Fetal_brain | TFs | Pituitary | TFs | Cerebellum_Peduncles | TFs | Cerebellum |
|---|---|---|---|---|---|---|---|
| SOX11 | 21.729 | SOX17 | 14.895 | NEUROG2 | 19.085 | NEUROG2 | 19.904 |
| NEUROG2 | 19.583 | SOX2 | 14.85 | NEUROG3 | 17.022 | NEUROG3 | 17.909 |
| MXI1 | 17.649 | SOX7 | 11.833 | TAL1 | 14.781 | TAL1 | 16.187 |
| NEUROG1 | 16.646 | CDX2 | 11.432 | NEUROG1 | 14.589 | BLZF1 | 15.351 |
| NEUROG3 | 16.373 | ASCL1 | 11.298 | BLZF1 | 14.02 | NEUROG1 | 15.189 |
| SOX7 | 15.858 | SOX15 | 11.126 | NEUROD1 | 12.881 | NEUROD1 | 13.451 |
| HOXA2 | 12.893 | NANOG | 10.975 | ZNF280B | 12.265 | NRF1 | 12.821 |
| POU3F2 | 11.579 | HOXA2 | 10.397 | NRF1 | 11.373 | MXI1 | 12.373 |
| NEUROD2 | 11.576 | NR2F2 | 10.029 | HOXA2 | 11.285 | ZNF280B | 12.096 |
| RARA | 11.498 | FOXA1 | 9.965 | ASCL1 | 10.879 | HOXA2 | 12.02 |
| PDX1 | 11.398 | DLX4 | 9.548 | NEUROD6 | 10.823 | FOXD1 | 11.767 |
| FLI1 | 10.829 | SOX10 | 9.232 | MXI1 | 10.818 | PITX2 | 11.679 |
| FOXS1 | 10.618 | FOXA2 | 9.153 | FOXD1 | 10.739 | NEUROD6 | 11.397 |
| MEIS2 | 10.57 | EED | 8.988 | KLF15 | 10.21 | ASCL1 | 11.379 |
| SOX17 | 10.521 | E2F6 | 8.978 | PITX2 | 9.945 | SNAPC1 | 11.219 |
| HOXC6 | 10.503 | PDX1 | 8.924 | NEUROD2 | 9.802 | NEUROD2 | 10.785 |
| NEUROD1 | 10.469 | PHOX2B | 8.842 | SNAPC1 | 9.53 | KLF15 | 10.678 |
| EED | 10.284 | DLX3 | 8.68 | YBX1 | 9.083 | NFIB | 10.553 |
| NR2F1 | 10.242 | HOXD3 | 8.544 | PRDM1 | 9.04 | YBX1 | 10.019 |
| NEUROD6 | 10.217 | FOXS1 | 7.846 | SMAD7 | 9.016 | CREB1 | 10.308 |
| LHX1 | 10.173 | ZBED4 | 7.651 | ATOH1 | 8.635 | PRDM1 | 9.881 |
| GLIS2 | 10.04 | NR2F1 | 7.568 | SOX7 | 8.439 | ATOH1 | 9.805 |
| YBX1 | 9.891 | SOX11 | 7.492 | MAB21L3 | 8.403 | MAX | 9.262 |
| HOXA3 | 9.842 | POU3F2 | 7.481 | POU4F1 | 8.341 | TCF4 | 9.218 |
| RHOXF2 | 9.752 | MYOD1 | 7.387 | TCF4 | 8.17 | SMAD7 | 8.839 |
| ZBED4 | 9.478 | NEUROG1 | 7.192 | CREB1 | 8.123 | TCF12 | 8.819 |
| SOX2 | 9.123 | DLX2 | 7.039 | MAX | 8.119 | ERG | 8.729 |
| ETV5 | 8.947 | FOXC1 | 6.675 | FOXS1 | 8.105 | GLIS2 | 8.536 |
| POU4F1 | 8.74 | TCF12 | 6.645 | SOX11 | 7.849 | SOX11 | 8.487 |
| HOXD3 | 8.671 | RARA | 6.318 | TCF12 | 7.801 | UGP2 | 8.398 |

Fig. 4B

| TFs | Whole_Brain | TFs | Brain_Thalamus | TFs | Hypothalamus | TFs | Prefrontal_Cortex |
|---|---|---|---|---|---|---|---|
| NEUROG2 | 18.951 | NEUROG2 | 13.928 | SOX7 | 14.169 | NEUROG2 | 18.808 |
| NEUROG3 | 14.357 | HOXA2 | 11.582 | NEUROG2 | 13.727 | NEUROG3 | 15.987 |
| NEUROG1 | 13.249 | NEUROG3 | 11.269 | SOX17 | 13.71 | MXI1 | 15.838 |
| NRF1 | 13.235 | NEUROG1 | 10.96 | SOX2 | 12.873 | SOX7 | 15.827 |
| MXI1 | 11.308 | SOX7 | 10.798 | HOXA2 | 12.571 | YBX1 | 15.382 |
| ZNF280B | 10.786 | GLIS2 | 10.274 | SOX10 | 12.217 | NEUROG1 | 15.103 |
| HOXA2 | 10.708 | SOX17 | 10.221 | NEUROG1 | 11.988 | SOX17 | 14.148 |
| PITX2 | 10.339 | NRF1 | 10.178 | GLIS2 | 10.84 | HOXA2 | 13.887 |
| KLF15 | 10.23 | KLF15 | 8.7 | NEUROG3 | 10.81 | SOX11 | 13.445 |
| NEUROD1 | 9.774 | ASCL1 | 8.428 | MXI1 | 9.867 | SOX2 | 12.44 |
| ASCL1 | 9.327 | SOX10 | 8.402 | SOX11 | 9.426 | ASCL1 | 11.753 |
| GLIS2 | 9.078 | POU4F1 | 8.053 | ASCL1 | 9.258 | SOX10 | 11.703 |
| POU4F1 | 8.881 | FOXD1 | 7.933 | SOX9 | 9.069 | PDX1 | 11.463 |
| SOX7 | 8.715 | MXI1 | 7.898 | PDX1 | 8.782 | POU4F1 | 10.886 |
| NFIB | 8.581 | SOX2 | 7.862 | NRF1 | 8.574 | NRF1 | 10.362 |
| FOXD1 | 8.544 | PITX2 | 7.828 | SOX15 | 8.155 | GLIS2 | 10.056 |
| BLZF1 | 8.078 | SREBF2 | 7.403 | NR2F1 | 7.998 | HOXD3 | 10.05 |
| POU2AF1 | 8.061 | RNF2 | 7.172 | E2F8 | 7.98 | NEUROD1 | 9.983 |
| TAL1 | 8.02 | PPARGC1A | 6.942 | NANOG | 7.922 | KLF15 | 9.959 |
| ZNF281 | 7.982 | TCF12 | 6.808 | CDX2 | 7.798 | TAL1 | 9.804 |
| PPARGC1A | 7.913 | E2F8 | 6.757 | POU4F1 | 7.772 | FOXS1 | 9.434 |
| NEUROD6 | 7.705 | REPIN1 | 6.718 | FOXS1 | 7.694 | CREB1 | 9.319 |
| HOXD3 | 7.674 | SOX11 | 6.576 | HOXD3 | 7.651 | CDX2 | 9.093 |
| CREB1 | 7.509 | NEUROD6 | 6.519 | RARA | 7.462 | NEUROD2 | 9.08 |
| ESPLAM | 7.44 | YY1 | 6.391 | TCF12 | 7.42 | PRDM1 | 8.977 |
| MAX | 7.433 | PDX1 | 6.373 | SREBF2 | 7.416 | BLZF1 | 8.855 |
| SNAPC1 | 7.393 | NEUROD1 | 6.14 | NR2F2 | 6.848 | NANOG | 8.426 |
| TCF4 | 7.319 | NFIB | 6.121 | POU3F2 | 6.594 | NFIB | 8.397 |
| VDR | 7.239 | ZNF281 | 6.108 | HOXA3 | 6.591 | PITX2 | 8.348 |

Fig. 4C

| TFs | Occipital_Lobe | TFs | Brain_Amygdala | TFs | Cauda_tenucleus | TFs | Cingulate_Cortex |
|---|---|---|---|---|---|---|---|
| NEUROG2 | 18.185 | NEUROG2 | 18.309 | NEUROG2 | 14.487 | NEUROG2 | 16.932 |
| NEUROG1 | 15.894 | NEUROG1 | 15.287 | HOXA2 | 13.472 | NEUROG3 | 16.429 |
| HOXA2 | 15.034 | SOX7 | 15.048 | SOX7 | 12.208 | NEUROG1 | 15.039 |
| SOX7 | 14.956 | NEUROG3 | 14.906 | NEUROG3 | 11.931 | HOXA2 | 14.039 |
| NEUROG3 | 14.598 | HOXA2 | 14.872 | SOX17 | 11.872 | SOX7 | 12.772 |
| MXI1 | 14.202 | MXI1 | 14.287 | NRF1 | 11.863 | NRF1 | 12.326 |
| SOX17 | 14.088 | SOX17 | 14.147 | NEUROG1 | 11.843 | YBX1 | 12.011 |
| SOX2 | 12.206 | SOX2 | 12.931 | MXI1 | 11.43 | TAL1 | 11.815 |
| SOX11 | 11.833 | SOX10 | 12.081 | SOX2 | 11.13 | ASCL1 | 11.727 |
| PDX1 | 11.498 | PDX1 | 11.901 | GLIS2 | 10.877 | MXI1 | 11.564 |
| SOX10 | 11.353 | GLIS2 | 11.645 | SOX10 | 10.45 | SOX17 | 11.4 |
| GLIS2 | 10.343 | NRF1 | 11.424 | ASCL1 | 9.568 | KLF15 | 10.802 |
| POU4F1 | 10.085 | SOX11 | 10.935 | TCF12 | 9.286 | GLIS2 | 10.64 |
| HOXD3 | 9.98 | ASCL1 | 10.394 | RARA | 9.26 | NEUROD1 | 10.474 |
| YBX1 | 9.893 | HOXD3 | 10.122 | FOX1 | 9.254 | POU4F1 | 10.286 |
| ASCL1 | 9.804 | NEUROD1 | 9.545 | FOXO3 | 9.117 | SOX11 | 10.232 |
| NRF1 | 9.729 | NR2F1 | 9.434 | KLF15 | 8.792 | PDX1 | 9.977 |
| NEUROD1 | 9.541 | CDX2 | 9.381 | SOX11 | 8.518 | PRDM1 | 9.714 |
| POU3F2 | 9.184 | CREB1 | 9.243 | POU4F1 | 8.308 | FOXO3 | 9.44 |
| NR2F1 | 9.029 | NEUROD6 | 8.991 | FOXS1 | 8.148 | BLZF1 | 9.415 |
| CDX2 | 8.95 | E2F6 | 8.928 | E2F6 | 8.062 | NEUROD6 | 9.284 |
| NEUROD6 | 8.817 | POU3F1 | 8.647 | TAL1 | 8.08 | TCF12 | 9.079 |
| EED | 8.737 | MAX | 8.47 | PITX2 | 7.97 | ERG | 8.983 |
| NR2F2 | 8.534 | HOXB3 | 8.275 | MAX | 7.953 | RARA | 8.9 |
| HOXB3 | 8.37 | NANOG | 8.135 | FOXA1 | 7.913 | PITX2 | 8.858 |
| E2F6 | 8.312 | TCF12 | 8.091 | CREB3 | 7.901 | HOXD3 | 8.562 |
| FOXS1 | 8.298 | FOXS1 | 8.056 | HOXD3 | 7.9 | ETV6 | 8.468 |
| ETV6 | 8.218 | EED | 7.985 | BLZF1 | 7.824 | CREB1 | 8.239 |
| SOX15 | 8.212 | POU3F2 | 7.891 | NEUROD6 | 7.529 | RNF2 | 8.15 |
| FLI1 | 8.078 | NFIC | 7.803 | NFIB | 7.47 | SOX2 | 7.964 |

Fig. 4D

| TFs | Medulla_Oblongata | TFs | Globus_pallidus | TFs | Subthalamic_nucleus | TFs | Parietal_Lobe |
|---|---|---|---|---|---|---|---|
| NEUROG2 | 17.512 | NEUROG2 | 18.036 | NEUROG2 | 17.106 | NEUROG2 | 17.280 |
| HOXA2 | 15.864 | HOXA2 | 14.41 | HOXA2 | 15.168 | HOXA2 | 15.028 |
| SOX17 | 14.736 | NEUROG1 | 13.993 | NEUROG1 | 13.982 | NEUROG3 | 14.204 |
| SOX7 | 14.731 | NEUROG3 | 13.084 | NEUROG3 | 13.973 | NEUROG1 | 14.147 |
| NEUROG3 | 14.422 | NRF1 | 12.703 | NRF1 | 11.944 | SOX7 | 13.038 |
| NEUROG1 | 14.373 | SOX7 | 11.333 | SOX7 | 11.931 | SOX17 | 12.925 |
| NRF1 | 12.561 | MXI1 | 11.312 | MXI1 | 11.469 | MXI1 | 12.498 |
| MXI1 | 11.942 | SOX17 | 11.273 | SOX17 | 11.338 | NRF1 | 12.327 |
| GLIS2 | 11.709 | YBX1 | 10.379 | YBX1 | 11.149 | YBX1 | 12.112 |
| PDX1 | 11.679 | GLIS2 | 9.853 | SOX11 | 10.818 | GLIS2 | 11.121 |
| SOX11 | 11.424 | ASCL1 | 9.801 | ASCL1 | 10.284 | SOX11 | 10.616 |
| SOX2 | 11.226 | PDX1 | 9.672 | PDX1 | 9.724 | ASCL1 | 10.540 |
| ASCL1 | 10.608 | POU4F1 | 9.583 | POU4F1 | 9.649 | SOX2 | 9.896 |
| YBX1 | 10.549 | ETV6 | 9.558 | GLIS2 | 9.585 | PDX1 | 9.76 |
| SOX10 | 10.523 | SOX11 | 9.328 | TCF12 | 9.503 | SOX10 | 9.383 |
| CREB1 | 10.469 | CREB1 | 9.222 | RARA | 9.369 | ETV6 | 9.303 |
| NR2F1 | 9.752 | RARA | 9.198 | FOXD1 | 9.062 | CREB1 | 9.289 |
| HOXD3 | 9.469 | TAL1 | 8.777 | NEUROD1 | 9.037 | POU4F1 | 9.089 |
| NEUROD6 | 9.201 | SOX2 | 8.684 | ETV6 | 8.967 | RARA | 8.887 |
| FLI1 | 9.187 | FLI1 | 8.552 | CREB1 | 8.769 | NEUROD6 | 8.599 |
| NR2F2 | 8.98 | TCF12 | 8.428 | NEUROD6 | 8.62 | TCF12 | 8.318 |
| POU4F1 | 8.952 | NEUROD6 | 8.229 | E2F6 | 8.296 | TAL1 | 8.098 |
| RARA | 8.814 | ERG | 8.208 | TAL1 | 8.234 | HOXD3 | 8.029 |
| ETV6 | 8.731 | E2F6 | 8.17 | FOXS1 | 8.132 | E2F6 | 7.994 |
| CDX2 | 8.611 | FOXD1 | 8.053 | SOX2 | 8.088 | NEUROD1 | 7.993 |
| NEUROD1 | 8.559 | NEUROD1 | 7.983 | FLI1 | 7.983 | FOXS1 | 7.909 |
| SOX15 | 8.348 | REPIN1 | 7.871 | NR2F1 | 7.784 | FLI1 | 7.892 |
| E2F6 | 8.334 | RNF2 | 7.832 | ZBED4 | 7.752 | KLF15 | 7.848 |
| TCF12 | 8.288 | ZBED4 | 7.53 | HOXB3 | 7.619 | FOXD1 | 7.771 |
| NFIC | 8.032 | BLZF1 | 7.508 | KLF15 | 7.48 | BLZF1 | 7.686 |

Fig. 4E

| TFs | Temporal_Lobe | TFs | Pons | TFs | Olfactory_Bulb | TFs | Spinal_cord |
|---|---|---|---|---|---|---|---|
| NEUROG2 | 15.934 | HOXA2 | 16.458 | SOX9 | 19.528 | SOX10 | 16.182 |
| NRF1 | 14.735 | NRF1 | 15.134 | SOX10 | 17.216 | SOX9 | 14.913 |
| HOXA2 | 13.938 | NEUROG2 | 15.007 | NFIB | 15.085 | SOX17 | 13.833 |
| NEUROG3 | 13.001 | CREB3 | 12.778 | TBX2 | 14.016 | GLIS2 | 12.51 |
| NEUROG1 | 12.9 | GLIS2 | 12.7 | SOX17 | 13.542 | SOX2 | 11.858 |
| SOX7 | 10.267 | NEUROG1 | 12.442 | GLIS2 | 12.924 | SOX7 | 11.685 |
| GLIS2 | 9.736 | SOX17 | 12.352 | SOX2 | 12.081 | HOXA2 | 11.516 |
| CREB1 | 9.418 | NEUROG3 | 11.928 | HES1 | 11.757 | NFIB | 11.022 |
| MXI1 | 9.268 | SOX7 | 11.511 | JUNB | 11.526 | KLF15 | 10.133 |
| SOX17 | 9.183 | ERG | 10.474 | ARNT2 | 11.495 | ARNT2 | 9.18 |
| PBX3 | 9.058 | RARA | 10.394 | NFIC | 11.479 | TBX3 | 8.983 |
| SOX11 | 9.042 | FOXI1 | 10.077 | TBX3 | 11.448 | TBX2 | 8.781 |
| FOXD1 | 8.841 | CTCF | 10.024 | KLF15 | 11.016 | TCF12 | 8.596 |
| REPIN1 | 8.741 | SOX11 | 9.782 | FOS | 10.715 | NR2F1 | 8.28 |
| RNF2 | 8.391 | TAL1 | 9.802 | FEV | 10.186 | NEUROG2 | 8.098 |
| NEUROD1 | 8.372 | FOXD1 | 9.637 | NR2F1 | 10.032 | MAX | 8.031 |
| PITX2 | 8.343 | MXI1 | 9.579 | TP73 | 10.028 | FOXA1 | 7.898 |
| NEUROD6 | 8.271 | TCF12 | 9.295 | FOXA2 | 9.980 | SREBF2 | 7.893 |
| ASCL1 | 8.266 | HES1 | 9.274 | SOX7 | 9.904 | E2F6 | 7.931 |
| KLF15 | 8.058 | YBX1 | 9.209 | CTCF | 9.894 | FEV | 7.811 |
| TAL1 | 8.019 | ASCL1 | 8.906 | HEY1 | 9.86 | HES1 | 7.58 |
| POU4F1 | 7.937 | FLI1 | 8.994 | TFAP2B | 9.852 | MXI1 | 7.578 |
| SNAPC3 | 7.71 | NR2F1 | 8.921 | GATA3 | 9.587 | NRF1 | 7.482 |
| RARA | 7.621 | MAX | 8.71 | IRF4 | 9.547 | RARA | 7.438 |
| PPARGC1A | 7.541 | REPIN1 | 8.893 | HNF1A | 9.426 | FOXC1 | 7.431 |
| TCF12 | 7.501 | SNAPC1 | 8.89 | FOXS1 | 9.337 | FOXA2 | 7.329 |
| ZNF281 | 7.402 | SOX2 | 8.872 | FOXA1 | 9.18 | FOXS1 | 7.297 |
| HOXA3 | 7.358 | NR2F2 | 8.686 | HOXA2 | 9.105 | LHX3 | 7.104 |
| SOX2 | 7.272 | KLF15 | 8.544 | FOSL1 | 8.935 | SOX15 | 7.073 |
| HOXD3 | 7.147 | RNF2 | 8.529 | NANOG | 8.986 | NEUROG1 | 7.033 |

Fig. 4F

| TFs | Heart | TFs | Skeletal_Muscle_Psoas | TFs | Tongue | TFs | Skin |
|---|---|---|---|---|---|---|---|
| TGIF1 | 25.593 | MYOD1 | 18.324 | MYOD1 | 14.122 | HES1 | 16.201 |
| ZNF280B | 22.359 | NRF1 | 12.95 | TP73 | 13.943 | HEY1 | 13.885 |
| SALL4 | 21.804 | PPARGC1A | 12.221 | JUNB | 11.917 | TP73 | 13.296 |
| SOX14 | 21.484 | TAL1 | 11.918 | HES1 | 11.695 | JUNB | 12.97 |
| ESPLAM | 21.138 | SALL3 | 11.343 | KLF4 | 10.948 | CTCF | 12.888 |
| PITX2 | 20.426 | CREB1 | 11.036 | FOS | 10.683 | CREB1 | 12.037 |
| TAL1 | 19.841 | REPIN1 | 9.573 | SALL4 | 10.208 | GLIS2 | 11.921 |
| ZNF281 | 19.018 | CTCFL | 9.443 | FOSL1 | 9.898 | TFAP2C | 10.897 |
| ARID3A | 18.918 | HOXA2 | 9.41 | FOSL2 | 9.781 | HOXA2 | 10.802 |
| PPARGC1A | 18.471 | ERG | 9.326 | NRF1 | 9.582 | NRF1 | 10.454 |
| CTCFL | 18.397 | ZNF281 | 9.174 | HEY1 | 9.463 | TBX5 | 10.431 |
| NKX6-1 | 17.703 | TP73 | 9.086 | TFAP2C | 9.285 | FOS | 9.986 |
| PTAFR | 17.308 | CTCF | 8.739 | ZNF281 | 9.089 | GRHL2 | 9.528 |
| KLF15 | 17.113 | HES1 | 8.522 | GRHL2 | 8.931 | NFIC | 9.279 |
| TFE3 | 16.714 | KLF9 | 8.488 | TBX5 | 8.89 | ESX1 | 9.284 |
| NFIB | 16.662 | BLZF1 | 8.145 | ESX1 | 8.851 | ELF1 | 9.023 |
| TP73 | 16.438 | FOXP1 | 7.977 | PPARGC1A | 8.616 | ERG | 9.019 |
| TCF4 | 16.135 | SOX14 | 7.939 | FOXP1 | 8.558 | CEBPA | 8.807 |
| FOS | 15.858 | YBX3 | 7.731 | GLIS2 | 8.542 | GATA2 | 8.779 |
| DLX6 | 15.687 | PROM1 | 7.718 | NFIB | 8.38 | THAP11 | 8.988 |
| FOXP1 | 15.178 | TLK1 | 7.572 | HOXA2 | 8.177 | THAP7 | 8.634 |
| MAB21L3 | 14.696 | PTAFR | 7.483 | REPIN1 | 8.104 | FOXP1 | 8.541 |
| NRF1 | 14.218 | TCF4 | 7.478 | FEV | 8.089 | IRF5 | 8.515 |
| ELK1 | 13.879 | KLF3 | 7.31 | PTAFR | 7.989 | ZIC1 | 8.476 |
| ESX1 | 13.903 | PITX2 | 7.367 | ZIC1 | 7.941 | GATA3 | 8.307 |
| POU2AF1 | 13.961 | HEY1 | 7.088 | CREB1 | 7.786 | MEIS2 | 8.239 |
| FOSL2 | 13.256 | YY1 | 6.949 | TFE3 | 7.071 | FBXO15 | 8.222 |
| MSX2 | 13.218 | NFIB | 6.938 | ELF1 | 7.402 | TBX2 | 8.141 |
| VDR | 13.083 | ZIC1 | 6.899 | GATA3 | 7.207 | FOSL1 | 8.1 |
| HOXA9 | 12.912 | PA2G4 | 6.862 | ESRRB | 7.198 | FEV | 8.028 |

Fig. 4G

| TFs | Dorsal_root_ganglion | TFs | Appendix | TFs | Superior_Cervical_Ganglion | TFs | Atrioventricular_node |
|---|---|---|---|---|---|---|---|
| HES1 | 17.817 | HES1 | 19.088 | HES1 | 17.35 | HES1 | 16.167 |
| GLIS2 | 17.284 | HEY1 | 16.408 | YBX1 | 14.977 | HEY1 | 14.29 |
| HOXA2 | 16.028 | CTCF | 16.178 | HEY1 | 14.862 | HOXA2 | 14.017 |
| HEY1 | 14.189 | HOXA2 | 15.884 | CREB1 | 14.779 | CTCF | 13.879 |
| TBX2 | 13.915 | GLIS2 | 15.428 | CTCF | 14.480 | NRF1 | 13.827 |
| CTCF | 13.783 | SOX17 | 15.405 | HOXA2 | 14.413 | CREB1 | 13.434 |
| NRF1 | 13.569 | TBX2 | 13.98 | NRF1 | 14.172 | THAP7 | 13.759 |
| SOX17 | 12.688 | CREB1 | 13.521 | FLI1 | 12.884 | GLIS2 | 11.644 |
| REPIN1 | 11.948 | THAP7 | 13.237 | GLIS2 | 12.722 | ERG | 11.355 |
| NR2F1 | 11.538 | NR2F2 | 13.18 | ERG | 12.426 | NFIC | 11.019 |
| NR2F2 | 11.235 | NRF1 | 12.984 | TBX2 | 11.288 | TBX2 | 10.961 |
| RARA | 11.207 | JUNB | 12.849 | NFIC | 10.826 | TBX3 | 10.881 |
| JUNB | 11.073 | NFIC | 12.487 | TBX5 | 10.75 | SOX17 | 10.693 |
| TBX3 | 11.024 | TBX5 | 12.442 | TAL1 | 10.928 | TAL1 | 10.086 |
| ERG | 10.951 | ERG | 12.247 | NR2F2 | 10.593 | TP73 | 10.074 |
| CREB1 | 10.8 | TBX3 | 11.352 | MEIS2 | 10.578 | JUNB | 9.981 |
| TBX5 | 10.456 | FLI1 | 10.6 | SOX17 | 10.359 | YBX1 | 9.957 |
| NFIC | 10.397 | FBXO15 | 10.482 | GATA2 | 10.083 | FBXO15 | 9.77 |
| E2F6 | 10.312 | PDX1 | 10.459 | ETV5 | 9.972 | REPIN1 | 9.464 |
| TCF12 | 10.282 | NR4A2 | 10.281 | FOXK1 | 9.941 | GATA2 | 9.349 |
| FEV | 9.872 | ARNT2 | 10.239 | REPIN1 | 9.643 | NR2F2 | 9.225 |
| THAP7 | 9.842 | NR2F1 | 10.195 | FBXO15 | 9.497 | THAP11 | 9.087 |
| FOS | 9.635 | ELF1 | 9.923 | JUNB | 9.423 | FLI1 | 8.926 |
| SOX9 | 9.376 | SOX15 | 9.773 | MKRN1 | 9.216 | TCF12 | 8.705 |
| NFIB | 9.303 | SOX2 | 9.753 | THAP7 | 9.172 | RARA | 8.559 |
| SREBF2 | 9.175 | GATA2 | 9.521 | SOX11 | 9.189 | NFIB | 8.473 |
| FOXK1 | 9.059 | REPIN1 | 9.436 | NR2F1 | 9.091 | TFAP2C | 8.413 |
| TAL1 | 8.993 | IRF1 | 9.397 | RNF2 | 9.09 | MKRN1 | 8.395 |
| ARNT2 | 8.78 | MEIS2 | 9.377 | TCF12 | 9.026 | TCEA3 | 8.373 |
| SOX10 | 8.548 | E2F6 | 9.363 | RARA | 9.028 | NR2F1 | 8.363 |

Fig. 4H

| TFs | Trigeminal_Ganglion | TFs | Ciliary_ganglion | TFs | Uterus_Corpus | TFs | Ovary |
|---|---|---|---|---|---|---|---|
| HES1 | 17.93 | HES1 | 21.185 | HES1 | 15.483 | HEY1 | 12.869 |
| HEY1 | 15.928 | GLIS2 | 18.412 | JUNB | 14.577 | HES1 | 12.724 |
| HOXA2 | 15.427 | NRF1 | 16.899 | FOS | 14.035 | TBX2 | 9.614 |
| NRF1 | 15.083 | CTCF | 16.683 | GLIS2 | 13.61 | CTCF | 9.839 |
| GLIS2 | 14.582 | HEY1 | 16.348 | HEY1 | 13.39 | TBX3 | 9.806 |
| CTCF | 13.786 | CREB1 | 15.98 | CTCF | 13.123 | THAP7 | 9.593 |
| CREB1 | 13.352 | HOXA2 | 15.801 | FOSL1 | 12.185 | GLIS2 | 9.589 |
| ERG | 11.741 | JUNB | 15.793 | ARNT2 | 11.835 | HOXA2 | 8.997 |
| JUNB | 11.493 | NFIC | 14.936 | THAP7 | 11.635 | JUNB | 8.725 |
| TBX2 | 11.451 | ARNT2 | 13.354 | CREB1 | 11.391 | FBXO15 | 8.515 |
| NR2F2 | 10.724 | TBX2 | 13.308 | JUN | 10.88 | NR2F2 | 8.398 |
| REPIN1 | 10.864 | ERG | 13.259 | ERG | 10.868 | CREB1 | 8.344 |
| TBX5 | 10.521 | NFIB | 12.898 | NRF1 | 10.884 | SOX17 | 8.232 |
| NFIC | 10.448 | FEV | 12.464 | NFIB | 10.867 | NR2F1 | 8.233 |
| SOX17 | 10.114 | FOS | 12.463 | TBX3 | 10.642 | NR4A2 | 8.225 |
| RARA | 10.106 | TCF12 | 12.13 | HOXA2 | 10.623 | NFIC | 7.753 |
| THAP7 | 10.041 | TBX5 | 11.972 | ZNF281 | 10.508 | ERG | 7.676 |
| TBX3 | 9.892 | SOX17 | 11.873 | THAP11 | 10.482 | TBX5 | 7.675 |
| TAL1 | 9.952 | REPIN1 | 11.825 | TBX2 | 10.469 | NRF1 | 7.551 |
| TCF12 | 9.108 | THAP7 | 11.566 | TBX5 | 10.173 | ARNT2 | 7.372 |
| NR2F1 | 9.068 | NR2F2 | 11.523 | ELF3 | 10.047 | CEBPD | 7.282 |
| TP73 | 8.912 | ZNF281 | 11.398 | NFIC | 9.98 | CEBPA | 7.252 |
| FLI1 | 8.837 | NR2F1 | 11.32 | TFAP2C | 9.898 | BHLHE40 | 6.993 |
| FBXO15 | 8.717 | TP73 | 10.708 | TP73 | 9.856 | ELF5 | 6.905 |
| ARNT2 | 8.674 | TBX1 | 10.473 | EGR2 | 9.828 | TFAP4 | 6.801 |
| FEV | 8.608 | FOSL1 | 10.361 | ZIC1 | 9.713 | ELF3 | 6.774 |
| ZNF281 | 8.639 | FOXP1 | 10.311 | MEIS1 | 9.303 | MSC | 6.719 |
| E2F6 | 8.587 | FBXO15 | 10.097 | ELF1 | 9.302 | PTAFR | 6.478 |
| ELF1 | 8.574 | TFAP2C | 9.979 | ESX1 | 9.236 | ZNF281 | 6.46 |
| YBX1 | 8.57 | IRF4 | 9.857 | PTAFR | 9.092 | GATA3 | 6.428 |

Fig. 4I

| TFs | Adrenal_Cortex | TFs | Adrenal_gland | TFs | Placenta | TFs | Lung |
|---|---|---|---|---|---|---|---|
| SALL4 | 11.683 | SALL4 | 11.871 | TFAP2C | 20.889 | SOX14 | 25.717 |
| FOXP1 | 11.164 | TFE3 | 11.563 | FOS | 20.266 | TGIF1 | 25.341 |
| HES1 | 11.102 | TGIF1 | 11.488 | TP73 | 20.042 | FOS | 24.706 |
| ESX1 | 10.342 | SOX14 | 11.383 | ESX1 | 19.489 | SALL4 | 23.855 |
| ZNF283 | 10.158 | NFIB | 10.993 | GATA3 | 19.088 | TP73 | 23.138 |
| HEY1 | 10.011 | DLX6 | 10.949 | JUNB | 18.963 | ESX1 | 23.082 |
| TAL1 | 8.967 | FOS | 10.893 | TFE3 | 17.891 | NFIB | 22.73 |
| PITX2 | 8.925 | HOXA9 | 10.584 | IRF5 | 17.632 | TFE3 | 22.142 |
| ZIC1 | 8.88 | ESX1 | 10.062 | FOSL1 | 16.233 | TFAP2C | 21.76 |
| SOX14 | 8.835 | TP73 | 10.038 | CEBPB | 15.633 | DLX6 | 21.137 |
| TP73 | 8.781 | CEBPB | 9.987 | FOXP1 | 14.984 | PITX2 | 20.837 |
| ARNT2 | 8.779 | GATA3 | 9.812 | NFIB | 14.705 | KLF15 | 20.098 |
| EGR2 | 8.668 | ZNF281 | 9.809 | NKX6-2 | 14.632 | NKX6-1 | 19.626 |
| DLX6 | 8.638 | ELK1 | 9.768 | TFAP2B | 14.611 | MSX2 | 19.369 |
| NRF1 | 8.613 | ZIC1 | 9.428 | JUN | 14.47 | ZNF281 | 19.15 |
| KLF15 | 8.610 | HES1 | 9.256 | ESRRB | 14.434 | PTAFR | 18.824 |
| GATA3 | 8.38 | CTCFL | 9.18 | DLX6 | 14.298 | ARID3A | 18.312 |
| FOS | 8.33 | FOXP1 | 9.082 | MSX2 | 14.173 | NKX6-2 | 17.954 |
| TGIF1 | 8.274 | ARID3A | 9.021 | ETS2 | 13.798 | FOXP1 | 17.94 |
| ERG | 8.149 | KLF15 | 8.971 | SOX14 | 13.621 | ELK1 | 17.919 |
| TFE3 | 8.072 | TFAP2C | 8.919 | ELK1 | 13.548 | TCF4 | 17.888 |
| JUNB | 8.035 | PITX2 | 8.828 | HHEX | 13.395 | HOXA9 | 17.312 |
| NFIB | 7.956 | ARNT2 | 8.796 | ZBTB3 | 13.263 | ZNF280B | 16.892 |
| TBX5 | 7.869 | EGFLAM | 8.548 | HES1 | 13.262 | MNX1 | 16.682 |
| ELK3 | 7.625 | JUNB | 8.563 | ESR1 | 13.17 | EGFLAM | 16.47 |
| TFAP2C | 7.528 | NKX6-2 | 8.112 | TFAP2A | 12.874 | TAL1 | 16.246 |
| NR4A2 | 7.559 | NKX6-1 | 7.945 | ARNT2 | 12.987 | JUNB | 16.075 |
| PPARGC1A | 7.324 | PPARGC1A | 7.629 | FIGLA | 12.239 | HHEX | 16.014 |
| SREBF2 | 7.293 | NR4A2 | 7.489 | ELF1 | 12.231 | GATA3 | 15.892 |
| CTCFL | 7.14 | ZBTB3 | 7.402 | GLIS2 | 12.184 | FOSL2 | 15.724 |

Fig. 4J

| TFs | Fetal_lung | TFs | Trachea | TFs | Kidney | TFs | Liver |
|---|---|---|---|---|---|---|---|
| CEBPB | 15.141 | JUNB | 14.968 | HNF4A | 17.058 | TGIF1 | 20.477 |
| GATA3 | 14.01 | HES1 | 14.574 | TGIF1 | 14.086 | EGFLAM | 20.328 |
| JUNB | 13.287 | GATA3 | 14.272 | SOX14 | 14.069 | SALL4 | 18.239 |
| BARHL2 | 12.087 | CEBPA | 13.544 | SALL4 | 14.017 | TAL1 | 17.148 |
| IRF5 | 11.828 | IRF5 | 13.207 | PPARGC1A | 12.387 | POU2AF1 | 15.795 |
| NKX6-2 | 11.733 | FOS | 12.935 | EGFLAM | 12.263 | ZNF280B | 15.839 |
| NFIB | 11.488 | TFAP2C | 12.878 | TFE3 | 12.125 | SOX14 | 15.548 |
| CEBPA | 11.479 | TP73 | 12.887 | HOXA9 | 12.038 | NKX6-1 | 14.872 |
| HEY1 | 10.759 | HEY1 | 12.609 | FOS | 11.752 | ARID3A | 14.375 |
| ETS2 | 10.879 | SOX9 | 12.570 | NKX6-3 | 11.603 | MAB21L3 | 14.196 |
| JUN | 10.552 | CEBPB | 12.486 | ZNF280B | 11.483 | CTCFL | 14.044 |
| ESX1 | 10.517 | ELF1 | 12.347 | CTCFL | 11.439 | PPARGC1A | 13.691 |
| FOSL1 | 10.384 | FOXA2 | 12.149 | ARID3A | 11.275 | REPIN1 | 12.946 |
| ESRRB | 10.368 | NFIB | 11.34 | REPIN1 | 10.948 | PITX2 | 12.592 |
| HSF1 | 10.322 | IRF4 | 11.304 | NFIB | 10.63 | HNF4A | 12.437 |
| HES1 | 10.138 | TFAP2B | 11.072 | TP73 | 10.487 | TCF4 | 11.967 |
| TFAP2C | 9.885 | FOXA1 | 10.643 | HNF1A | 10.194 | VDR | 11.622 |
| NR4A2 | 9.793 | NR4A2 | 10.54 | GATA3 | 10.073 | TFE3 | 11.359 |
| IRF4 | 9.743 | ESRRB | 10.474 | TCF4 | 9.906 | KLF15 | 11.33 |
| ELF1 | 9.692 | GLIS2 | 10.422 | SMAD7 | 9.812 | SNAPC1 | 10.945 |
| TFAP2B | 9.620 | ESX1 | 10.331 | RFX2 | 9.68 | DLX6 | 10.787 |
| ARNT2 | 9.518 | SPI1 | 10.323 | TFAP2C | 9.471 | SPZ1 | 10.529 |
| FOS | 9.444 | NFIC | 10.219 | POU2AF1 | 9.435 | TLK1 | 10.495 |
| TBX2 | 9.366 | FOSL1 | 10.373 | ELK1 | 9.068 | SMAD7 | 10.488 |
| ETS1 | 9.005 | SPIB | 9.973 | TCF12 | 9.034 | TP73 | 10.408 |
| GATA6 | 8.971 | TBX3 | 9.883 | NKX6-2 | 8.996 | SUB1 | 10.319 |
| HHEX | 8.82 | IRF1 | 9.841 | DLX6 | 8.868 | ZNF281 | 10.282 |
| PTAFR | 8.779 | BARHL2 | 9.757 | NRF1 | 8.614 | HOXA9 | 10.251 |
| NKX2-1 | 8.439 | SOX10 | 9.704 | SALL1 | 8.541 | UCP2 | 10.195 |
| GLIS2 | 8.382 | E2F6 | 9.571 | FOXP1 | 8.398 | NELFA | 9.927 |

Fig. 4K

| TFs | Prostate | TFs | Thyroid | TFs | Fetal_Thyroid | TFs | Cultured_adipocyte |
|---|---|---|---|---|---|---|---|
| TP73 | 14.045 | FIGLA | 11.444 | HHEX | 10.604 | JUN | 15.683 |
| NFIB | 13.789 | NFIB | 11.149 | FIGLA | 10.500 | FOSL1 | 13.371 |
| FOS | 13.742 | NKX2-1 | 8.993 | NKX6-2 | 10.432 | NFIB | 12.714 |
| NKX6-2 | 13.106 | NKX6-2 | 8.979 | NFIB | 10.377 | FOS | 11.74 |
| SOX14 | 12.108 | MYOD1 | 8.566 | MNX1 | 8.803 | HES1 | 10.404 |
| IRF6 | 11.628 | IRX2 | 8.228 | TGIF1 | 8.605 | GLIS2 | 10.236 |
| HHEX | 11.53 | HHEX | 8.209 | NKX2-1 | 8.309 | JUNB | 10.221 |
| TFAP2C | 11.454 | MNX1 | 7.767 | BARHL2 | 8.103 | SREBF2 | 10.036 |
| MSX2 | 11.343 | PAX8 | 7.583 | ASCL2 | 8.004 | GATA3 | 9.527 |
| FIGLA | 11.291 | FOXA2 | 7.252 | TFAP2C | 7.863 | FEV | 9.526 |
| HOXA9 | 10.848 | BARHL2 | 7.132 | TBX3 | 7.634 | ARNT2 | 9.146 |
| NKX6-1 | 10.758 | E2F8 | 6.987 | FOXP3 | 7.525 | HEY1 | 9.081 |
| TGIF1 | 10.635 | SOX6 | 6.803 | EN1 | 7.519 | CEBPB | 9.062 |
| MNX1 | 10.558 | TGIF1 | 6.706 | MYOD1 | 7.403 | ISL2 | 8.854 |
| ESRRB | 10.48 | TCF12 | 6.702 | MSX2 | 7.292 | NR4A2 | 8.844 |
| DLX6 | 10.335 | CEBPB | 6.646 | NKX6-1 | 7.056 | HSF1 | 8.399 |
| ESX1 | 10.278 | TP73 | 6.545 | SALL4 | 7.024 | E2F8 | 8.259 |
| TCF4 | 10.248 | ASCL2 | 6.237 | IRX2 | 6.981 | TFE3 | 8.239 |
| KLF15 | 9.895 | NKX2-5 | 6.106 | SOX14 | 6.573 | TBX2 | 8.08 |
| BARHL2 | 9.878 | FOXA1 | 6.098 | TBX2 | 6.514 | PTAFR | 8.018 |
| SALL4 | 9.791 | NKX6-1 | 6.063 | PAX8 | 6.287 | FOSL2 | 7.874 |
| CEBPB | 9.788 | EN1 | 6.018 | TCF12 | 6.242 | NKX6-2 | 7.794 |
| GATA3 | 9.771 | TCF4 | 5.898 | GATA3 | 5.897 | ELK1 | 7.787 |
| GRHL2 | 9.342 | FOXC1 | 5.872 | TP73 | 5.739 | TFAP2B | 7.727 |
| PITX2 | 9.142 | SOX30 | 5.841 | NKX2-2 | 5.625 | TFAP2C | 7.694 |
| NKX2-1 | 9.085 | GATA6 | 5.634 | FOS | 5.604 | TBX3 | 7.536 |
| ZBTB3 | 9.041 | GATA3 | 5.419 | KLF15 | 5.554 | RUNX1 | 7.528 |
| JUNB | 9.027 | ESRRB | 5.404 | TFAP2B | 5.43 | RUNX3 | 7.387 |
| FOSL1 | 8.989 | TBX3 | 5.253 | PAX6 | 5.33 | SOX9 | 7.33 |
| TFE3 | 8.844 | HNF4A | 5.236 | ARID3A | 5.281 | ZBTB3 | 7.302 |

Fig. 4L

| TFs | Uterus | TFs | Fetal_liver | TFs | salivary_gland | TFs | Islet_Cell |
|---|---|---|---|---|---|---|---|
| JUNB | 12.854 | EED | 11.864 | EED | 12.800 | ASCL1 | 8.847 |
| JUN | 12.594 | ETV3 | 10.305 | CEBPD | 11.208 | HES1 | 8.672 |
| SOX9 | 12.273 | DEDD2 | 10.179 | GABPA | 11.151 | JUNB | 8.302 |
| BARHL2 | 11.708 | ID1 | 10.137 | CEBPA | 10.824 | CEBPB | 8.242 |
| TFAP2B | 11.686 | ZNF426 | 9.273 | FLI1 | 10.719 | HEY1 | 7.941 |
| GLIS2 | 11.662 | HDAC2 | 9.2 | TCEA3 | 10.100 | ELF1 | 7.733 |
| NFIB | 11.638 | CRY2 | 8.997 | SOX18 | 10.080 | HNF4A | 7.546 |
| NFIC | 11.435 | TCF25 | 8.878 | HEY1 | 10.057 | TCF12 | 7.244 |
| ARNT2 | 11.203 | SMAD5 | 8.808 | SIN3A | 8.848 | FOXA1 | 7.202 |
| SOX10 | 11.102 | RSPO1 | 8.688 | HES1 | 8.829 | TCF4 | 7.16 |
| SOX2 | 11.038 | ZFAND3 | 8.634 | ELF3 | 8.398 | GATA3 | 7.036 |
| GATA2 | 10.85 | PLXNB3 | 8.515 | ZFAND3 | 8.184 | FOXA2 | 6.913 |
| TBX2 | 10.383 | REST | 8.401 | IRF1 | 8.141 | TFE3 | 6.843 |
| HSF1 | 10.359 | TRIM28 | 8.391 | SPIB | 7.807 | IRF5 | 6.605 |
| FOSL1 | 10.348 | DMRTC2 | 8.184 | MEIS2 | 7.787 | HSF1 | 6.54 |
| SOX17 | 10.137 | HOXA3 | 8.069 | CRY2 | 7.764 | E2F6 | 6.464 |
| IRF4 | 10.092 | HDAC8 | 8.065 | TRIM28 | 7.622 | ESRRB | 6.354 |
| THAP7 | 9.943 | CEBPD | 7.96 | E2F6 | 7.57 | CEBPA | 6.35 |
| IRF5 | 9.898 | AATF | 7.881 | SOX17 | 7.506 | WNT3A | 6.209 |
| RUNX3 | 9.886 | HOXB4 | 7.84 | IRF2 | 7.343 | FOS | 6.112 |
| TBX3 | 9.635 | HOPX | 7.707 | NR4A2 | 7.334 | PTAFR | 6.082 |
| FOXA2 | 9.458 | RFXAP | 7.492 | GATA2 | 7.317 | ZIC1 | 6.078 |
| MEIS2 | 9.352 | SSX8 | 7.409 | WNT3A | 7.129 | ELK1 | 5.92 |
| FIGLA | 9.277 | CHD4 | 7.383 | FBXO15 | 7.105 | NR4A2 | 5.826 |
| FOXC1 | 9.188 | LIN28A | 7.305 | SPIC | 6.918 | TRPV2 | 5.811 |
| PTF1A | 9.138 | GABPA | 7.268 | HOXA2 | 6.873 | IRF4 | 5.541 |
| DMRT1 | 9.089 | JAG1 | 7.25 | CHD4 | 6.822 | MSC | 5.431 |
| FOS | 8.98 | STAG1 | 7.22 | SPI1 | 6.496 | FBXO15 | 5.369 |
| SMAD3 | 8.905 | VPS72 | 7.195 | CTCF | 6.481 | HNF1A | 5.36 |
| HEY1 | 8.814 | BCL6 | 7.19 | DMRTC2 | 6.453 | ARNT2 | 4.847 |

Fig. 4M

| TFs | Pancreas | TFs | Cardiac _Myocytes | TFs | Smooth_Muscle | TFs | Colorectal _Adenocarcinoma |
|---|---|---|---|---|---|---|---|
| HNF4A | 11.984 | FOSL1 | 18.967 | JUN | 23.843 | EGFLAM | 13.546 |
| ELF1 | 11.128 | JUN | 16.898 | FOSL1 | 19.207 | SIRT6 | 12.217 |
| HEY1 | 8.326 | PTAFR | 14.785 | HSF1 | 15.767 | MSX2 | 12.123 |
| FBXO15 | 8.184 | FOS | 13.976 | JUNB | 13.311 | SOX14 | 11.383 |
| IRF5 | 7.773 | FOSL2 | 12.575 | FOS | 12.835 | SALL1 | 11.093 |
| PTAFR | 7.656 | JUNB | 12.158 | PTAFR | 12.411 | PTAFR | 10.733 |
| GRHL2 | 7.561 | HSF1 | 11.269 | ISL2 | 11.578 | CBX8 | 10.503 |
| HES1 | 7.505 | GLIS2 | 10.735 | GADD45A | 11.426 | TRAF4 | 9.95 |
| JUNB | 7.378 | ISL2 | 10.326 | CUX1 | 11.182 | NKX6-1 | 9.75 |
| GATA3 | 7.36 | NR4A2 | 9.53 | ARNT2 | 10.863 | IRF5 | 9.49 |
| ESRRB | 7.341 | CCNE1 | 9.458 | GATA3 | 10.526 | SRSF6 | 9.221 |
| WNT5A | 7.327 | ETS2 | 9.113 | ELK3 | 10.524 | MNX1 | 8.941 |
| FOXP1 | 7.307 | IRF5 | 9.035 | IRF5 | 10.397 | DLX6 | 8.795 |
| SALL4 | 7.153 | ARNT2 | 8.864 | ELF1 | 10.279 | ESX1 | 8.792 |
| FOS | 7.036 | GATA3 | 8.579 | FOSL2 | 10.26 | TGIF1 | 8.752 |
| SALL1 | 6.898 | SMAD3 | 8.538 | ETS2 | 10.207 | PML | 8.718 |
| TCF4 | 6.868 | ELF1 | 8.23 | FEV | 10.18 | CUX1 | 8.708 |
| TP73 | 6.581 | NKX6-2 | 8.03 | SNAI1 | 9.753 | NKX6-2 | 8.477 |
| ZIC3 | 6.55 | CUX1 | 7.838 | CCNE1 | 9.71 | FOSL1 | 8.391 |
| MSC | 6.403 | FEV | 7.827 | NR4A2 | 9.547 | GTF3C2 | 8.077 |
| TLX1 | 6.187 | BARHL2 | 7.768 | HES1 | 9.242 | ZMAT4 | 7.832 |
| TCEA3 | 6.122 | ELK3 | 7.743 | GLIS2 | 9.213 | ESRRB | 7.77 |
| FOSL1 | 6.041 | HES1 | 7.613 | SMAD3 | 8.865 | FOSL2 | 7.708 |
| NR4A2 | 6.022 | GADD45A | 7.433 | L3MBTL2 | 8.544 | MYC | 7.682 |
| ELK1 | 5.96 | LHX3 | 7.429 | ELK1 | 8.49 | FOS | 7.582 |
| GABPA | 5.957 | ESX1 | 7.347 | TRPV2 | 8.399 | CCNE1 | 7.38 |
| TFAP2C | 5.875 | ELK3 | 7.287 | SNAI3 | 8.301 | THAP3 | 7.275 |
| HSF1 | 5.854 | TBX2 | 7.076 | NKX6-2 | 8.139 | CDYL2 | 7.27 |
| ESX1 | 5.838 | MEIS1 | 6.978 | BARHL2 | 8.01 | SALL4 | 7.087 |
| WRNIP1 | 5.575 | THAP11 | 6.71 | TFAP2B | 7.736 | FOXP1 | 7.043 |

Fig. 4N

| TFs | Bronchial_epithelial _cells (HBEC) | TFs | Whole_blood (JJV) | TFs | Myeloid (BM_CD33) | TFs | Monocytes (PB_CD14) |
|---|---|---|---|---|---|---|---|
| MYC | 15.679 | SPIB | 23.237 | SPIB | 17.283 | SPIB | 18.754 |
| JUN | 14.397 | SPI1 | 20.872 | SPI1 | 14.744 | SPI1 | 14.76 |
| GADD45A | 14.221 | CEBPB | 17.829 | CEBPB | 13.181 | ETS1 | 12.827 |
| REST | 14.082 | ETS1 | 17.34 | ETS1 | 12.614 | CEBPB | 12.377 |
| FOSL1 | 13.448 | CEBPA | 16.089 | CEBPD | 12.423 | CDYL2 | 12.169 |
| CCNE1 | 12.856 | ELF1 | 15.708 | CDYL2 | 11.77 | CEBPD | 10.583 |
| TRPV2 | 12.36 | CEBPD | 15.373 | CEBPA | 11.573 | ELF1 | 9.901 |
| SIRT6 | 12.023 | SPIC | 14.526 | ELF1 | 10.989 | IRF1 | 9.716 |
| L3MBTL2 | 10.931 | ETS2 | 12.547 | SPIC | 10.206 | GADD45A | 9.05 |
| ELK3 | 9.789 | IRF1 | 11.362 | IRF1 | 8.76 | SPIC | 9.001 |
| CUX1 | 9.615 | DMRT1 | 10.234 | RUNX1 | 8.458 | REST | 8.398 |
| ZMAT4 | 9.526 | KLF4 | 9.565 | GADD45A | 8.029 | ZSCAN4 | 8.38 |
| CBX8 | 9.378 | RUNX1 | 9.389 | ZSCAN4 | 7.956 | CEBPA | 8.278 |
| IRF5 | 9.294 | CDYL2 | 8.924 | ETS2 | 7.919 | MYC | 7.714 |
| AATF | 9.287 | MYB | 8.622 | REST | 7.896 | RUNX1 | 7.695 |
| LIN28A | 9.238 | IRF2 | 8.323 | L3MBTL2 | 7.687 | ETS2 | 7.49 |
| HSF1 | 8.654 | ZSCAN4 | 7.866 | DMRT1 | 7.56 | KLF4 | 7.452 |
| SSX6 | 8.357 | RUNX3 | 7.777 | RUNX3 | 7.105 | L3MBTL2 | 7.25 |
| JUNB | 8.117 | GADD45A | 7.969 | MYBL2 | 6.959 | SIRT6 | 6.920 |
| PLXNB3 | 8.054 | ELF5 | 7.050 | KLF4 | 6.896 | CUX1 | 6.443 |
| ESRRB | 8.04 | TBX6 | 6.301 | MYB | 6.654 | TRPV2 | 6.339 |
| FOXN3 | 7.813 | MYBL2 | 6.353 | MYC | 6.82 | DMRT1 | 6.356 |
| BRF2 | 7.62 | L3MBTL2 | 6.15 | SIRT6 | 6.225 | ZMAT4 | 6.264 |
| SRSF6 | 7.583 | GLI1 | 5.534 | OTX1 | 6.168 | MYB | 6.17 |
| EGFLAM | 7.548 | SALL4 | 5.49 | PAX8 | 5.63 | CBX8 | 6.105 |
| ELF1 | 7.437 | PAX8 | 5.38 | IRF2 | 5.5 | PAX8 | 6.072 |
| CDYL2 | 7.436 | IRF4 | 5.26 | CUX1 | 5.137 | RUVBL2 | 5.596 |
| ISL2 | 7.404 | IRF5 | 5.221 | TRPV2 | 4.295 | OVOL2 | 5.485 |
| HOXB4 | 7.209 | PAX5 | 5.167 | CHD4 | 4.29 | ATF2 | 5.457 |
| ZSCAN4 | 7.178 | ESX1 | 5.127 | IRF4 | 4.113 | RUNX3 | 5.357 |

Fig. 4O

| TFs | Lymphnode | TFs | Tonsil | TFs | Bone_marrow | TFs | Thymus |
|---|---|---|---|---|---|---|---|
| SPIB | 17.725 | SPIB | 15.81 | SALL4 | 12.849 | POU2AF1 | 12.03 |
| SPI1 | 15.909 | SPI1 | 14.383 | CEBPB | 11.465 | SOX14 | 11.025 |
| IRF1 | 15.032 | IRF1 | 11.758 | SPIB | 10.875 | ESX1 | 10.074 |
| IRF8 | 13.958 | ELF3 | 11.421 | ESX1 | 10.247 | EGFLAM | 10.038 |
| ETS1 | 13.493 | IRF2 | 11.144 | SPI1 | 9.488 | GTF3C2 | 9.8 |
| ELF1 | 13.241 | SPIC | 10.849 | SOX14 | 9.287 | FOXM1 | 9.894 |
| SPIC | 12.727 | IRF5 | 8.474 | CTCFL | 9.128 | MSX2 | 9.438 |
| ETS2 | 12.473 | ESX1 | 8.056 | POU2AF1 | 9.024 | SALL4 | 9.038 |
| IRF4 | 10.723 | IRF4 | 8.027 | EGFLAM | 8.727 | RFX2 | 8.626 |
| RUNX3 | 8.963 | ETS1 | 7.907 | ELF1 | 8.8 | ARID3A | 8.021 |
| ELF5 | 8.77 | KLF4 | 7.552 | SALL1 | 8.532 | HOXA9 | 7.777 |
| JUNB | 8.579 | SIRT6 | 7.03 | ZNF281 | 8.44 | ZNF280B | 7.519 |
| RUNX1 | 8.127 | CEBPD | 6.802 | CEBPA | 8.067 | ETS1 | 7.384 |
| CEBPD | 7.937 | ZFAND3 | 6.482 | DLX6 | 8.054 | RUNX1 | 7.275 |
| IRF5 | 7.811 | CEBPA | 6.461 | ETS1 | 7.962 | DLX6 | 7.269 |
| TBX5 | 7.58 | SALL3 | 6.383 | FOXP1 | 7.783 | CBX8 | 7.108 |
| HEY1 | 7.327 | PA2G4 | 6.102 | TFE3 | 7.785 | RUVBL2 | 7.089 |
| ESX1 | 7.321 | CHD4 | 6.198 | KLF4 | 7.621 | BATF | 6.939 |
| DMRT1 | 7.111 | FOXN3 | 6.079 | TGIF1 | 7.523 | SPIB | 6.907 |
| CEBPB | 7.087 | JUNB | 5.798 | ZNF280B | 7.374 | SALL1 | 6.865 |
| HES1 | 7.003 | CDYL2 | 5.685 | CEBPD | 6.939 | NKX6-1 | 6.606 |
| SALL4 | 6.859 | CBX8 | 5.548 | ELF5 | 6.844 | SPI1 | 6.513 |
| CEBPA | 6.254 | AATF | 5.525 | PA2G4 | 6.757 | CTCFL | 6.355 |
| FOXP1 | 6.208 | GABPA | 5.485 | HOXA9 | 6.079 | MNX1 | 6.339 |
| TFAP2C | 5.81 | ELF5 | 5.476 | SPIC | 6.832 | CCNE1 | 6.192 |
| ZIC1 | 5.735 | TCEA3 | 5.424 | MKRN1 | 6.609 | ID3 | 6.116 |
| HSF1 | 5.509 | TP73 | 5.224 | FOXM1 | 6.518 | UCP2 | 6.081 |
| TCEA3 | 5.495 | SALL1 | 5.195 | FOS | 6.473 | THAP1 | 6.017 |
| GATA3 | 5.479 | ZSCAN4 | 5.146 | TFAP2C | 6.356 | TGM2 | 5.943 |
| TP73 | 5.384 | SETDB1 | 5.064 | RFX2 | 6.304 | IRF2 | 5.824 |

Fig. 4P

| TFs | Natural_Killer_Cells (PB_CD56) | TFs | Dendritic_Cells (PB_BDCA4) | TFs | B_Cells (PB_CD19) | TFs | T_Cells (PB_CD8) |
|---|---|---|---|---|---|---|---|
| CDYL2 | 13.609 | CDYL2 | 13.73 | CDYL2 | 14.067 | CDYL2 | 13.608 |
| REST | 12.305 | SPIB | 12.528 | REST | 13.673 | MYC | 11.987 |
| ETS3 | 9.541 | REST | 12.847 | MYC | 12.304 | REST | 10.833 |
| SPIB | 9.393 | MYC | 11.385 | SSX6 | 11.73 | SSX6 | 9.392 |
| MYC | 9.384 | SPI1 | 10.077 | ATF2 | 11.329 | SIRT6 | 9.233 |
| GADD45A | 9.037 | SIRT6 | 9.823 | SIRT6 | 9.993 | GTF2F1 | 8.71 |
| L3MBTL2 | 8.451 | L3MBTL2 | 9.157 | PML | 9.378 | PML | 8.676 |
| SIRT6 | 8.033 | GADD45A | 9.154 | ID3 | 9.183 | ATF2 | 8.071 |
| SSX6 | 7.812 | ZSCAN4 | 8.802 | ZNF428 | 8.177 | L3MBTL2 | 7.813 |
| ZSCAN4 | 7.736 | ETS3 | 8.38 | L3MBTL2 | 7.997 | STAG1 | 7.574 |
| SPI1 | 7.717 | SSX6 | 7.898 | ZFAND3 | 7.985 | ZSCAN4 | 7.529 |
| ATF2 | 7.706 | ATF2 | 7.781 | RSPO1 | 7.846 | E2F4 | 7.195 |
| RUNX1 | 7.12 | TRPV2 | 6.985 | KLF5 | 7.799 | KLF5 | 6.948 |
| IRF1 | 6.912 | SRSF6 | 6.802 | ID1 | 7.721 | ETS1 | 6.879 |
| PML | 6.839 | ID3 | 6.652 | ZSCAN4 | 7.671 | SIN3A | 6.409 |
| ID1 | 6.495 | ZMAT4 | 6.503 | SPIB | 7.461 | RUVBL2 | 6.238 |
| RUVBL2 | 6.446 | IRF1 | 6.421 | FOXN3 | 7.247 | STRA8 | 6.237 |
| TRPV2 | 6.242 | RUVBL2 | 6.413 | RUVBL2 | 7.118 | JARID2 | 6.198 |
| GLI1 | 6.205 | PML | 6.335 | NR3C1 | 7.111 | GTF3C2 | 6.154 |
| CEBPD | 6.203 | CEBPD | 6.3 | BRF2 | 7.089 | SETDB1 | 6.003 |
| ZNF428 | 6.024 | RUNX1 | 6.068 | SSX4B | 7.028 | SSX4B | 5.99 |
| IRF2 | 5.981 | SPIC | 6.054 | LMO1 | 6.972 | SPI1 | 5.986 |
| GTF3C2 | 5.928 | IRF2 | 5.813 | TRPV2 | 6.958 | SRSF6 | 5.98 |
| JARID2 | 5.925 | FOXN3 | 5.724 | GADD45A | 6.952 | ID3 | 5.93 |
| MYB | 5.839 | OTX1 | 5.943 | GTF2F1 | 6.929 | TRAF4 | 5.893 |
| DMRT1 | 5.751 | ELF1 | 5.57 | SIN3A | 6.918 | BATF | 5.874 |
| KLF5 | 5.543 | JARID2 | 5.37 | STAG1 | 6.707 | EED | 5.798 |
| ID3 | 5.503 | ZNF428 | 5.424 | ZBTB45 | 6.54 | WHSC1 | 5.78 |
| EED | 5.337 | CBX8 | 5.435 | E2F4 | 6.485 | NR3C1 | 5.776 |
| ZMAT4 | 5.247 | NR3C1 | 5.267 | ZMAT4 | 6.452 | SPIB | 5.775 |

Fig. 4Q

| TFs | T_Cells (PB_CD4) | TFs | Early_Erythroid (BM_CD71) | TFs | Lymphoma_Raji | TFs | B_lymphoblasts (721) |
|---|---|---|---|---|---|---|---|
| CDYL2 | 13.778 | REST | 13.823 | MYC | 15.342 | REST | 19.381 |
| MYC | 12.013 | CDYL2 | 13.281 | SIRT8 | 15.225 | MYC | 18.808 |
| REST | 9.914 | E2F4 | 11.802 | PML | 14.263 | SSX8 | 18.857 |
| SIRT8 | 9.862 | SSX6 | 11.308 | ZBTB45 | 13.926 | SIRT8 | 16.284 |
| SSX8 | 8.27 | SIRT8 | 10.72 | VAX1 | 13.907 | CDYL2 | 15.481 |
| PML | 8.024 | ZNF426 | 10.481 | SSX6 | 13.342 | PML | 14.975 |
| GTF2F1 | 8.53 | ATF2 | 8.931 | ESFLAM | 13.154 | RSPO1 | 14.928 |
| ATF2 | 8.26 | GADD45A | 8.886 | SMARCB1 | 13.011 | NR3C1 | 14.898 |
| L3MBTL2 | 7.870 | RUVBL2 | 8.703 | SSX4B | 12.813 | ZNF426 | 14.589 |
| ZSCAN4 | 7.406 | ZSCAN4 | 8.584 | ATF2 | 12.255 | SSX4B | 14.348 |
| STAG1 | 7.258 | PML | 8.245 | SUZ12 | 12.691 | ATF2 | 13.893 |
| KLF5 | 7.002 | GTF2F1 | 8.224 | ZFP57 | 12.411 | ZBTB45 | 13.253 |
| GTF3C2 | 6.817 | MYC | 8.164 | LIN28A | 12.34 | ZFAND3 | 13.023 |
| E2F4 | 6.705 | SRSF8 | 8.105 | SUB1 | 12.103 | RUVBL2 | 12.381 |
| ETS1 | 6.018 | ID3 | 7.828 | SPZ1 | 11.753 | GADD45A | 12.371 |
| STRA8 | 6.437 | SSX4B | 7.872 | RSPO1 | 11.61 | BRF2 | 12.335 |
| RUVBL2 | 6.306 | BATF | 7.423 | POU2AF1 | 11.574 | SRSF8 | 12.248 |
| SPI1 | 6.192 | AATF | 7.284 | BATF | 11.53 | ZBTB33 | 11.879 |
| BATF | 6.14 | GTF3C2 | 7.225 | NKX6-3 | 11.37 | ID1 | 11.878 |
| SRSF8 | 6.139 | ID1 | 7.209 | Contro | 11.23 | ID3 | 11.794 |
| JARID2 | 6.107 | LMO1 | 7.112 | CDYL2 | 11.191 | DEDD2 | 11.208 |
| HDAC8 | 6.076 | RSPO1 | 7.06 | ZFAND3 | 10.849 | PLXNB3 | 11.141 |
| ID3 | 5.878 | FOXM1 | 6.703 | SIRT8 | 10.82 | JARID2 | 11.122 |
| NR3C1 | 5.854 | Contro | 6.752 | MAGI1L3 | 10.781 | FOXN3 | 11.088 |
| SPIB | 5.839 | SIN3A | 6.563 | OLIG1 | 10.54 | AATF | 10.891 |
| SIN3A | 5.834 | JARID2 | 6.47 | FOXN3 | 10.189 | TRPV2 | 10.949 |
| FOXN3 | 5.58 | NR3C1 | 6.386 | NR3C1 | 10.088 | GTF3C2 | 10.946 |
| SETDB1 | 5.553 | KLF9 | 6.338 | BRF2 | 9.963 | VPS72 | 10.842 |
| GLI1 | 5.522 | ZBTB45 | 6.308 | SRSF8 | 9.867 | GTF2F1 | 10.818 |
| ID1 | 5.515 | RFXAP | 6.215 | PA2G4 | 9.78 | LMO1 | 10.778 |

Fig. 4R

| TFs | Endothelial_cells (BM_CD105) | TFs | Bone_marrow (CD34) | TFs | Leukemia_chronic_myelogenous (K562) | TFs | Lymphoma_burkitts_Daudi |
|---|---|---|---|---|---|---|---|
| REST | 21.584 | REST | 19.54 | SIRT8 | 20.321 | SSX6 | 19.95 |
| MYC | 17.373 | SSX8 | 18.77 | MYC | 19.873 | SIRT8 | 19.434 |
| ZNF426 | 17.356 | MYC | 18.125 | REST | 18.499 | ZNF426 | 18.394 |
| SSX6 | 16.554 | ZNF426 | 14.72 | SSX6 | 16.216 | REST | 18.617 |
| SIRT8 | 14.542 | ATF2 | 14.529 | GADD45A | 15.260 | MYC | 18.243 |
| ID1 | 14.357 | SIRT8 | 14.38 | PML | 15.494 | Contro | 17.673 |
| RSPO1 | 13.985 | CDYL2 | 14.299 | TRPV2 | 15.403 | ZBTB45 | 17.542 |
| ATF2 | 13.828 | RSPO1 | 13.831 | BRF2 | 14.324 | HDAC2 | 17.283 |
| CDYL2 | 13.685 | ID1 | 13.654 | ZBTB45 | 14.224 | ZFAND3 | 17.31 |
| RUVBL2 | 13.149 | NR3C1 | 12.695 | RSPO1 | 14.179 | PML | 16.552 |
| AATF | 12.711 | SSX4B | 12.294 | LIN28A | 14.101 | RSPO1 | 16.537 |
| NR3C1 | 12.378 | LMO1 | 12.039 | ZFAND3 | 13.988 | GTF2F1 | 16.259 |
| ZBTB45 | 12.283 | ZSCAN4 | 11.494 | CDYL2 | 13.587 | ATF2 | 16.067 |
| LMO1 | 12.189 | ID3 | 11.217 | ESFLAM | 13.528 | AATF | 15.983 |
| ZFAND3 | 12.163 | RUVBL2 | 11.18 | ZNF426 | 13.274 | LIN28A | 15.812 |
| SRSF8 | 11.881 | PML | 10.929 | SMARCB1 | 13.24 | ZFP57 | 15.328 |
| SIN3A | 11.768 | GTF2F1 | 10.939 | AATF | 13.037 | RFXAP | 15.139 |
| EED | 11.543 | HOPX | 10.927 | NR3C1 | 12.915 | SRSF6 | 14.897 |
| Contro | 11.469 | E2F4 | 10.812 | SUZ12 | 12.866 | SSX4B | 14.794 |
| E2F4 | 11.462 | JARID2 | 10.595 | SRSF6 | 12.744 | NR3C1 | 14.698 |
| PML | 11.39 | STRA8 | 10.537 | FOXN3 | 12.707 | VAX1 | 14.505 |
| GTF2F1 | 11.388 | ZFAND3 | 10.533 | SSX4B | 12.545 | ID1 | 14.241 |
| HOPX | 11.147 | AATF | 10.517 | VAX1 | 12.428 | CRY2 | 14.181 |
| JARID2 | 11.01 | EED | 10.398 | PLXNB3 | 11.754 | SUZ12 | 14.114 |
| GADD45A | 11.026 | ZBTB45 | 10.322 | ATF2 | 11.685 | SMARCB1 | 14.02 |
| DEDD2 | 10.887 | GADD45A | 10.057 | ELL2 | 11.677 | LMO1 | 14.011 |
| SSX4B | 10.753 | PLXNB3 | 10.046 | ID3 | 11.44 | SIN3A | 13.878 |
| HDAC2 | 10.698 | VPS72 | 10.013 | SPZ1 | 11.388 | SPZ1 | 13.583 |
| BRF2 | 10.652 | SRSF8 | 10.013 | ID1 | 11.24 | ID3 | 13.543 |
| RFXAP | 10.498 | BRF2 | 10.004 | Contro | 10.912 | PLXNB3 | 13.488 |

Fig. 4S

| TFs | Leukemia_promyelocytic(hl60) | TFs | Leukemia_lymphoblastic(molt4) | TFs | Testis | TFs | Testis_Leydig_Cell |
|---|---|---|---|---|---|---|---|
| SSX6 | 24.121 | SSX6 | 20.643 | POU2AF1 | 11.382 | MYBL2 | 12.629 |
| MYC | 23.554 | REST | 20.208 | RFX2 | 10.914 | EED | 5.99 |
| SIRT6 | 21.801 | ZNF426 | 18.284 | TGIF1 | 10.18 | TCEA3 | 5.602 |
| REST | 21.449 | SIRT6 | 17.23 | EGFLAM | 10.959 | MYB | 5.518 |
| ZNF426 | 19.947 | GTF2F1 | 16.318 | CTCFL | 9.133 | E2F1 | 5.473 |
| ZFAND3 | 19.201 | RSPO1 | 15.63 | SALL4 | 9.046 | E2F4 | 5.424 |
| RSPO1 | 19.114 | SSX4B | 15.652 | MYBL2 | 8.481 | NR2F2 | 5.306 |
| Cebpb | 18.907 | NR2C1 | 15.598 | DLX6 | 7.541 | ZFAND3 | 5.298 |
| ZBTB45 | 18.728 | ATF2 | 15.093 | HOXA9 | 7.348 | SNAI3 | 5.248 |
| ATF2 | 18.688 | Cebpb | 14.698 | RFX5 | 7.342 | STRA8 | 5.099 |
| HDAC2 | 18.305 | E2F4 | 14.164 | SMAD7 | 7.198 | GTF2F1 | 4.947 |
| PML | 17.775 | ZBTB45 | 14.005 | MYB | 7.186 | STAG1 | 4.946 |
| LIN28A | 17.671 | HOPX | 13.836 | SOX14 | 6.768 | CRY2 | 4.923 |
| SSX4B | 17.581 | HDAC2 | 13.887 | MSX2 | 6.730 | WHSC1 | 4.906 |
| NR2C1 | 17.437 | VPS72 | 13.838 | MAB21L3 | 6.728 | SETDB1 | 4.838 |
| GTF2F1 | 16.34 | JARID2 | 13.841 | SALL1 | 6.685 | NFYB | 4.81 |
| AATF | 16.238 | RUVBL2 | 13.8 | ZNF280B | 6.507 | ZBED4 | 4.684 |
| RFXAP | 15.625 | DEDD2 | 13.578 | SMARCB1 | 6.234 | KDM5A | 4.540 |
| DEDD2 | 15.585 | ID1 | 13.557 | THAP1 | 5.916 | TP53 | 4.387 |
| VAX1 | 15.433 | AATF | 13.528 | ESX1 | 5.898 | SNAI1 | 4.375 |
| BRF2 | 15.43 | VAX1 | 13.381 | RUVBL2 | 5.833 | SIX5 | 4.375 |
| VPS72 | 15.303 | LMO1 | 13.275 | GTF3C2 | 5.707 | SAP30 | 4.378 |
| ID1 | 15.325 | MYC | 13.020 | FOXM1 | 5.686 | RFXAP | 4.124 |
| SRSF8 | 15.042 | RFXAP | 12.698 | ARID3A | 5.518 | RHOXF2 | 4.03 |
| SUZ12 | 15.011 | SMARCB1 | 12.445 | PITX2 | 5.369 | EGR1 | 4.025 |
| ZFP57 | 14.988 | PML | 12.373 | YY1 | 5.331 | SOX11 | 3.977 |
| LMO1 | 14.821 | CDYL2 | 12.386 | ATOH1 | 5.318 | REST | 3.959 |
| FLNB3 | 14.787 | XRCC4 | 12.298 | NKX6-1 | 5.241 | YBX1 | 3.942 |
| JARID2 | 14.794 | ZBTB33 | 12.281 | BACH1 | 4.854 | MSGN1 | 3.880 |
| XRCC4 | 14.585 | ZFAND3 | 12.264 | ID3 | 4.731 | XRCC4 | 3.838 |

Fig. 4T

| TFs | Testis_Germ_Cell | TFs | Testis_Seminiferous_Tubule | TFs | Testis_Interstitial |
|---|---|---|---|---|---|
| MYBL2 | 13.174 | MYBL2 | 12.781 | MYBL2 | 13.584 |
| SNAI1 | 8.762 | E2F4 | 6.871 | E2F4 | 8.09 |
| SNAI3 | 8.074 | SNAI1 | 6.262 | WHSC1 | 7.796 |
| EED | 7.871 | SNAI3 | 6.18 | EED | 7.606 |
| REST | 6.27 | MYB | 6.169 | SNAI3 | 7.08 |
| WHSC1 | 6.203 | GTF2F1 | 5.738 | GTF2F1 | 6.446 |
| MYB | 6.159 | E2F1 | 5.68 | REST | 6.425 |
| L3MBTL2 | 5.598 | REST | 5.61 | MYB | 6.019 |
| STRA8 | 4.916 | WHSC1 | 5.458 | ZFAND3 | 5.962 |
| KDM5A | 4.815 | STRA8 | 5.108 | SNAI1 | 5.944 |
| E2F4 | 4.797 | YBX1 | 4.429 | NR2F2 | 5.792 |
| NR2F2 | 4.757 | ZFAND3 | 4.420 | E2F1 | 5.686 |
| MSGN1 | 4.546 | STAG1 | 4.393 | STRA8 | 5.633 |
| LHX4 | 4.446 | SSX4B | 4.388 | CRY2 | 5.328 |
| MXI1 | 4.409 | NFYB | 4.313 | SSX6 | 5.226 |
| EGR1 | 4.290 | RFXAP | 4.171 | STAG1 | 4.951 |
| ZBED4 | 4.011 | SSX6 | 4.080 | ZBED4 | 4.837 |
| WNT3A | 4.008 | YY1 | 3.983 | RFXAP | 4.565 |
| GATA6 | 3.986 | MSGN1 | 3.883 | SETDB1 | 4.55 |
| TCEA3 | 3.779 | SRSF8 | 3.812 | KDM5A | 4.523 |
| SETDB1 | 3.722 | MSI1 | 3.808 | RXRA | 4.433 |
| CDX2 | 3.718 | CRY2 | 3.801 | ZNF283 | 4.395 |
| PTF1A | 3.679 | HOPX | 3.727 | TCEA3 | 4.283 |
| CRY2 | 3.548 | ZBED4 | 3.723 | HOPX | 4.2 |
| PHOX2B | 3.545 | NEUROD1 | 3.72 | SIX5 | 4.181 |
| FOXS1 | 3.513 | HIST2H3C | 3.708 | SOX15 | 4.098 |
| HOPX | 3.49 | EED | 3.613 | XRCC4 | 4.024 |
| STAG1 | 3.443 | ZFP57 | 3.598 | RHOXF2 | 3.975 |
| SOX11 | 3.393 | SMARCA4 | 3.543 | TP53 | 3.917 |
| SSX6 | 3.373 | ZSCAN4 | 3.481 | HIST2H3C | 3.748 |

Immunohistochemistry with beta-III tubulin (BIII) after 1 week of synthetic mRNA transfection)

BIII
BIII
BIII

Control

1 TF:
NEUROD1

A mixture of 4 TFs:
NEUROD1
NEUROD2
NEUROG2
NEUROG3

METHOD FOR DIFFERENTIATING PLURIPOTENT STEM CELLS INTO DESIRED CELL TYPE

The present application is a divisional of U.S. patent application Ser. No. 17/065,541 filed Oct. 8, 2023, which in turn is a divisional of U.S. patent application Ser. No. 15/555,559, filed Dec. 27, 2017, which is a National Stage Application of PCT/JP2016/057420, filed Mar. 9, 2016, which claims priority from Japanese Patent Application No. 2015-046318, filed Mar. 9, 2015, which is incorporated herein by reference.

REFERENCE TO AN ELECTRONIC SEQUENCE LISTING

The contents of the electronic sequence listing (3190_222_02—sequencelisting.xml; Size: 57,647 bytes; and Date of Creation: Dec. 21, 2123) is herein incorporated by reference in its entirety.

TECHNICAL FIELD

The present invention relates to a method of differentiating a pluripotent stem cell into a desired cell type and a differentiation inducer to be used for the differentiation method.

The present application claims priority from Japanese Patent Application No. 2015-046318, which is incorporated herein by reference.

BACKGROUND ART (Network of Transcription Factors)

A network of transcription factors (TF) can be modified by determining cell identity information and overexpressing a plurality of transcription factors in combination. It is difficult to select a combination of transcription factors that causes specific cell differentiation and prove that the combination causes the differentiation because possible combinations of transcription factors are as many as about 2,000 kinds.

One of the purposes of regenerative medicine is to generate differentiated cells of a desired type from pluripotent stem cells, such as embryonic stem (ES) cells and induced pluripotent stem (iPS) cells {Non Patent Literature 1: Nature 292, 154-156 (1981), Non Patent Literature 2: Proc Natl Acad Sci USA 78, 7634-7638 (1981), Non Patent Literature 3: Science 282, 1145-1147 (1998), Non Patent Literature 4: Cell 126, 663-676 (2006)}.

However, a great number and variety of complicated regulatory mechanisms of transcription factors pose a huge problem on a search for a right combination of transcription factors.

With a view to facilitating transcription factor network analysis, a systems biology approach has been applied {Non Patent Literature 9: Annu Rev Cell Dev Biol 26, 721-744 (2010)} to loss of function, i.e., knockout or suppression of a transcription factor of mouse ES cells {Non Patent Literature 5: Nat Genet 36, 543-544 (2004), Non Patent Literature 6: Nature 442, 533-538 (2006), Non Patent Literature 7: Cell 128, 9-13 (2007), Non Patent Literature 8: Sci Rep 3, 1390 (2013)}, followed by phenotypic analysis or extensive transcriptome analysis.

However, gain of function, i.e., an approach involving overexpression of a transcription factor is more preferred because modification of cell identity information has been able to be considerably achieved as described above by forcible induction of a combination of transcription factors {Non Patent Literature 10: Cell 51, 987-1000 (1987), Non Patent Literature 4: Cell 126, 663-676 (2006), Non Patent Literature 11: Proc Natl Acad Sci USA 105, 6057-6062 (2008), Non Patent Literature 12: Nature 468, 521-526 (2010), Non Patent Literature 13: Nature 463, 1035-1041 (2010), Non Patent Literature 14: Nature 476, 224-227 (2011), Non Patent Literature 15: Cell Stem Cell 9, 205-218 (2011), Non Patent Literature 16: Nature 475, 390-393 (2011), Non Patent Literature 17: Nature 475, 386-389 (2011)}. Therefore, the NIA Mouse ES Cell Bank {Non Patent Literature 18: Cell Stem Cell 5, 420-433 (2009), Non Patent Literature 19: Sci Rep 1, 167 (2011)} has been established. In the NIAMouse ES Cell Bank, 137 kinds of transcription factors, i.e., 7% to 10% of all transcription factors encoded in a mouse genome (1,500 to 2,000 kinds of transcription factors) {Non Patent Literature 20: Biochem Biophys Res Commun 322, 787-793 (2004)} can each be induced by a method capable of tetracycline regulation. After 48 hours from forcibly induced expression of each transcription factor, an extensive gene expression profile (i.e., transcriptome) was measured in each of those ES cell lines {Non Patent Literature 19: Sci Rep 1, 167 (2011)}. Meanwhile, profiles of expression amounts of all genes expressed in various cell species, tissues, and organs are available as public domain databases. One of such databases includes expression profiles of a variety of cell types, provided by the Genomics Institute of the Novartis Research Foundation (GNF) {Non Patent Literature 21: Genome Biol 10, R130 (2009), Non Patent Literature 22: Proc Natl Acad Sci USA 99, 4465-4470 (2002)}. Through comparison between the transcription factor-induced gene expression profiles obtained by the above-mentioned experimentation and the gene expression profiles of the GNF, a matrix for showing correlations of gene expression levels (gene expression correlation matrix) has been created.

(Differentiation of Cell)

It is considered that a differentiation state of a cell is dictated by a set of specific transcription factors expressed in the cell and their expression levels. The transcription factors are factors directly regulating gene expression, and play an important role in forming a cell-specific gene network by binding to transcription regulatory regions, such as promoters and enhancers, to promote or suppress a process of transcribing genetic information of DNA into RNA.

In recent years, research has been actively conducted into development of a technology for inducing differentiation into arbitrary cells using induced pluripotent stem cells (iPS cells). However, there have been problems of low differentiation efficiency and coexistence of different cell lineages. Accordingly, it is an extremely important task to identify transcription factors capable of governing determination of cell differentiation and terminal differentiation.

(Network of Mouse Transcription Factors)

In order to elucidate the structure of a mouse transcription factor network that determines cell differentiation lineages, the inventor of the present invention has established the NIA Mouse ES Cell Bank (cell lines corresponding to 137 transcription factor genes), which allows expression of mouse transcription factor genes to be freely induced {Non Patent Literature 18: Cell Stem Cell 5, 420-433 (2009), Non Patent Literature 19: Sci Rep 1, 167 (2011)}.

In each of those cell lines, a single transcription factor can be forcibly expressed quickly and strongly by removing doxycycline from a culture solution through use of a Tet-off system. The inventor of the present invention has used those cell lines to comprehensively analyze changes in transcript amounts 48 hours after gene expression induction with a microarray. A comparison of the resultant gene expression profile to a gene expression pattern of each mouse organ or tissue (gene expression correlation matrix) has allowed clear observation of what cell lineage tends to be dictated by a change in the gene expression pattern caused by induction of expression of a single transcription factor. With this, it has been confirmed that the direction of cell differentiation to be caused by induction of expression of a transcription factor can be predicted with considerable accuracy.

CITATION LIST

Non Patent Literature

[NPL 1] Nature 292, 154-156 (1981)
[NPL 2] Proc Natl Acad Sci USA 78, 7634-7638 (1981)
[NPL 3] Science 282, 1145-1147 (1998)
[NPL 4] Cell 126, 663-676 (2006)
[NPL 5] Nat Genet 36, 543-544 (2004)
[NPL 6] Nature 442, 533-538 (2006)
[NPL 7] Cell 128, 9-13 (2007)
[NPL 8] Sci Rep 3, 1390 (2013)
[NPL 9] Annu Rev Cell Dev Biol 26, 721-744 (2010)
[NPL 10] Cell 51, 987-1000 (1987)
[NPL 11] Proc Natl Acad Sci USA 105, 6057-6062 (2008)
[NPL 12] Nature 468, 521-526 (2010)
[NPL 13] Nature 463, 1035-1041 (2010)
[NPL 14] Nature 476, 224-227 (2011)
[NPL 15] Cell Stem Cell 9, 205-218 (2011)
[NPL 16] Nature 475, 390-393 (2011)
[NPL 17] Nature 475, 386-389 (2011)
[NPL 18] Cell Stem Cell 5, 420-433 (2009)
[NPL 19] Sci Rep 1, 167 (2011)
[NPL 20] Biochem Biophys Res Commun 322, 787-793 (2004)
[NPL 21] Genome Biol 10, R130 (2009)
[NPL 22] Proc Natl Acad Sci USA 99, 4465-4470 (2002)

SUMMARY OF INVENTION

Technical Problem

It has been confirmed that, through use of a gene expression correlation matrix created using mouse ES cells developed and created by the inventor of the present invention, the direction of cell differentiation to be caused by induction of expression of a transcription factor can be predicted with considerable accuracy. However, it is known that humans and mice, though both are mammals, are significantly different in some respects of cell differentiation.

Solution to Problem

The inventor of the present invention has newly created a human gene expression correlation matrix using human cells, and further, has confirmed that human pluripotent stem cells can be differentiated into a desired cell type by introducing a transcription factor cocktail selected from the matrix into the human pluripotent stem cells. Thus, the present invention has been accomplished.

That is, the present invention includes the following.

1. A method of differentiating a pluripotent stem cell into a neural cell, including a step of introducing a transcription factor including any one of the following (1) to (5) into a pluripotent stem cell of mammalian origin:

(1) five transcription factors selected from NEUROG1, NEUROG2, NEUROG3, NEUROD1, and NEUROD2;
(2) four transcription factors selected from NEUROG1, NEUROG2, NEUROG3, NEUROD1, and NEUROD2;
(3) three transcription factors selected from NEUROG1, NEUROG2, NEUROG3, NEUROD1, and NEUROD2;
(4) two transcription factors selected from NEUROG1, NEUROG2, NEUROG3, NEUROD1, and NEUROD2; and
(5) one transcription factor selected from NEUROG1, NEUROG2, NEUROG3, NEUROD1, and NEUROD2.

2. A method of differentiating a pluripotent stem cell into a neural cell according to the above-mentioned item 1, in which the neural cell includes a motor nerve.

3. A method of differentiating a pluripotent stem cell into a neural cell according to the above-mentioned item 1 or 2, in which the motor nerve is a cell present in a motor nerve.

4. A neural cell differentiation inducer, which is capable of differentiating a pluripotent stem cell of mammalian origin into a neural cell, the neural cell differentiation inducer including a transcription factor including any one of the following (1) to (5):

(1) five transcription factors selected from NEUROG1, NEUROG2, NEUROG3, NEUROD1, and NEUROD2;
(2) four transcription factors selected from NEUROG1, NEUROG2, NEUROG3, NEUROD1, and NEUROD2;
(3) three transcription factors selected from NEUROG1, NEUROG2, NEUROG3, NEUROD1, and NEUROD2;
(4) two transcription factors selected from NEUROG1, NEUROG2, NEUROG3, NEUROD1, and NEUROD2; and
(5) one transcription factor selected from NEUROG1, NEUROG2, NEUROG3, NEUROD1, and NEUROD2.

5. A differentiation inducer according to the above-mentioned item 4, in which the neural cell is a peripheral motor nerve.

6. A differentiation inducer according to the above-mentioned item 4 or 5, in which the motor nerve is a cell present in a motor nerve.

7. A differentiation inducer according to any one of the above-mentioned items 4 to 6, in which the transcription factor is mRNA, synthetic mRNA, a nucleic acid, or a protein.

8. A method of differentiating a pluripotent stem cell into a hepatoblast and/or a liver cell, including a step of introducing a transcription factor including any one of the following (1) to (5) into a pluripotent stem cell of mammalian origin:

(1) one transcription factor selected from TGIF, TCF4, PITX2, SALL4, and MEIS1;
(2) two transcription factors selected from TGIF, TCF4, PITX2, SALL4, and MEIS1;
(3) three transcription factors selected from TGIF, TCF4, PITX2, SALL4, and MEIS1;
(4) four transcription factors selected from TGIF, TCF4, PITX2, SALL4, and MEIS1; and
(5) five transcription factors selected from TGIF, TCF4, PITX2, SALL4, and MEIS1.

9. A hepatoblast and/or liver cell differentiation inducer, which is capable of differentiating a pluripotent stem cell of mammalian origin into a hepatoblast and/or a liver cell, the hepatoblast and/or liver cell differentiation inducer including a transcription factor including any one of the following (1) to (5):

(1) one transcription factor selected from TGIF, TCF4, PITX2, SALL4, and MEIS1;

(2) two transcription factors selected from TGIF, TCF4, PITX2, SALL4, and MEIS1;

(3) three transcription factors selected from TGIF, TCF4, PITX2, SALL4, and MEIS1;

(4) four transcription factors selected from TGIF, TCF4, PITX2, SALL4, and MEIS1; and (5) five transcription factors selected from TGIF, TCF4, PITX2, SALL4, and MEIS1.

10. A method of differentiating a pluripotent stem cell into a hematopoietic stem cell and/or a blood cell, including a step of introducing a transcription factor including any one of the following (1) to (7) into a pluripotent stem cell of mammalian origin:

(1) one transcription factor selected from CDYL2, ETS2, SPI1, OVOL2, CDX2, CEBPB, and SALL4;

(2) two transcription factors selected from CDYL2, ETS2, SPI1, OVOL2, CDX2, CEBPB, and SALL4;

(3) three transcription factors selected from CDYL2, ETS2, SPI1, OVOL2, CDX2, CEBPB, and SALL4;

(4) four transcription factors selected from CDYL2, ETS2, SPI1, OVOL2, CDX2, CEBPB, and SALL4;

(5) five transcription factors selected from CDYL2, ETS2, SPI1, OVOL2, CDX2, CEBPB, and SALL4;

(6) six transcription factors selected from CDYL2, ETS2, SPI1, OVOL2, CDX2, CEBPB, and SALL4; and (7) seven transcription factors selected from CDYL2, ETS2, SPI1, OVOL2, CDX2, CEBPB, and SALL4.

11. A hematopoietic stem cell and/or blood cell differentiation inducer, which is capable of differentiating a pluripotent stem cell of mammalian origin into a hematopoietic stem cell and/or a blood cell, the hematopoietic stem cell and/or blood cell differentiation inducer including a transcription factor including any one of the following (1) to (7):

(1) one transcription factor selected from CDYL2, ETS2, SPI1, OVOL2, CDX2, CEBPB, and SALL4;

(2) two transcription factors selected from CDYL2, ETS2, SPI1, OVOL2, CDX2, CEBPB, and SALL4;

(3) three transcription factors selected from CDYL2, ETS2, SPI1, OVOL2, CDX2, CEBPB, and SALL4;

(4) four transcription factors selected from CDYL2, ETS2, SPI1, OVOL2, CDX2, CEBPB, and SALL4;

(5) five transcription factors selected from CDYL2, ETS2, SPI1, OVOL2, CDX2, CEBPB, and SALL4;

(6) six transcription factors selected from CDYL2, ETS2, SPI1, OVOL2, CDX2, CEBPB, and SALL4; and (7) seven transcription factors selected from CDYL2, ETS2, SPI1, OVOL2, CDX2, CEBPB, and SALL4.

12. A method of differentiating a pluripotent stem cell into a chondrocyte, including a step of introducing a transcription factor SOX9 into a pluripotent stem cell of mammalian origin.

13. A chondrocyte differentiation inducer, which is capable of differentiating a pluripotent stem cell of mammalian origin into a chondrocyte, the chondrocyte differentiation inducer including a transcription factor SOX9.

14. A method of differentiating a pluripotent stem cell into a neural cell, including a step of introducing a transcription factor including any one of the following (1) to (11) into a pluripotent stem cell of mammalian origin:

(1) one transcription factor selected from NEUROG2, NEUROG3, NEUROG1, NEUROD1, NRF1, HOXA2, ASCL1, PITX2, NEUROD2, PRDM1, and NFIB;

(2) NEUROG2 and one or more transcription factors selected from NEUROG3, NEUROG1, NEUROD1, NRF1, HOXA2, ASCL1, PITX2, NEUROD2, PRDM1, and NFIB;

(3) NEUROG2, NEUROG3, and one or more transcription factors selected from NEUROG1, NEUROD1, NRF1, HOXA2, ASCL1, PITX2, NEUROD2, PRDM1, and NFIB;

(4) NEUROG2, NEUROG3, NEUROG1, and one or more transcription factors selected from NEUROD1, NRF1, HOXA2, ASCL1, PITX2, NEUROD2, PRDM1, and NFIB;

(5) NEUROG2, NEUROG3, NEUROG1, NEUROD1, and one or more transcription factors selected from NRF1, HOXA2, ASCL1, PITX2, NEUROD2, PRDM1, and NFIB;

(6) NEUROG2, NEUROG3, NEUROG1, NEUROD1, NRF1, and one or more transcription factors selected from HOXA2, ASCL1, PITX2, NEUROD2, PRDM1, and NFIB;

(7) NEUROG2, NEUROG3, NEUROG1, NEUROD1, NRF1, HOXA2, and one or more transcription factors selected from ASCL1, PITX2, NEUROD2, PRDM1, and NFIB;

(8) NEUROG2, NEUROG3, NEUROG1, NEUROD1, NRF1, HOXA2, ASCL1, and one or more transcription factors selected from PITX2, NEUROD2, PRDM1, and NFIB;

(9) NEUROG2, NEUROG3, NEUROG1, NEUROD1, NRF1, HOXA2, ASCL1, PITX2, and one or more transcription factors selected from NEUROD2, PRDM1, and NFIB;

(10) NEUROG2, NEUROG3, NEUROG1, NEUROD1, NRF1, HOXA2, ASCL1, PITX2, NEUROD2, and one or more transcription factors selected from PRDM1 and NFIB;

(11) transcription factors of NEUROG2, NEUROG3, NEUROG1, NEUROD1, NRF1, HOXA2, ASCL1, PITX2, NEUROD2, PRDM1, and NFIB.

15. A method of differentiating a pluripotent stem cell into a neural cell according to the above-mentioned item 14, further including introducing one or more transcription factors selected from TCF4, PDX1, SMAD7, SOX11, RNF2, MXI1, and YY1 into a human pluripotent stem cell.

16. A method of differentiating a pluripotent stem cell into a neural cell according to the above-mentioned item 14 or 15, in which the neural cell is a cell present in a neural cell.

17. A neural cell differentiation inducer, which is capable of differentiating a pluripotent stem cell of mammalian origin into a neural cell, the neural cell differentiation inducer including a transcription factor including any one of the following (1) to (11):

(1) one transcription factor selected from NEUROG2, NEUROG3, NEUROG1, NEUROD1, NRF1, HOXA2, ASCL1, PITX2, NEUROD2, PRDM1, and NFIB;

(2) NEUROG2 and one or more transcription factors selected from NEUROG3, NEUROG1, NEUROD1, NRF1, HOXA2, ASCL1, PITX2, NEUROD2, PRDM1, and NFIB;

(3) NEUROG2, NEUROG3, and one or more transcription factors selected from NEUROG1, NEUROD1, NRF1, HOXA2, ASCL1, PITX2, NEUROD2, PRDM1, and NFIB;

(4) NEUROG2, NEUROG3, NEUROG1, and one or more transcription factors selected from NEUROD1, NRF1, HOXA2, ASCL1, PITX2, NEUROD2, PRDM1, and NFIB;

(5) NEUROG2, NEUROG3, NEUROG1, NEUROD1, and one or more transcription factors selected from NRF1, HOXA2, ASCL1, PITX2, NEUROD2, PRDM1, and NFIB;

(6) NEUROG2, NEUROG3, NEUROG1, NEUROD1, NRF1, and one or more transcription factors selected from HOXA2, ASCL1, PITX2, NEUROD2, PRDM1, and NFIB;

(7) NEUROG2, NEUROG3, NEUROG1, NEUROD1, NRF1, HOXA2, and one or more transcription factors selected from ASCL1, PITX2, NEUROD2, PRDM1, and NFIB;

(8) NEUROG2, NEUROG3, NEUROG1, NEUROD1, NRF1, HOXA2, ASCL1, and one or more transcription factors selected from PITX2, NEUROD2, PRDM1, and NFIB;

(9) NEUROG2, NEUROG3, NEUROG1, NEUROD1, NRF1, HOXA2, ASCL1, PITX2, and one or more transcription factors selected from NEUROD2, PRDM1, and NFIB;

(10) NEUROG2, NEUROG3, NEUROG1, NEUROD1, NRF1, HOXA2, ASCL1, PITX2, NEUROD2, and one or more transcription factors selected from PRDM1 and NFIB; and

(11) transcription factors of NEUROG2, NEUROG3, NEUROG1, NEUROD1, NRF1, HOXA2, ASCL1, PITX2, NEUROD2, PRDM1, and NFIB.

18. A neural cell differentiation inducer according to the above-mentioned item 17, further including one or more transcription factors selected from TCF4, PDX1, SMAD7, SOX11, RNF2, MXI1, and YY1.

19. A neural cell differentiation inducer according to the above-mentioned item 17 or 18, in which the neural cell is a cell present in a neural cell.

Advantageous Effects of Invention

The method of differentiating a pluripotent stem cell into a desired cell type of the present invention can differentiate pluripotent stem cells into desired cell types.

BRIEF DESCRIPTION OF DRAWINGS

FIG. 4A is the human gene expression correlation matrix created in Example 1 (expressed in Z-values).

FIG. 4B is the human gene expression correlation matrix created in Example 1 (expressed in Z-values).

FIG. 4C is the human gene expression correlation matrix created in Example 1 (expressed in Z-values).

FIG. 4D is the human gene expression correlation matrix created in Example 1 (expressed in Z-values).

FIG. 4E is the human gene expression correlation matrix created in Example 1 (expressed in Z-values).

FIG. 4F is the human gene expression correlation matrix created in Example 1 (expressed in Z-values).

FIG. 4G is the human gene expression correlation matrix created in Example 1 (expressed in Z-values).

FIG. 4H is the human gene expression correlation matrix created in Example 1 (expressed in Z-values).

FIG. 4I is the human gene expression correlation matrix created in Example 1 (expressed in Z-values).

FIG. 4J is the human gene expression correlation matrix created in Example 1 (expressed in Z-values).

FIG. 4K is the human gene expression correlation matrix created in Example 1 (expressed in Z-values).

FIG. 4L is the human gene expression correlation matrix created in Example 1 (expressed in Z-values).

FIG. 4M is the human gene expression correlation matrix created in Example 1 (expressed in Z-values).

FIG. 4N is the human gene expression correlation matrix created in Example 1 (expressed in Z-values).

FIG. 4O is the human gene expression correlation matrix created in Example 1 (expressed in Z-values).

FIG. 4P is the human gene expression correlation matrix created in Example 1 (expressed in Z-values).

FIG. 4Q is the human gene expression correlation matrix created in Example 1 (expressed in Z-values).

FIG. 4R is the human gene expression correlation matrix created in Example 1 (expressed in Z-values).

FIG. 4S is the human gene expression correlation matrix created in Example 1 (expressed in Z-values).

FIG. 4T is the human gene expression correlation matrix created in Example 1 (expressed in Z-values).

Figure 1:
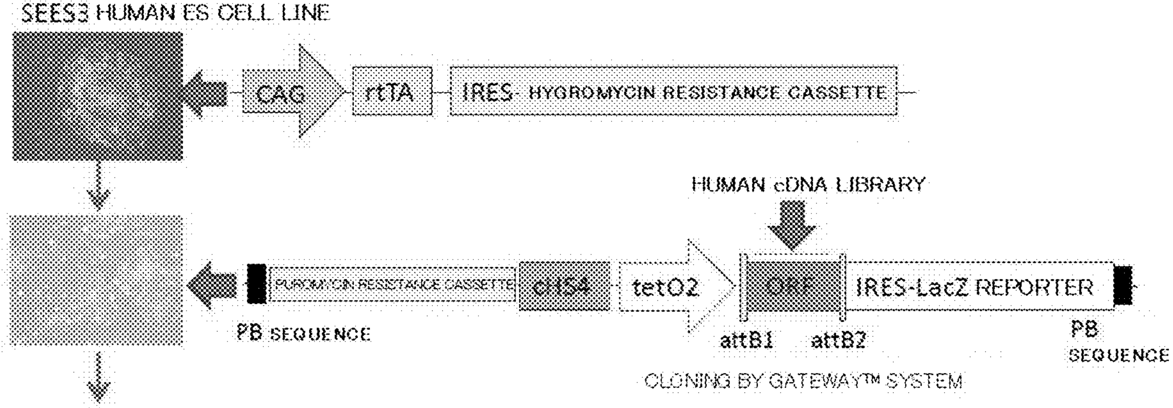
FIG. 1 is an illustration of a human ES cell line expressing a specific transcription factor gene.

DESCRIPTION OF EMBODIMENTS (Method of Differentiating Pluripotent Stem Cell into Desired Cell Type of the Present Invention)

A method of differentiating a pluripotent stem cell into a desired cell type of the present invention (hereinafter sometimes referred to as "method of the present invention") includes introducing, into a pluripotent stem cell, a transcription factor or a transcription factor cocktail required for differentiation into a desired cell type, to differentiate the pluripotent stem cell into any one or more cell types among tissues, organs, and cells (horizontal axis) shown in a human gene expression correlation matrix created in Example 1 of the present invention. The method of the present invention is described below.

The term "gene" as used herein encompasses not only double-stranded nucleic acids, but also their respective constituent single strands, such as plus strands (or sense strands) or complementary strands (or antisense strands), linear nucleic acids, and cyclic nucleic acids, and encompasses DNA, RNA, mRNA, cDNA, and the like, unless otherwise stated.

The method of the present invention includes the steps of: selecting at least one kind of positive transcription factor having a z-value of 3 or more for a specific cell type from a matrix shown in FIGS. 3A-3D; and introducing a nucleic acid or mRNA encoding the at least one kind of positive transcription factor, or a protein thereof, or all of the foregoing into a pluripotent stem cell to form a transformed cell or the specific cell type.

A step required for differentiating the transformed cell into the specific cell type may include specific treatment {e.g., culture under a specific environment (culture conditions)} as well as further introduction of another transcription factor.

Further, the method of the present invention may additionally or alternatively include the steps of: selecting at least one kind of negative transcription factor (cold color) from the matrix shown in FIGS. 3A-3D; and introducing a nucleic acid or mRNA encoding the at least one kind of negative transcription factor, or a protein thereof, or both of the foregoing into the pluripotent stem cell to form the transformed cell or the specific cell type. Further, in the method of the present invention, the expression of a transcription factor may be reduced, and a transcription factor gene may be knocked out as well. In order to reduce the expression of, or knock out, the transcription factor, any desirable method may be utilized, and examples thereof include RNA interference, targeted ribozyme, homologous recombination, site-directed mutagenesis, methylation, and any combination thereof.

(z-Value)

z-Values shown in FIGS. 4A-4T of the present invention may be determined by, for example, the following equation (1) disclosed in the literature "Sci Rep 1, 167 (2011)."

$$z=(x\text{set}-x\text{all})\times\sqrt{n\text{set}}/SD\text{all} \quad (1)$$

In the equation, xset represents the average expression change in a specific subset of genes, xall represents the average expression change in all genes, nset represents the size of the gene set, and SDall represents standard deviation of expression change among all genes. xall may be the number of the most upregulated genes, the number of the most downregulated genes, or the total sum of the numbers of the most upregulated genes and the most downregulated genes. The total sum may be a total number equal to, or more than or less than about 100, about 500, about 1,000, about 2,500, about 4,000, about 5,000, about 6,000, about 7,500, about 10,000. nset may be 10, 25, 40, 50, 60, 75, 100, 250, 500, or 1,000 or more genes.

A desirable number of positive and/or negative transcription factors may be selected from the matrix, and for example, 1, 2, 3, 4, 5, 6, 7, 8, 9, 10, 11, 12, 13, 14, 15, 16, 17, 18, 19, 20, 25, or more transcription factors may be selected and used. At least one kind out of the positive transcription factors preferably has a z-value of 3 or more for the specific cell type. Any other positive transcription factor may have a z-value of 3 or more or less than 3. The z-value of each positive transcription factor, or the average z-value of the group of the positive transcription factors may be set to 0 or more, or 1, 2, 3, 4, 5, 6, 7, 8, 9, 10, 11, 12, 13, 14, 15, 16, 17, 18, 19, 20, 25, 30, 40, or 50 or more.

At least one kind out of the negative transcription factors preferably has a z-value of an integer less than or equal to −3 for the specific cell type. Any other negative transcription factor may have a z-value of −3 or less or more. The z-value of each negative transcription factor, or the average z-value of the group of the negative transcription factors may be set to less than 0, or −1, −2, −3, −4, −5, −6, −7, −8, −9, −10, −11, −12, −13, −14, −15, −20, −25, −30, −40, or −50 or less.

(Transcription Factor)

The form of each of the transcription factors to be used in the method of the present invention is not particularly limited, and examples thereof may include, but not particularly limited to, nucleic acids, synthetic mRNAs, and proteins.

Further, a vector for introducing each of the transcription factors into the pluripotent stem cell is not particularly limited, and may be, for example, a viral vector, such as a Sendai virus vector. And, nanoparticle capsules, liposomes, exosomes, or the like containing synthetic mRNAs or proteins may also be used to introduce the transcription factors into the pluripotent stem cell.

In addition, the transcription factors to be used herein may be exemplified by the following:

DLX3 (distal-less homeobox 3), NEUROG3 (neurogenin 3), NEUROG2 (neurogenin 2), NEUROG1 (neurogenin 1), ASCL1 (achaete-scute family bHLH transcription factor 1), NEUROD1 (neurogenic differentiation 1), YY1 (YY1 transcription factor), SOX11 (SRY (sex determining region Y)-box 11), GLIS2 (GLIS family zinc finger 2), PDX1 (pancreatic and duodenal homeobox 1), E2F6 (E2F transcription factor 6), SOX2 (SRY (sex determining region Y)-box 2), CDX2 (caudal type homeobox 2), DLX4 (distal-less homeobox 4), NANOG (Nanog homeobox), MXI1 (MAX interactor 1, dimerization protein), RNF2 (ring finger protein 2), NEUROD2 (neurogenic differentiation 2), ASCL2 (achaete-scute family bHLH transcription factor 2), SREBF2 (sterol regulatory element binding transcription factor 2), SOX15 (SRY (sex determining region Y)-box 15), FOXA2 (forkhead box A2), FOXA1 (forkhead box A1), TBX3 (T-box 3), ARNT2 (aryl-hydrocarbon receptor nuclear translocator 2), PITX2 (paired-like homeodomain 2), PRDM1 (PR domain containing 1, with ZNF domain), TCF4 (transcription factor 4), NFIB (nuclear factor I/B), ZNF281 (zinc finger protein 281), TBX2 (T-box 2), NR2F2 (nuclear receptor subfamily 2, group F, member 2), NFIC {nuclear factor I/C (CCAAT-binding transcription factor)}, NRF1 (nuclear respiratory factor 1), HOXA2 (homeobox A2), TBX5 (T-box 5), ZIC1 (Zic family member 1), HEY1 (hes-related family bHLH transcription factor with YRPW motif 1), CTCF {CCCTC-binding factor (zinc finger protein)}, HES1 (hes family bHLH transcription factor 1), TFAP2C {transcription factor AP-2 gamma (activating enhancer binding protein 2 gamma)}, MYOD1 (myogenic differentiation 1), SALL4 (spalt-like transcription factor 4), TP73 (tumor protein p73), TFE3 (transcription factor binding to IGHM enhancer 3), FOXP1 (forkhead box P1), FOS (FBJ murine osteosarcoma viral oncogene homolog), IRF4 (interferon regulatory factor 4), GATA3 (GATA binding protein 3), JUNB (jun B proto-oncogene), ESX1 (ESX homeobox 1), TGIF1 (TGFB-induced factor homeobox 1), MAB21L3 (mab-21-like 3), DLX6 (distal-less homeobox 6), IRF5 (interferon regulatory factor 5), HSF1 (heat shock transcription factor 1), JUN (jun proto-oncogene), FOSL1 (FOS-like antigen 1), CTCFL {CCCTC-binding factor (zinc finger protein)-like}, FOSL2 (FOS-like antigen 2), FOXG1 (forkhead box G1), THAP11 (THAP domain containing 11), CUX1 (cut-like homeobox 1), ESRRB (estrogen-related receptor beta), HNF4A (hepatocyte nuclear factor 4, alpha), HNF1A (HNF1 homeobox A), NKX2-5 (NK2 homeobox 5), KLF9 (Kruppel-like factor 9), TFAP4 {transcription factor AP-4 (activating enhancer binding protein 4)}, ERG (v-ets avian erythroblastosis virus E26 oncogene homolog), KLF3 (Kruppel-like factor 3), MKRN1 (makorin ring finger protein 1), OLIG2 (oligodendrocyte lineage transcription factor 2), ELF5 {E74-like factor 5 (ets domain transcription factor)}, HOXA9 (homeobox A9), NKX2-1 (NK2 homeobox 1), GRHL2 {grainyhead-like 2 (*Drosophila*)}, USF2 (upstream transcription factor 2, c-fos interacting), KLF4 {Kruppel-like factor 4 (gut)}, ELF1 {E74-like factor 1 (ets domain transcription factor)}, CEBPB {CCAAT/enhancer binding protein (C/EBP), beta}, ETS1 (v-ets avian erythroblastosis virus E26 oncogene homolog 1), ETS2 (v-ets avian erythroblastosis virus E26 oncogene homolog 2), SPI1 (Spi-1 proto-oncogene), IRF1 (interferon regulatory factor 1), IRF2 (interferon regulatory factor 2), DMRT1 (doublesex and mab-3 related transcription factor 1), GLI1 (GLI family zinc finger 1), SPIC {Spi-C transcription factor (Spi-1/PU.1 related)}, RUNX3 (runt-related transcription factor 3), GATA2 (GATA binding protein 2), MEF2C (myocyte enhancer factor 2C), FOXL2 (forkhead box L2), FBXO15 (F-box protein 15), HHEX (hematopoietically expressed homeobox), SMAD7 (SMAD family member 7), MEIS2 (Meis homeobox2), ARID3A {AT rich interactive domain 3A (BRIGHT-like)}, WRNIP1 (Werner helicase interacting protein 1), PPARG (peroxisome proliferator-activated receptor gamma), PTF1A (pancreas specific transcription factor, la), RFX2 {regulatory factor X, 2 (influences HLA class II expression)}, EOMES (eomesodermin), TFCP2L1 (transcription factor CP2-like 1), ZNF274 (zinc finger protein 274), EGR1 (early growth response 1), LHX2 (LIM homeobox 2), TFAP2A {transcription factor AP-2 alpha (activating enhancer binding protein 2 alpha)}, OTX1 (orthodenticle homeobox 1), OVOL2 (ovo-like zinc finger 2), E2F4 (E2F transcription factor 4, p107/p130-binding), RUVBL2 (RuvB-like AAA ATPase 2), SMARCA4 (SWI/SNF related, matrix associated, actin dependent regulator of chromatin, subfamily a, member 4), GTF2F1 (general transcription factor IIF, polypeptide 1, 74 kDa), GBX2 (gastrulation brain homeobox 2), ID1 (inhibitor of DNA binding 1, dominant negative helix-loop-helix protein), PLXNB3 (plexin B3), MYC (v-myc avian myelocytomatosis viral oncogene homolog), ATF2 (activating transcription factor 2), CDYL2 (chromodomain protein, Y-like 2), ZBTB45 (zinc finger and BTB domain containing 45), RSPO1 (R-spondin 1), STAT5A (signal transducer and activator of transcription 5A), LMO1 {LIM domain only 1 (rhombotin 1)}, SMARCB1 (SWI/SNF related, matrix associated, actin dependent regulator of chromatin, subfamily b, member 1), GADD45A (growth arrest and DNA-damage-inducible, alpha), SETDB1 (SET domain, bifurcated 1), SRSF6 (serine/arginine-rich splicing factor 6), ZFAND3 (zinc finger, AN1-type domain 3), IRF3 (interferon regulatory factor 3), KAT8 {K (lysine) acetyltransferase 8}, ZSCAN4 (zinc finger and SCAN domain containing 4), CRY1 {cryptochrome 1 (photolyase-like)}, SIN3A (SIN3 transcription regulator family member A), LMO2 {LIM domain only 2 (rhombotin-like 1)}, NFYB (nuclear transcription factor Y, beta), L3MBTL2 {1 (3)mbt-like 2 (*Drosophila*)}, TP53 (tumor protein p53), RHOXF2 (Rhox homeobox family, member 2), RFX5 {regulatory factor X, 5 (influences HLA class II), EGFLAM (EGF-like, fibronectin type III and laminin G domains), NELFE (negative elongation factor complex member E), XRCC4 (X-ray repair complementing defective repair in Chinese hamster cells 4), ZFP57 (ZFP57 zinc finger protein), SAP30 (Sin3A-associated protein, 30 kDa), Emerald (A virant form of green fluorescence protein [GFP]), BCL6 (B-cell CLL/lymphoma 6), RXRA (retinoid X receptor, alpha), STAT3 {signal transducer and activator of transcription 3 (acute-phase response factor)}, ELL2 (elongation factor, RNA polymerase II, 2), TRPV2 (transient receptor potential cation channel, subfamily V, member 2), HOXC9 (homeobox C9), RARA (retinoic acid receptor, alpha), ZNF263 (zinc finger protein 263), SMAD5 (SMAD family member 5), SUB1 {SUB1 homolog (*S. cerevisiae*)}, SUZ12 (SUZ12 polycomb repressive complex 2 subunit), JAG1 (jagged 1), ATF3 (activating transcription factor 3), ATF1 (activating transcription factor 1), FLI1 (Fli-1 proto-oncogene, ETS transcription factor), ETV5 (ets variant 5), KDM5A {lysine (K)-specific demethylase 5A}, NELFA (negative elongation factor complex member A), TCF23 (transcription factor 23), ZNF646 (zinc finger protein 646), SIX5 (SIX homeobox 5), MYBL2 (v-myb avian myeloblastosis viral oncogene homolog-like 2), PAX6 (paired box 6), SMAD2 (SMAD family member 2), SOX9 {SRY (sex determining region Y)-box 9}, STRA13 (stimulated by retinoic acid 13), TBX6 (T-box 6), SMAD1 (SMAD family member 1), FOXH1 (forkhead box H1), OTX2 (orthodenticle homeobox 2), TGIF (TGFB induced factor homeobox 1), and MEIS1 (Meis homeobox 1).

(Pluripotent Stem Cell)

The pluripotent stem cell to be used in the method of the present invention is of mammalian origin, particularly preferably of human origin. The pluripotent stem cell is, for example, a human ES cell, a human iPS cell, or any combination thereof, but is not particularly limited, and encompasses tissue stem cells derived from tissues and organs, dermal fibroblasts, and all kinds of cells derived from tissues and organs.

(ES Cell Line into which Transcription Factor Gene is Introduced)

In the steps of the method of the present invention, a method known per se may be used as a method of introducing each transcription factor gene into the pluripotent stem cell without any particular limitation. However, there may be preferably used an expression cassette inserted between PiggyBac transposase recognition sequences (PB sequences) developed by Woltjen et al. (reference: Nature 458: 766-770, 2009), which is a mechanism by which a gene to be introduced is actively incorporated into a human ES cell genome. The expression cassette is a system capable of efficiently establishing a genetically modified human ES cell line by introducing a drug selection cassette (see FIG. 1).

(Method for Induction into Desired Cell Type)

Figure 2:
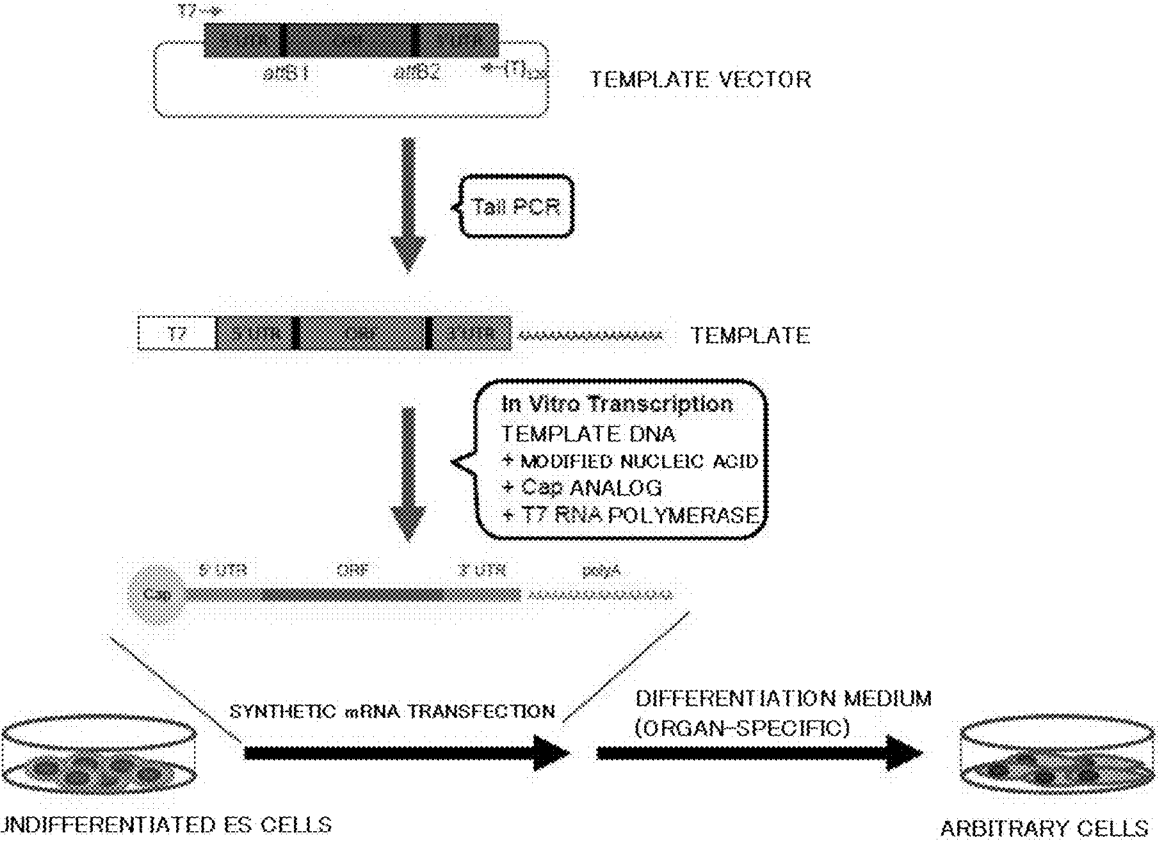
FIG. 2 is an illustration of a method of inducing differentiation into a desired cell type.
Figure 3A:
FIG. 3A is a human gene expression correlation matrix created in Example 1.
Figure 3B:
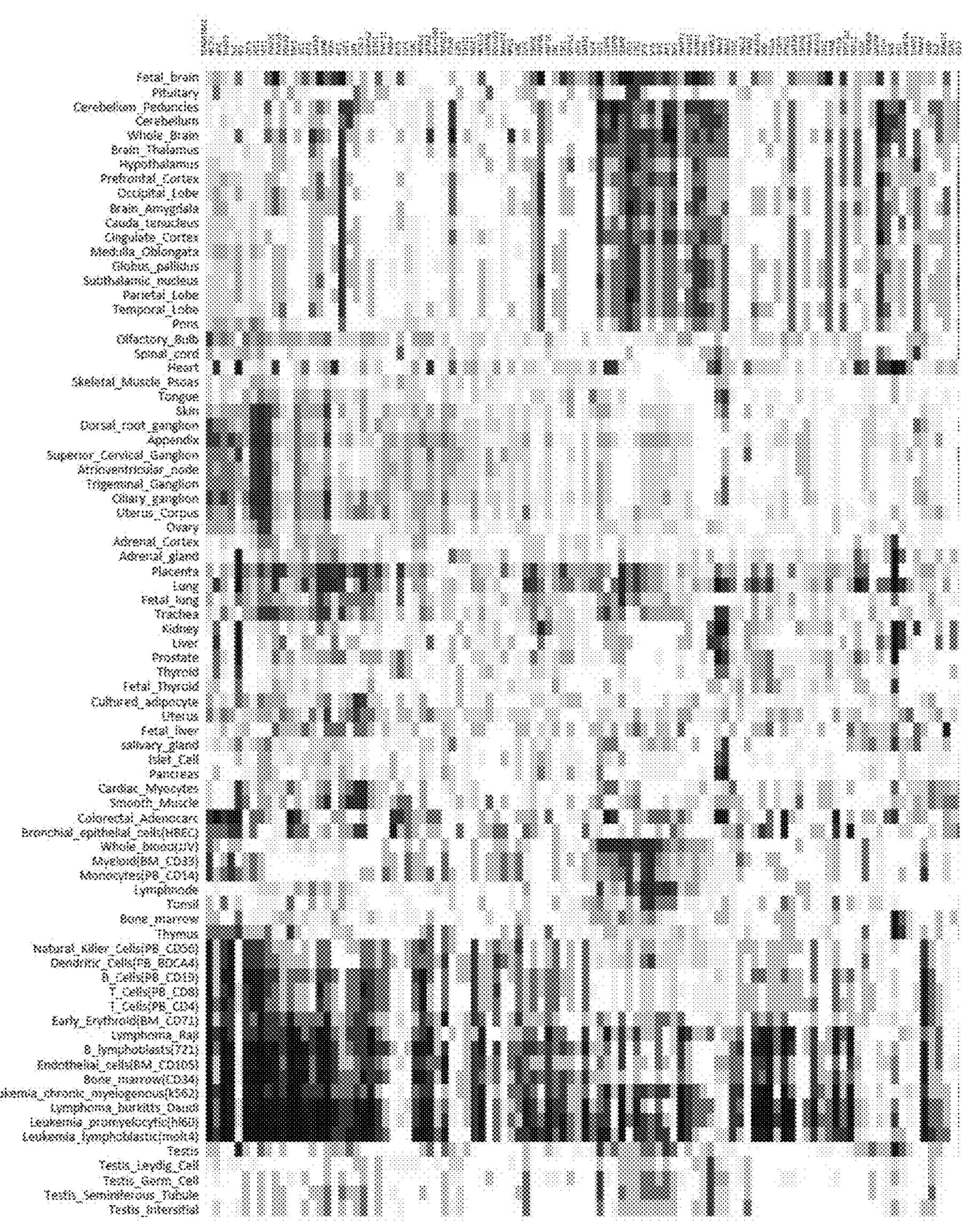
FIG. 3B is the human gene expression correlation matrix created in Example 1.
Figure 3C:
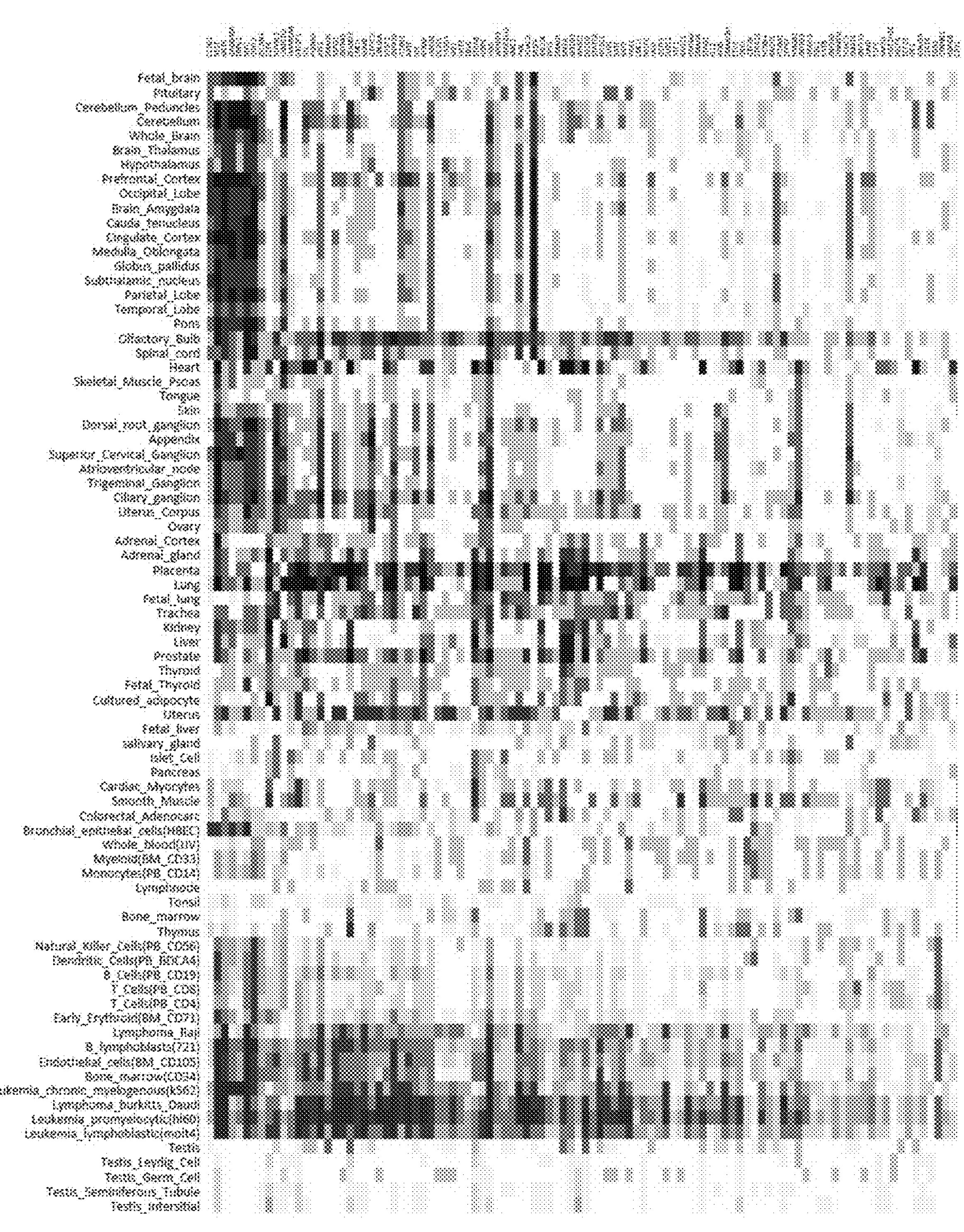
FIG. 3C is the human gene expression correlation matrix created in Example 1.
Figure 3D:
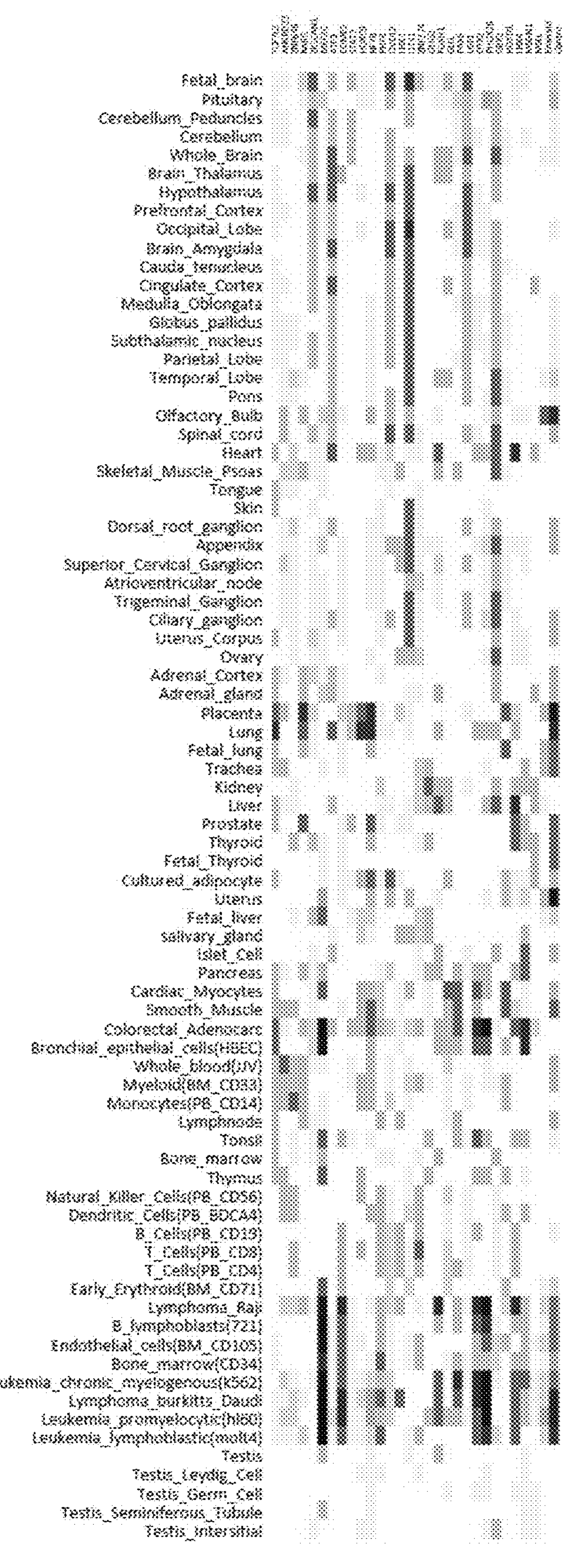
FIG. 3D is the human gene expression correlation matrix created in Example 1.

In the steps of the method of the present invention, a method known per se may be used as a method for induction into the desired cell type without any particular limitation. However, there is preferably used a method of inducing differentiation by efficiently introducing transcription factor gene synthetic mRNA into human pluripotent stem cells through use of a gene expression method involving using synthetic mRNA developed by Warren, Rossi, et al. (reference: Cell Stem Cell 7: 618-630, 2010), which is a footprint-free forced gene expression method causing no gene incorporation into a host genome (see FIG. 2).

(Method of Utilizing Human Gene Expression Correlation Matrix)

The inventor of the present invention has already created a mouse gene expression correlation matrix and confirmed that the direction of cell differentiation to be caused by induction of expression of a transcription factor can be predicted with considerable accuracy. However, it is known that humans and mice, though both are mammals, are significantly different in some respects of cell differentiation. Further, the inventor of the present invention has newly created a human gene expression correlation matrix through use of human pluripotent stem cells and combinations of human transcription factors. Comparing the human gene expression correlation matrix disclosed for the first time in the present invention and the previously reported mouse gene expression correlation matrix, it has been confirmed that: in mice and humans, transcription factors and combinations of transcription factors required for differentiation into desired cell types are more significantly different than expected; and human cells have higher differentiation speeds than mouse cells.

Besides, the human gene expression correlation matrix of the present invention (see FIGS. 3A-3D and FIGS. 4A-4T) also includes desired organs, tissues, and cells that are not described in the mouse gene expression correlation matrix.

In the gene expression correlation matrix developed and created by the inventor of the present invention, when a transcription factor having a Z-value equal to or higher than a certain value (cut-off value, for example, 7 or more) and/or transcription factors having the top three or more Z-values are selected and introduced into mammalian pluripotent stem cells, the mammalian pluripotent stem cells can be induced into a desired cell type. Examples include the following.

For differentiation into skeletal muscles serving as the desired cell type, Myod1, Mef2c, and Esx1 were selected from transcription factors each having a Z-value of 11 or more in the gene expression correlation matrix and were each introduced alone into mouse ES cells, and as a result, it was confirmed that the mouse ES cells differentiated into skeletal muscles.

For differentiation into liver cells serving as the desired cell type, Hnf4a, Foxa1, Gata2, and Gata3 were selected from transcription factors each having a Z-value of 10 or more in the gene expression correlation matrix and were each introduced alone into mouse ES cells, and as a result, it was confirmed that the mouse ES cells were able to be differentiated into liver cells.

For differentiation into blood cells serving as the desired cell type, Sfpi1, Elf1, Elf5, Myc, Irf2, and Ets1 were selected from transcription factors each having a Z-value of 15 or more in the gene expression correlation matrix and were each introduced alone into mouse ES cells, and as a result, it was confirmed that the mouse ES cells were able to be differentiated into blood cells.

For differentiation into nerve cells serving as the desired cell type, Ascl1, Smad7, Nr2f1, Sox11, Dmrt1, Sox9, Foxg1, and Sox2 were selected from transcription factors each having a Z-value of 12 or more in the gene expression correlation matrix and were each introduced alone into mouse ES cells, and as a result, it was confirmed that the mouse ES cells were able to be differentiated into nerve cells.

In Examples of the present invention, NEUROD1, NEUROD2, NEUROG2, and NEUROG3, which are transcription factors each having a Z-value of 8 or more in the gene expression correlation matrix, were introduced into human embryonic stem cells, and as a result, it was confirmed that the human embryonic stem cells were able to be differentiated into nerve cells.

In Examples of the present invention, NEUROD1 (having a base sequence set forth in SEQ ID NO: 1, and an amino acid sequence set forth in SEQ ID NO: 2), NEUROD2 (having a base sequence set forth in SEQ ID NO: 3, and an amino acid sequence set forth in SEQ ID NO: 4), NEUROG1 (having a base sequence set forth in SEQ ID NO: 5, and an amino acid sequence set forth in SEQ ID NO: 6), NEUROG2 (having abase sequence set forth in SEQ ID NO: 7, and an amino acid sequence set forth in SEQ ID NO: 8), and NEUROG3 (having a base sequence set forth in SEQ ID NO: 9, and an amino acid sequence set forth in SEQ ID NO: 10) were introduced into human embryonic stem cells, and as a result, it was confirmed that the human embryonic stem cells were able to be differentiated into motor cells.

In Examples of the present invention, any one or more of TGIF (which may be any of homeobox protein TGIF1 isoforms a to e, and has, for example, a base sequence set forth in SEQ ID NO: 11, and an amino acid sequence set forth in SEQ ID NO: 12), TCF4 (which may be any of transcription factor 4 isoforms a to n, and has, for example, a base sequence set forth in SEQ ID NO: 13, and an amino acid sequence set forth in SEQ ID NO: 14), PITX2 (which may be any of pituitary homeobox 2 isoforms a to c, and has, for example, a base sequence set forth in SEQ ID NO: 15, and an amino acid sequence set forth in SEQ ID NO: 16), SALL4 (which may be any of sal-like protein 4 isoforms 1 and 2, and has, for example, a base sequence set forth in SEQ ID NO: 17, and an amino acid sequence set forth in SEQ ID NO: 18), and MEIS1 (which has, for example, a base sequence set forth in SEQ ID NO: 19, and an amino acid sequence set forth in SEQ ID NO: 20) were introduced into human embryonic stem cells, and as a result, it was confirmed that the human embryonic stem cells were able to be differentiated into liver cells (hepatoblasts). These transcription factors are completely different from transcription factors (Hnf4a and Foxa1) used in differentiation of mouse ES cells into liver cells.

In Examples of the present invention, any one or more of CDYL2 (which has, for example, a base sequence set forth in SEQ ID NO: 21, and an amino acid sequence set forth in SEQ ID NO: 22), ETS2 (which may be any of transcriptional regulator ERG isoforms 1 to 7, and has, for example, a base sequence set forth in SEQ ID NO: 23, and an amino acid sequence set forth in SEQ ID NO: 24), SPI1 (which may be any of transcription factor PU.1 isoforms 1 and 2, and has, for example, a base sequence set forth in SEQ ID NO: 25, and an amino acid sequence set forth in SEQ ID NO: 26), OVOL2 (which may be any of transcription factor Ovo-like 2 isoforms 1 and 2, and has, for example, abase sequence set forth in SEQ ID NO: 27, and an amino acid sequence set forth in SEQ ID NO: 28), CDX2 (which has, for example, a base sequence set forth in SEQ ID NO: 29, and an amino acid sequence set forth in SEQ ID NO: 30), and CEBPB (which may be any of CCAAT/enhancer-binding protein beta isoforms a to c, and has, for example, a base sequence set forth in SEQ ID NO: 31, and an amino acid sequence set forth in SEQ ID NO: 32) were introduced into human embryonic stem cells, and as a result, it was confirmed that the human embryonic stem cells were able to be differentiated into blood cells (or hematopoietic stem cells).

In Examples of the present invention, SOX9 (which has, for example, a base sequence set forth in SEQ ID NO: 33, and an amino acid sequence set forth in SEQ ID NO: 34) was introduced into human embryonic stem cells, and as a result, it was confirmed that the human embryonic stem cells were able to be differentiated into chondrocytes.

As can be seen from the above, when transcription factors each having a Z-value of 6 or more (or 7 or more, 8 or more, 9 or more, 10 or more, 11 or more, or 12 or more) and/or the top three (or four, five, six, seven, eight, nine, or ten) transcription factors having the highest Z-values in the human gene expression correlation matrix of the present invention are selected and introduced alone or in combination thereof into a human pluripotent stem cell, the human pluripotent stem cell can be induced into a desired cell type. Now, specific examples of the method of the present invention are described.

(Method for Differentiation into Nerve Cell)

A method for differentiation into a nerve cell (in particular, a cell present in the fetal brain, the cerebellum peduncles, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons) of the present invention is as described below.

Fetal brain: A single transcription factor, or two or more transcription factors selected from transcription factors shown in FIG. 4A (Fetal_brain) are introduced into a human pluripotent stem cell. Further, as necessary, one or more transcription factors, which are shown in the gene expression correlation matrix other than the foregoing, are simultaneously introduced into the human pluripotent stem cell.

Cerebellum peduncles: A single transcription factor, or two or more transcription factors selected from transcription factors shown in FIG. 4A (Cerebellum_Peduncles) are introduced into a human pluripotent stem cell. Further, as necessary, one or more transcription factors, which are shown in the gene expression correlation matrix other than the foregoing, are simultaneously introduced into the human pluripotent stem cell.

Cerebellum: A single transcription factor, or two or more transcription factors selected from transcription factors shown in FIG. 4A (Cerebellum) are introduced into a human pluripotent stem cell. Further, as necessary, one or more transcription factors, which are shown in the gene expression correlation matrix other than the foregoing, are simultaneously introduced into the human pluripotent stem cell.

Whole brain: A single transcription factor, or two or more transcription factors selected from transcription factors shown in FIG. 4B (Whole_Brain) are introduced into a human pluripotent stem cell. Further, as necessary, one or more transcription factors, which are shown in the gene expression correlation matrix other than the foregoing, are simultaneously introduced into the human pluripotent stem cell.

Brain thalamus: A single transcription factor, or two or more transcription factors selected from transcription factors shown in FIG. 4B (Brain_Thalamus) are introduced into a human pluripotent stem cell. Further, as necessary, one or more transcription factors, which are shown in the gene expression correlation matrix other than the foregoing, are simultaneously introduced into the human pluripotent stem cell.

Hypothalamus: A single transcription factor, or two or more transcription factors selected from transcription factors shown in FIG. 4B (Hypothalamus) are introduced into a human pluripotent stem cell. Further, as necessary, one or more transcription factors, which are shown in the gene expression correlation matrix other than the foregoing, are simultaneously introduced into the human pluripotent stem cell.

Prefrontal cortex: A single transcription factor, or two or more transcription factors selected from transcription factors shown in FIG. 4B (Prefrontal_Cortex) are introduced into a human pluripotent stem cell. Further, as necessary, one or more transcription factors, which are shown in the gene expression correlation matrix other than the foregoing, are simultaneously introduced into the human pluripotent stem cell.

Occipital lobe: A single transcription factor, or two or more transcription factors selected from transcription factors shown in FIG. 4C (Occipital_Lobe) are introduced into a human pluripotent stem cell. Further, as necessary, one or more transcription factors, which are shown in the gene expression correlation matrix other than the foregoing, are simultaneously introduced into the human pluripotent stem cell.

Brain amygdala: A single transcription factor, or two or more transcription factors selected from transcription factors shown in FIG. 4C (Brain_Amygdala) are introduced into a human pluripotent stem cell. Further, as necessary, one or more transcription factors, which are shown in the gene expression correlation matrix other than the foregoing, are simultaneously introduced into the human pluripotent stem cell.

Caudate nucleus: A single transcription factor, or two or more transcription factors selected from transcription factors shown in FIG. 4C (Caudate_nucleus) are introduced into a human pluripotent stem cell. Further, as necessary, one or more transcription factors, which are shown in the gene expression correlation matrix other than the foregoing, are simultaneously introduced into the human pluripotent stem cell.

Cingulate cortex: A single transcription factor, or two or more transcription factors selected from transcription factors shown in FIG. 4C (Cingulate_Cortex) are introduced into a human pluripotent stem cell. Further, as necessary, one or more transcription factors, which are shown in the gene expression correlation matrix other than the foregoing, are simultaneously introduced into the human pluripotent stem cell.

Medulla oblongata: A single transcription factor, or two or more transcription factors selected from transcription factors shown in FIG. 4D (Medulla_Oblongata) are introduced into a human pluripotent stem cell. Further, as necessary, one or more transcription factors, which are shown in the gene expression correlation matrix other than the foregoing, are simultaneously introduced into the human pluripotent stem cell.

Globus pallidus: A single transcription factor, or two or more transcription factors selected from transcription factors shown in FIG. 4D (Globus_pallidus) are introduced into a human pluripotent stem cell. Further, as necessary, one or more transcription factors, which are shown in the gene expression correlation matrix other than the foregoing, are simultaneously introduced into the human pluripotent stem cell.

Subthalamic nucleus: A single transcription factor, or two or more transcription factors selected from transcription factors shown in FIG. 4D (Subthalamic nucleus) are introduced into a human pluripotent stem cell. Further, as necessary, one or more transcription factors, which are shown in the gene expression correlation matrix other than the foregoing, are simultaneously introduced into the human pluripotent stem cell.

Parietal lobe: A single transcription factor, or two or more transcription factors selected from transcription factors shown in FIG. 4D (Parietal_Lobe) are introduced into a human pluripotent stem cell. Further, as necessary, one or more transcription factors, which are shown in the gene expression correlation matrix other than the foregoing, are simultaneously introduced into the human pluripotent stem cell.

Temporal lobe: A single transcription factor, or two or more transcription factors selected from transcription factors shown in FIG. 4E (Temporal_Lobe) are introduced into a human pluripotent stem cell. Further, as necessary, one or more transcription factors, which are shown in the gene expression correlation matrix other than the foregoing, are simultaneously introduced into the human pluripotent stem cell.

Pons: A single transcription factor, or two or more transcription factors selected from transcription factors shown in FIG. 4E (Pons) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Pituitary (in Particular, Cell Present in Pituitary)}

A method for differentiation into the pituitary of the present invention is as described below.

A single transcription factor, or two or more transcription factors selected from transcription factors shown in FIG. 4A (Pituitary) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Olfactory Nerve (in Particular, Cell Present in Olfactory Nerve)}

A method for differentiation into the olfactory nerve (in particular, the olfactory bulb) of the present invention is as described below.

Olfactory bulb: A single transcription factor, or two or more transcription factors selected from transcription factors shown in FIG. 4E (Olfactory_Bulb) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Spinal Nerve (in particular, Cell present in Spinal Nerve)}A method for differentiation into the spinal nerve (in particular, the spinal cord) of the present invention is as described below.

Spinal cord: A single transcription factor, or two or more transcription factors selected from transcription factors shown in FIG. 4E (Spinal_cord) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Skeletal Muscle (in Particular, Cell Present in Skeletal Muscle)}

A method for differentiation into askeletal muscle (in particular, the psoas or the tongue) of the present invention is as described below.

Psoas: A single transcription factor, or two or more transcription factors selected from transcription factors shown in FIG. 4F (Skeletal_Muscle_Psoas) are introduced into a human pluripotent stem cell. Further, as necessary, one or more transcription factors, which are shown in the gene expression correlation matrix other than the foregoing, are simultaneously introduced into the human pluripotent stem cell.

Tongue: A single transcription factor, or two or more transcription factors selected from transcription factors shown in FIG. 4F (Tongue) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Skin (in Particular, Cell Present in Skin)}

A method for differentiation into the skin of the present invention is as described below.

A single transcription factor, or two or more transcription factors selected from transcription factors shown in FIG. 4F (Skin) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Ganglion (in Particular, Cell Present in Ganglion)}

A method for differentiation into a ganglion (in particular, the dorsal root ganglion, the superior cervical ganglion, the atrioventricular node, the trigeminal ganglion, or the ciliary ganglion) of the present invention is as described below.

Dorsal root ganglion: A single transcription factor, or two or more transcription factors selected from transcription factors shown in FIG. 4G (Dorsal_root_ganglion) are introduced into a human pluripotent stem cell. Further, as necessary, one or more transcription factors, which are shown in the gene expression correlation matrix other than the foregoing, are simultaneously introduced into the human pluripotent stem cell.

Superior cervical ganglion: A single transcription factor, or two or more transcription factors selected from transcription factors shown in FIG. 4G (Superior_Cervical_Ganglion) are introduced into a human pluripotent stem cell. Further, as necessary, one or more transcription factors, which are shown in the gene expression correlation matrix other than the foregoing, are simultaneously introduced into the human pluripotent stem cell.

Atrioventricular node: A single transcription factor, or two or more transcription factors selected from transcription factors shown in FIG. 4G (Atrioventricular node) are introduced into a human pluripotent stem cell. Further, as necessary, one or more transcription factors, which are shown in the gene expression correlation matrix other than the foregoing, are simultaneously introduced into the human pluripotent stem cell.

Trigeminal ganglion: A single transcription factor, or two or more transcription factors selected from transcription factors shown in FIG. 4H (Trigeminal_Ganglion) are introduced into a human pluripotent stem cell. Further, as necessary, one or more transcription factors, which are shown in the gene expression correlation matrix other than the foregoing, are simultaneously introduced into the human pluripotent stem cell.

Ciliary ganglion: A single transcription factor, or two or more transcription factors selected from transcription factors shown in FIG. 4H (Ciliary_ganglion) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Ovary (in Particular, Cell Present in Ovary)}

A method for differentiation into the ovary of the present invention is as described below.

A single transcription factor, or two or more transcription factors selected from transcription factors shown in FIG. 4H (Ovary) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Adrenal Gland (in Particular, Cell Present in Adrenal Gland)}

A method for differentiation into the adrenal gland (in particular, the adrenal cortex or the adrenal gland) of the present invention is as described below.

Adrenal cortex: A single transcription factor, or two or more transcription factors selected from transcription factors shown in FIG. 4I (Adrenal_Cortex) are introduced into a human pluripotent stem cell. Further, as necessary, one or more transcription factors, which are shown in the gene expression correlation matrix other than the foregoing, are simultaneously introduced into the human pluripotent stem cell.

Adrenal gland: A single transcription factor, or two or more transcription factors selected from transcription factors shown in FIG. 4I (Adrenal_gland) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Appendix (in Particular, Cell Present in Appendix)}

A method for differentiation into the appendix of the present invention is as described below.

A single transcription factor, or two or more transcription factors selected from transcription factors shown in FIG. 4G (Appendix) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Kidney (in Particular, Cell Present in Kidney)}

A method for differentiation into the kidney of the present invention is as described below.

A single transcription factor, or two or more transcription factors selected from transcription factors shown in FIG. 4J (Kidney) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Liver (in Particular, Cell Present in Liver)}

A method for differentiation into the liver (in particular, the liver or the fetal liver) of the present invention is as described below.

Liver: A single transcription factor, or two or more transcription factors selected from transcription factors shown in FIG. 4J (Liver) are introduced into a human pluripotent stem cell. Further, as necessary, one or more transcription factors, which are shown in the gene expression correlation matrix other than the foregoing, are simultaneously introduced into the human pluripotent stem cell.

Fetal liver: A single transcription factor, or two or more transcription factors selected from transcription factors shown in FIG. 4L (Fetal_liver) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Salivary Gland (in Particular, Cell Present in Salivary Gland)}

A method for differentiation into the salivary gland of the present invention is as described below.

A single transcription factor, or two or more transcription factors selected from transcription factors shown in FIG. 4L (salivary_gland) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Islet (in Particular, Cell Present in Islet)}

A method for differentiation into the islet (in particular, an islet cell) of the present invention is as described below.

A single transcription factor, or two or more transcription factors selected from transcription factors shown in FIG. 4L (Islet_Cell) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Pancreas (in Particular, Cell Present in Pancreas)}

A method for differentiation into the pancreas of the present invention is as described below.

A single transcription factor, or two or more transcription factors selected from transcription factors shown in FIG. 4M (Pancreas) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Prostate (in Particular, Cell Present in Prostate)}

A method for differentiation into the prostate of the present invention is as described below.

A single transcription factor, or two or more transcription factors selected from transcription factors shown in FIG. 4K (Prostate) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Thyroid (in Particular, Cell Present in Thyroid)}

A method for differentiation into the thyroid (in particular, the thyroid or the fetal thyroid) of the present invention is as described below.

Thyroid: A single transcription factor, or two or more transcription factors selected from transcription factors shown in FIG. 4K (Thyroid) are introduced into a human pluripotent stem cell. Further, as necessary, one or more transcription factors, which are shown in the gene expression correlation matrix other than the foregoing, are simultaneously introduced into the human pluripotent stem cell.

Fetal thyroid: A single transcription factor, or two or more transcription factors selected from transcription factors shown in FIG. 4K (Fetal_Thyroid) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Adipocyte)

A method for differentiation into an adipocyte (in particular, a cultured adipocyte) of the present invention is as described below.

Cultured adipocyte: A single transcription factor, or two or more transcription factors selected from transcription factors shown in FIG. 4K (Cultured_adipocyte) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Uterus (in Particular, Cell Present in Uterus)}

A method for differentiation into the uterus (in particular, the uterus or the uterus corpus) of the present invention is as described below.

Uterus: A single transcription factor, or two or more transcription factors selected from transcription factors shown in FIG. 4L (Uterus) are introduced into a human pluripotent stem cell. Further, as necessary, one or more transcription factors, which are shown in the gene expression correlation matrix other than the foregoing, are simultaneously introduced into the human pluripotent stem cell.

Uterus corpus: A single transcription factor, or two or more transcription factors selected from transcription factors shown in FIG. 4H (Uterus_Corpus) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Blood Cell)

A method for differentiation into a blood cell (in particular, whole blood, the bone marrow, a monocyte, a lymphnode, the tonsil, the thymus, a natural killer cell, a dendritic cell, a B cell, a B lymphoblast, a T cell (PB_CD8 or PB_CD4), or an early erythroid) of the present invention is as described below.

Whole blood: A single transcription factor, or two or more transcription factors selected from transcription factors shown in FIG. 4N (Whole_blood (JJV)) are introduced into a human pluripotent stem cell. Further, as necessary, one or more transcription factors, which are shown in the gene expression correlation matrix other than the foregoing, are simultaneously introduced into the human pluripotent stem cell.

Bone marrow: A single transcription factor, or two or more transcription factors selected from transcription factors shown in FIG. 4N (Myeloid (BM_CD33)) are introduced into a human pluripotent stem cell. Further, as necessary, one or more transcription factors, which are shown in the gene expression correlation matrix other than the foregoing, are simultaneously introduced into the human pluripotent stem cell.

Monocyte: A single transcription factor, or two or more transcription factors selected from transcription factors shown in FIG. 4N (Monocytes (PB_CD14)) are introduced into a human pluripotent stem cell. Further, as necessary, one or more transcription factors, which are shown in the gene expression correlation matrix other than the foregoing, are simultaneously introduced into the human pluripotent stem cell.

Lymphnode: A single transcription factor, or two or more transcription factors selected from transcription factors shown in FIG. 4O (Lymphnode) are introduced into a human pluripotent stem cell. Further, as necessary, one or more transcription factors, which are shown in the gene expression correlation matrix other than the foregoing, are simultaneously introduced into the human pluripotent stem cell.

Tonsil: A single transcription factor, or two or more transcription factors selected from transcription factors shown in FIG. 4O (Tonsil) are introduced into a human pluripotent stem cell. Further, as necessary, one or more transcription factors, which are shown in the gene expression correlation matrix other than the foregoing, are simultaneously introduced into the human pluripotent stem cell.

Thymus: A single transcription factor, or two or more transcription factors selected from transcription factors shown in FIG. 4O (Thymus) are introduced into a human pluripotent stem cell. Further, as necessary, one or more transcription factors, which are shown in the gene expression correlation matrix other than the foregoing, are simultaneously introduced into the human pluripotent stem cell.

Natural killer cell: A single transcription factor, or two or more transcription factors selected from transcription factors shown in FIG. 4P (Natural_Killer_Cells (PB_CD56)) are introduced into a human pluripotent stem cell. Further, as necessary, one or more transcription factors, which are shown in the gene expression correlation matrix other than the foregoing, are simultaneously introduced into the human pluripotent stem cell.

Dendritic cell: A single transcription factor, or two or more transcription factors selected from transcription factors shown in FIG. 4P (Dendritic_Cells (PB_BDCA4)) are introduced into a human pluripotent stem cell. Further, as necessary, one or more transcription factors, which are shown in the gene expression correlation matrix other than the foregoing, are simultaneously introduced into the human pluripotent stem cell.

B cell: A single transcription factor, or two or more transcription factors selected from transcription factors shown in FIG. 4P (B_Cells (PB_CD19)) are introduced into a human pluripotent stem cell. Further, as necessary, one or more transcription factors, which are shown in the gene expression correlation matrix other than the foregoing, are simultaneously introduced into the human pluripotent stem cell.

B lymphoblast: A single transcription factor, or two or more transcription factors selected from transcription factors shown in FIG. 4Q (B_lymphoblasts (721)) are introduced into a human pluripotent stem cell. Further, as necessary, one or more transcription factors, which are shown in the gene expression correlation matrix other than the foregoing, are simultaneously introduced into the human pluripotent stem cell.

T cell (PB_CD8): A single transcription factor, or two or more transcription factors selected from transcription factors shown in FIG. 4P (T Cells (PB_CD8)) are introduced into a human pluripotent stem cell. Further, as necessary, one or more transcription factors, which are shown in the gene expression correlation matrix other than the foregoing, are simultaneously introduced into the human pluripotent stem cell.

T cell (PB_CD4): A single transcription factor, or two or more transcription factors selected from transcription factors shown in FIG. 4Q (T_Cells (PB_CD4)) are introduced into a human pluripotent stem cell. Further, as necessary, one or more transcription factors, which are shown in the gene expression correlation matrix other than the foregoing, are simultaneously introduced into the human pluripotent stem cell.

Early erythroid: A single transcription factor, or two or more transcription factors selected from transcription factors shown in FIG. 4Q (Early Erythroid (BM CD71)) are introduced into a human pluripotent stem cell. Further, as necessary, one or more transcription factors, which are shown in the gene expression correlation matrix other than the foregoing, are simultaneously introduced into the human pluripotent stem cell.

Lymphoma-derived Raji cell: A single transcription factor, or two or more transcription factors selected from transcription factors shown in FIG. 4Q (Lymphoma_Raji) are introduced into a human pluripotent stem cell. Further, as necessary, one or more transcription factors, which are shown in the gene expression correlation matrix other than the foregoing, are simultaneously introduced into the human pluripotent stem cell.

Chronic myelogenous leukemia cell: A single transcription factor, or two or more transcription factors selected from transcription factors shown in FIG. 4R (Leukemia_chronic_myelogenous (k562)) are introduced into a human pluripotent stem cell. Further, as necessary, one or more transcription factors, which are shown in the gene expression correlation matrix other than the foregoing, are simultaneously introduced into the human pluripotent stem cell.

Burkitt's lymphoma Daudi cell line: A single transcription factor, or two or more transcription factors selected from transcription factors shown in FIG. 4R (Lymphoma_burkitts_Daudi) are introduced into a human pluripotent stem cell. Further, as necessary, one or more transcription factors, which are shown in the gene expression correlation matrix other than the foregoing, are simultaneously introduced into the human pluripotent stem cell.

Promyelocytic leukemia cell: A single transcription factor, or two or more transcription factors selected from transcription factors shown in FIG. 4S (Leukemia_promyelocytic (hl60)) are introduced into a human pluripotent stem cell. Further, as necessary, one or more transcription factors, which are shown in the gene expression correlation matrix other than the foregoing, are simultaneously introduced into the human pluripotent stem cell.

Lymphoblastic leukemia cell: A single transcription factor, or two or more transcription factors selected from transcription factors shown in FIG. 4S (Leukemia_lymphoblastic (molt4)) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Bone Marrow (Cell Present in Bone Marrow)}

A method for differentiation into the bone marrow of the present invention is as described below.

A single transcription factor, or two or more transcription factors selected from transcription factors shown in FIG. 4O (Bone_marrow) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Hematopoietic Stem Cell)

A method for differentiation into a hematopoietic stem cell of the present invention is as described below.

A single transcription factor, or two or more transcription factors selected from transcription factors shown in FIG. 4R (Bone_marrow (CD34)) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Vascular Endothelial Cell)

A method for differentiation into a vascular endothelial cell of the present invention is as described below.

A single transcription factor, or two or more transcription factors selected from transcription factors shown in FIG. 4R (Endothelial_cells (BM_CD105)) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Testis (in Particular, Cell Present in Testis)}

A method for differentiation into the testis (in particular, the testis, a testis Leydig cell, a testis germ cell, the testis seminiferous tubule, or a testis interstitial cell) of the present invention is as described below.

Testis: A single transcription factor, or two or more transcription factors selected from transcription factors shown in FIG. 4S (Testis) are introduced into a human pluripotent stem cell. Further, as necessary, one or more transcription factors, which are shown in the gene expression correlation matrix other than the foregoing, are simultaneously introduced into the human pluripotent stem cell.

Testis Leydig cell: A single transcription factor, or two or more transcription factors selected from transcription factors shown in FIG. 4S (Testis Leydig Cell) are introduced into a human pluripotent stem cell. Further, as necessary, one or more transcription factors, which are shown in the gene expression correlation matrix other than the foregoing, are simultaneously introduced into the human pluripotent stem cell.

Testis germ cell: A single transcription factor, or two or more transcription factors selected from transcription factors shown in FIG. 4T (Testis_Germ_Cell) are introduced into a human pluripotent stem cell. Further, as necessary, one or more transcription factors, which are shown in the gene expression correlation matrix other than the foregoing, are simultaneously introduced into the human pluripotent stem cell.

Testis seminiferous tubule: A single transcription factor, or two or more transcription factors selected from transcription factors shown in FIG. 4T (Testis_Seminiferous_Tubule) are introduced into a human pluripotent stem cell. Further, as necessary, one or more transcription factors, which are shown in the gene expression correlation matrix other than the foregoing, are simultaneously introduced into the human pluripotent stem cell.

Testis interstitial cell: A single transcription factor, or two or more transcription factors selected from transcription factors shown in FIG. 4T (Testis_Interstitial) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Heart (in Particular, Cell Present in Heart)}

A method for differentiation into the heart (in particular, the heart or a cardiac myocyte) of the present invention is as described below.

Heart: A single transcription factor, or two or more transcription factors selected from transcription factors shown in FIG. 4F (Heart) are introduced into a human pluripotent stem cell. Further, as necessary, one or more transcription factors, which are shown in the gene expression correlation matrix other than the foregoing, are simultaneously introduced into the human pluripotent stem cell.

Cardiac myocyte: A single transcription factor, or two or more transcription factors selected from transcription factors shown in FIG. 4M (Cardiac_Myocytes) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Placenta (in Particular, Cell Present in Placenta)}

A method for differentiation into the placenta of the present invention is as described below.

A single transcription factor, or two or more transcription factors selected from transcription factors shown in FIG. 4I (Placenta) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Smooth Muscle (in Particular, Cell Present in Smooth Muscle)}

A method for differentiation into a smooth muscle of the present invention is as described below.

A single transcription factor, or two or more transcription factors selected from transcription factors shown in FIG. 4M (Smooth_Muscle) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Lung (in Particular, Cell Present in Lung)}

A method for differentiation into the lung (in particular, the lung, a bronchial epithelial cell, the fetal lung, or the trachea) of the present invention is as described below.

Lung: A single transcription factor, or two or more transcription factors selected from transcription factors shown in FIG. 4I (Lung) are introduced into a human pluripotent stem cell. Further, as necessary, one or more transcription factors, which are shown in the gene expression correlation matrix other than the foregoing, are simultaneously introduced into the human pluripotent stem cell.

Bronchial epithelial cell: A single transcription factor, or two or more transcription factors selected from transcription factors shown in FIG. 4N (Bronchial_epithelial_cells (HBEC)) are introduced into a human pluripotent stem cell. Further, as necessary, one or more transcription factors, which are shown in the gene expression correlation matrix other than the foregoing, are simultaneously introduced into the human pluripotent stem cell.

Fetal lung: A single transcription factor, or two or more transcription factors selected from transcription factors shown in FIG. 4J (Fetal_lung) are introduced into a human pluripotent stem cell. Further, as necessary, one or more transcription factors, which are shown in the gene expression correlation matrix other than the foregoing, are simultaneously introduced into the human pluripotent stem cell.

Trachea: A single transcription factor, or two or more transcription factors selected from transcription factors shown in FIG. 4J (Trachea) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Colorectal Adenocarcinoma Cell)

A method for differentiation into a colorectal adenocarcinoma cell of the present invention is as described below.

Colorectal adenocarcinoma cell: A single transcription factor, or two or more transcription factors selected from transcription factors shown in FIG. 4M (Colorectal_Adenocarcinoma) are introduced into a human pluripotent stem cell. Further, as necessary, one or more transcription factors, which are shown in the gene expression correlation matrix other than the foregoing, are simultaneously introduced into the human pluripotent stem cell.

(Differentiation Inducer to be Used for Method of Differentiating Pluripotent Stem Cell into Desired Cell Type)

A differentiation inducer to be used for the method of differentiating a pluripotent stem cell into a desired cell type of the present invention (hereinafter sometimes referred to as "differentiation inducer of the present invention") is a composition including at least a transcription factor required for the method of the present invention.

Specifically, the differentiation inducer of the present invention includes a transcription factor in any of, for example, the following forms: nucleic acids, synthetic mRNAs, proteins, and viral vectors carrying the foregoing, nanoparticle capsules carrying the foregoing, liposomes carrying the foregoing, or Exosome carrying the foregoing.

The transcription factor in the form of a protein included in the differentiation inducer of the present invention may be exemplified by the following:

(1) a transcription factor, or a protected derivative, sugar chain-modified product, acylated derivative, or acetylated derivative of the transcription factor;

(2) a transcription factor that has 90% (or 92%, 94%, 96%, 98%, or 99%) or more homology to the above-mentioned transcription factor and has a peculiar transcription factor action substantially equivalent to that of the transcription factor; and (3) a transcription factor that has 100 to 10, 50 to 30, 40 to 20, 10 to 5, or 5 to 1 amino acid substituted, deleted, inserted, and/or added in the transcription factor as described in any one of the above-mentioned items and has a peculiar transcription factor action substantially equivalent to that of the transcription factor.

The transcription factor in the form of mRNA, synthetic mRNA, or a nucleic acid included in the differentiation inducer of the present invention may be exemplified by the following:

(4) a gene encoding a polypeptide formed of the transcription factor of any one or more of the above-mentioned items;

(5) a gene encoding a polypeptide that has 1 to 20 (or 1 to 15, 1 to 10, 1 to 7, 1 to 5, or 1 to 3) amino acids substituted, deleted, inserted, and/or added in the amino acid sequence of the transcription factor of any one or more of the above-mentioned items and has a peculiar transcription factor action substantially equivalent to that of the transcription factor;

(6) a gene encoding a polypeptide that has 90% (or 92%, 94%, 96%, 98%, or 99%) or more homology to the amino acid sequence of the transcription factor of any one or more of the above-mentioned items and has a peculiar transcription factor action substantially equivalent to that of the transcription factor; and (7) a gene encoding a polypeptide that has 90% (or 92%, 94%, 96%, 98%, or 99%) or more homology to the base sequence of the transcription factor of any one or more of the above-mentioned items and has a peculiar transcription factor action substantially equivalent to that of the transcription factor.

A transcription factor having a mutation may be a naturally occurring one, or may be one obtained by introducing a mutation on the basis of a gene of natural origin. Means for introducing a mutation is known per se, and for example, a site-directed mutagenesis method, a homologous gene recombination method, a primer extension method, a polymerase chain reaction (hereinafter abbreviated as PCR), and the like may be used alone or in combination thereof as appropriate.

The method may be performed in conformity with any of methods disclosed in the literatures ("Molecular Cloning: A Laboratory Manual, second edition" edited by Sambrook et al., 1989, Cold Spring Harbor Laboratory; and "Lab Manual: Genetic Engineering" edited by Masami Muramatsu, 1988, Maruzen), or by modifying these methods, and Ulmer's technology (Ulmer, K. M., "Science", 1983, volume 219, p. 666-671) may also be utilized. In the case of a peptide, from the viewpoint of preventing alteration of basic properties of the peptide (e.g., physical properties, function, physiological activity, or immunological activity) in the introduction of a mutation, for example, mutual substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable.

Examples of the differentiation inducer of the present invention are listed below.

Nerve cell differentiation inducer (in particular, a fetal brain differentiation inducer, a cerebellum peduncle differentiation inducer, a cerebellum differentiation inducer, a whole brain differentiation inducer, a brain thalamus differentiation inducer, a hypothalamus differentiation inducer, a prefrontal cortex differentiation inducer, an occipital lobe differentiation inducer, a brain amygdala differentiation inducer, a caudate nucleus differentiation inducer, a cingulate cortex differentiation inducer, a medulla oblongata differentiation inducer, a globus pallidus differentiation inducer, a subthalamic nucleus differentiation inducer, a parietal lobe differentiation inducer, a temporal lobe differentiation inducer, or a pons differentiation inducer)

Motor Nerve Differentiation Inducer

The motor nerve means a motor neuron or a motoneuron. There are two kinds of motor neurons: central and peripheral motor neurons. The central motor neuron is a nerve from the brain to the spinal cord, and the peripheral motor neuron is a nerve from the spinal cord to a muscle. In particular, a peripheral motor nerve is preferred.

Pituitary Differentiation Inducer

Olfactory Nerve Differentiation Inducer (in Particular, an Olfactory Bulb Differentiation Inducer)

Spinal nerve differentiation inducer (in particular, a spinal cord differentiation inducer)

Skeletal muscle differentiation inducer (in particular, a psoas differentiation inducer or a tongue differentiation inducer)

Skin differentiation inducer

Ganglion differentiation inducer (in particular, a dorsal root ganglion differentiation inducer, a superior cervical ganglion differentiation inducer, an atrioventricular node differentiation inducer, a trigeminal ganglion differentiation inducer, or a ciliary ganglion differentiation inducer)

Ovary differentiation inducer

Adrenal gland differentiation inducer (in particular, an adrenal cortex differentiation inducer or an adrenal gland differentiation inducer)

Appendix differentiation inducer

Kidney differentiation inducer

Liver differentiation inducer (in particular, a liver differentiation inducer or a fetal liver differentiation inducer)

Salivary gland differentiation inducer

Islet differentiation inducer (in particular, an islet cell differentiation inducer)

Pancreas differentiation inducer

Prostate differentiation inducer

Thymus differentiation inducer (in particular, a thyroid differentiation inducer or a fetal thyroid differentiation inducer)

Adipocyte differentiation inducer (in particular, a cultured adipocyte differentiation inducer)

Uterus differentiation inducer (in particular, a uterus differentiation inducer or a uterus corpus differentiation inducer)

Blood cell differentiation inducer (in particular, a whole blood differentiation inducer, a bone marrow differentiation inducer, a monocyte differentiation inducer, a lymphnode differentiation inducer, a tonsil differentiation inducer, a thymus differentiation inducer, a natural killer cell differentiation inducer, a dendritic cell differentiation inducer, a B cell differentiation inducer, a B lymphoblast differentiation inducer, a T cell (PB_CD8 or PB_CD4) differentiation inducer, or an early erythroid differentiation inducer)

Bone marrow differentiation inducer

Blood cell (or hematopoietic stem cell) differentiation inducer

Vascular endothelial cell differentiation inducer

Testis differentiation inducer (in particular, a testis differentiation inducer, a testis Leydig cell differentiation inducer, a test is germ cell differentiation inducer, a test is seminiferous tubule differentiation inducer, or a testis interstitial cell differentiation inducer)

Heart differentiation inducer (in particular, a heart differentiation inducer or a cardiac myocyte differentiation inducer)

Placenta differentiation inducer

Smooth muscle differentiation inducer

Lung differentiation inducer (in particular, a lung differentiation inducer, a bronchial epithelial cell differentiation inducer, a fetal lung differentiation inducer, or a trachea differentiation inducer)

Cartilage differentiation inducer

The present invention is specifically described below by way of Examples. However, the present invention is not limited thereto. All Examples of the present invention have been approved by the Ethics Committee of Keio University School of Medicine.

Example 1

(Creation of Human Gene Expression Correlation Matrix)

In this Example, a human gene expression correlation matrix (see FIGS. 3A-3D and FIGS. 4A-4T) was created. The details are as described below.

With reference to the disclosures of the literatures "Cell Stem Cell 5, 420-433 (2009)" and "Sci Rep 1, 167 (2011)," gene expression profiles of human ES cells under 48-hour forced expression (DOX+) or not under forced expression (DOX−) were obtained by an RNA sequencing method (RNA-seq) for 175 transcription factors one by one. Further, 50-bp-long sequenced RNA fragments were aligned with human genome sequences by computer analysis. Next, the RNA fragments were identified for matching to mRNA/ncRNA from Ensembl and RefSeq (gene coordinates of transcripts were downloaded from the UCSC database, genome version hg19, hgdownload.soe.ucsc.edu/goldenPath/hg19 on Aug. 5, 2014).

Ensembl data was mainly used, and transcripts that were unable to be covered by the Ensembl data were complemented with RefSeq. With regard to the number of matches to the genome, a case in which the number of mismatches was 2 or less and the number of hits in the genome was 10 or less was adopted. The fragments were weighted by 1/n, where n represented the number of hits in a genome. The fragments were identified as transcription factors when: directions matched; the boundaries of genes and the boundaries of introns matched within a 5-bp distance; and the total matching length was 90% or less of the read length.

With regard to a gene expression change induced by forced expression of each transcription factor, a DOX+ sample log-transformed expression value (each clone was replicated once) was normalized by subtracting the log-transformed expression value of the corresponding DOX− sample and adding the median of the log-transformed expression values of all DOX− samples.

An association between the gene expression change induced by overexpression of a transcription factor and tissue-specific gene expression was evaluated on the basis of a correlation between the GNF database (see Non Patent Literature 22) and the results of RNA-seq.

The correlation was analyzed between the response of gene expression to transcription factor introduction in various tissues in the human GNF database ver. 2 and the median-subtraction log-transformed gene expression value. The correlation analysis was performed using 9, 980 genes that had shown significant values in both data sets. Criteria for significance of the GNF database were set to a false discovery rate (FDR) of 0.05 or less and a change of 2-fold or more. A correlation matrix was calculated by sorting with ExAtlas, lgsun.grc.nia.nih.gov/exatlas using hierarchical clustering.

The results of the creation of the human gene expression correlation matrix are shown in FIGS. 3A-3D and FIGS. 4A-4T. In FIGS. 3A-3D, a correlation matrix between "change in gene expression induced by forced expression of a specific transcription factor (horizontal axis)" and "tissue-specific gene expression from the GNF database (vertical axis)" is shown. Each cell of the matrix represents the significance of a correlation between "change in gene expression induced by forced expression of a specific transcription factor (measured in log-ratio, horizontal axis)" and "tissue-specific gene expression from the GNF database (vertical axis)" (z-value: Z-value). In FIGS. 4A-4T, the top 30 of the Z-values expressed in actual numbers are shown for each of the cells, the tissues, and the organs shown in FIGS. 3A-3D.

Example 2

(Method for Differentiation into Desired Cell Type)

Through use of the human gene expression correlation matrix obtained in Example 1 of the present invention (FIGS. 3A-3D and FIGS. 4A-4T), pluripotent stem cells can be differentiated into the cells, the tissues, and the organs shown in FIGS. 3A-3D. A molecular biological technique known per se may be utilized as a differentiation method. For example, a method involving using synthetic mRNAs, nanoparticle-encapsulated synthetic mRNAs, or Sendai virus vectors may be utilized. Those methods can each introduce the mRNA or protein of a transcription factor into a pluripotent stem cell in a footprint-free manner. The details are as described below.

Synthesis of mRNA Encoding Gene of Transcription Factor

With reference to a method disclosed in the literature "Warren et al., Cell Stem Cell, 2010 Nov. 5; 7 (5): 618-30," modified mRNA was synthesized. More specifically, mRNAs were synthesized by in vitro transcription using a mixture of dNTPs {(dNTPs: 3-0-Me-m7G (5') ppp (5') G ARCA cap analog, 5-methylcytidine triphosphate, and pseudouridine triphosphate)} obtained by modifying template DNAs encoding genes of transcription factors shown in FIGS. 3A-3D.

In order to express mammalian (in particular, human) transcription factors, Sendai vectors capable of expressing human transcription factors shown in FIGS. 3A-3D were used. In particular, mutants of Sendai virus vectors, such as F protein-deficient mutants, had no infectivity, and hence were easy to handle (see Inoue et al., J Virol. 77: 23238-3246, 2003).

(Method of Differentiating Pluripotent Stem Cell into Desired Cell Type)

With reference to the Z-values shown in FIGS. 4A-4T, a single transcription factor or a cocktail of two or more transcription factors was prepared. The form of the transcription factors is not particularly limited, and may be any of synthetic mRNAs, a Sendai virus vector having incorporated therein a transcription factor (or a plurality of transcription factors), and nanoparticle capsules containing synthetic mRNAs. The synthetic mRNA may carry, on the same gene, the gene sequences of a plurality of transcription factors.

A method of introducing the single transcription factor or cocktail of two or more transcription factors described above into cells is not particularly limited, and transfection with Lipofectamine, viral infection, or the like may be utilized.

Further, the type of cells (in particular, mammal cells, more preferably human cells) into which the single transcription factor or the cocktail of two or more transcription factors are introduced is not particularly limited, and encompasses pluripotent stem cells, such as embryonic stem cells (ESCs) and induced pluripotent stem cells (iPSCs), tissue stem cells derived from tissues and organs, dermal fibroblasts, and all kinds of cells derived from tissues and organs.

Figure 5:
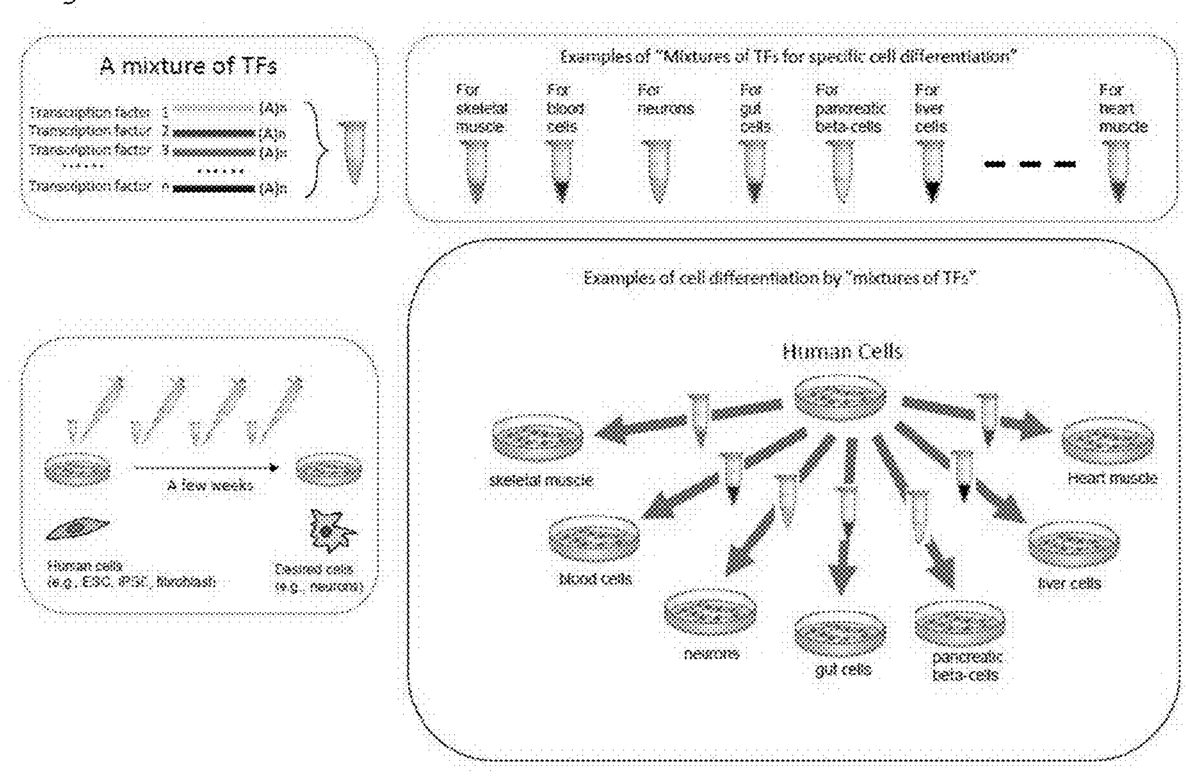
FIG. 5 is an illustration of a method of inducing differentiation into a desired cell type used in Examples of the present invention.

The outline of the steps of the method for differentiation into a desired cell type of this Example is illustrated in FIG. 5. Cells can be differentiated into the following desired cell types by introducing, into the cells, a transcription factor (or a transcription factor cocktail) selected from the human gene expression correlation matrix of Example 1 of the present invention by the method described in Example 2 of the present invention:

nerve cells (in particular, the fetal brain, the cerebellum peduncle, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons), the pituitary, the olfactory nerve (in particular, the olfactory bulb), the spinal nerve (in particular, the spinal cord), skeletal muscles (in particular, the psoas or the tongue), the skin, ganglions (in particular, the dorsal root ganglion, the superior cervical ganglion, the atrioventricular node, the trigeminal ganglion, or the ciliary ganglion), the ovary, the adrenal gland (in particular, the adrenal cortex or the adrenal gland), the appendix, the kidney, the liver (in particular, the liver or the fetal liver), the salivary gland, the islet (in particular, islet cells), the pancreas, the prostate, the thymus (in particular, the thyroid or the fetal thyroid), adipocytes (in particular, cultured adipocytes), the uterus (in particular, the uterus or the uterus corpus), blood cells (in particular, whole blood, the bone marrow, monocytes, lymph nodes, the tonsil, the thymus, natural killer cells, dendritic cells, B cells, B lymphoblasts, T cells (PB_CD8 or PB_CD4), or early erythroids), the bone marrow, hematopoietic stem cells, vascular endothelial cells, the testis (in particular, the testis, testis Leydig cells, testis germ cells, the testis seminiferous tubule, testis interstitial cells), the heart (in particular, the heart or cardiac myocytes), the placenta, smooth muscles, the lung (in particular, the lung, bronchial epithelial cells, the fetal lung, or the trachea), motor nerves, hepatoblasts/liver cells, and chondrocytes.

Example 3

(Differentiation into Nerve Cell)

In this Example, it was confirmed that human embryonic stem cells were able to be differentiated into nerve cells by introducing, into the human embryonic stem cells, a transcription factor cocktail selected from the human gene expression correlation matrix of Example 1 of the present invention by the method described in Example 2 of the present invention. The details are as described below.

(Method for Differentiation into Nerve Cell)

With reference to the transcription factors and their Z-values shown in FIGS. 3A-3D and FIGS. 4A-4T, synthetic mRNAs of a cocktail of four transcription factors each having a Z-value of 12 or more (NEUROD1, NEUROD2, NEUROG2, and NEUROG3) were introduced (transfected) into human embryonic stem cells using RNAiMAX transfection reagent. The transfection was performed twice on day 1 and twice on day 2 (see FIG. 6A). On day 3, the medium was changed to a standard nerve cell differentiation medium, and cells on day 7 of the culture were harvested.

(Confirmation of Differentiation into Nerve Cell)

Figures 6A, 6B:
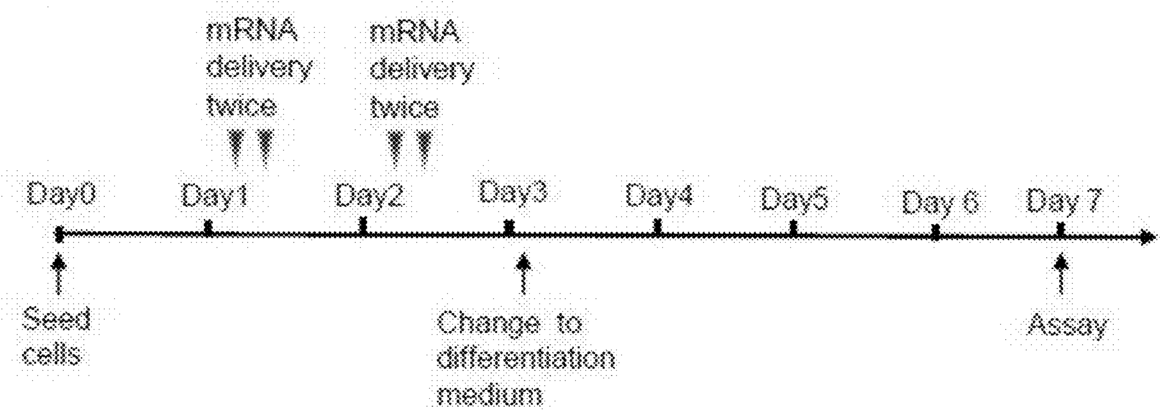
FIG. 6A is an illustration of a step of differentiating pluripotent stem cells into nerve cells.
FIG. 6B is photographs of results for showing that pluripotent stem cells have been able to be differentiated into nerve cells.

The differentiation state of the cells was confirmed using a marker of mature nerve cells (beta-3-tubulin, Bill) (see FIG. 6B). Alone, NEUROD1 increased cells stained with Bill, but a nerve cell form was not clearly observed.

Meanwhile, the cocktail of four transcription factors increased not only the number of cells stained with Bill, but also the number of cells in the form of mature nerve cells.

Thus, it was confirmed that pluripotent stem cells were able to be differentiated into nerve cells by introducing, into the pluripotent stem cells, the transcription factor cocktail associated with differentiation into nerve cells, which had been selected from the human gene expression correlation matrix of Example 1 of the present invention.

Example 4

(Differentiation into Motor Nerve)

In this Example, it was confirmed that human embryonic stem cells were able to be differentiated into motor nerves by adding (introducing), into the human embryonic stem cells or the human induced pluripotent stem cells, a transcription factor cocktail selected from the human gene expression correlation matrix of Example 1 of the present invention by the method described in Example 2 of the present invention. The details are as described below.

With reference to the transcription factors and their Z-values shown in FIGS. 3A-3D and FIGS. 4A-4T, synthetic mRNAs of a cocktail of five transcription factors (NEUROD1, NEUROD2, NEUROG1, NEUROG2, and NEUROG3) were introduced (transfected) into human embryonic stem cells using RNAiMAX transfection reagent. The transfection was performed twice on day 1, followed by culture for 6 days in a standard nerve cell differentiation medium, and cells on day 7 of the culture were harvested.

Figure 7:
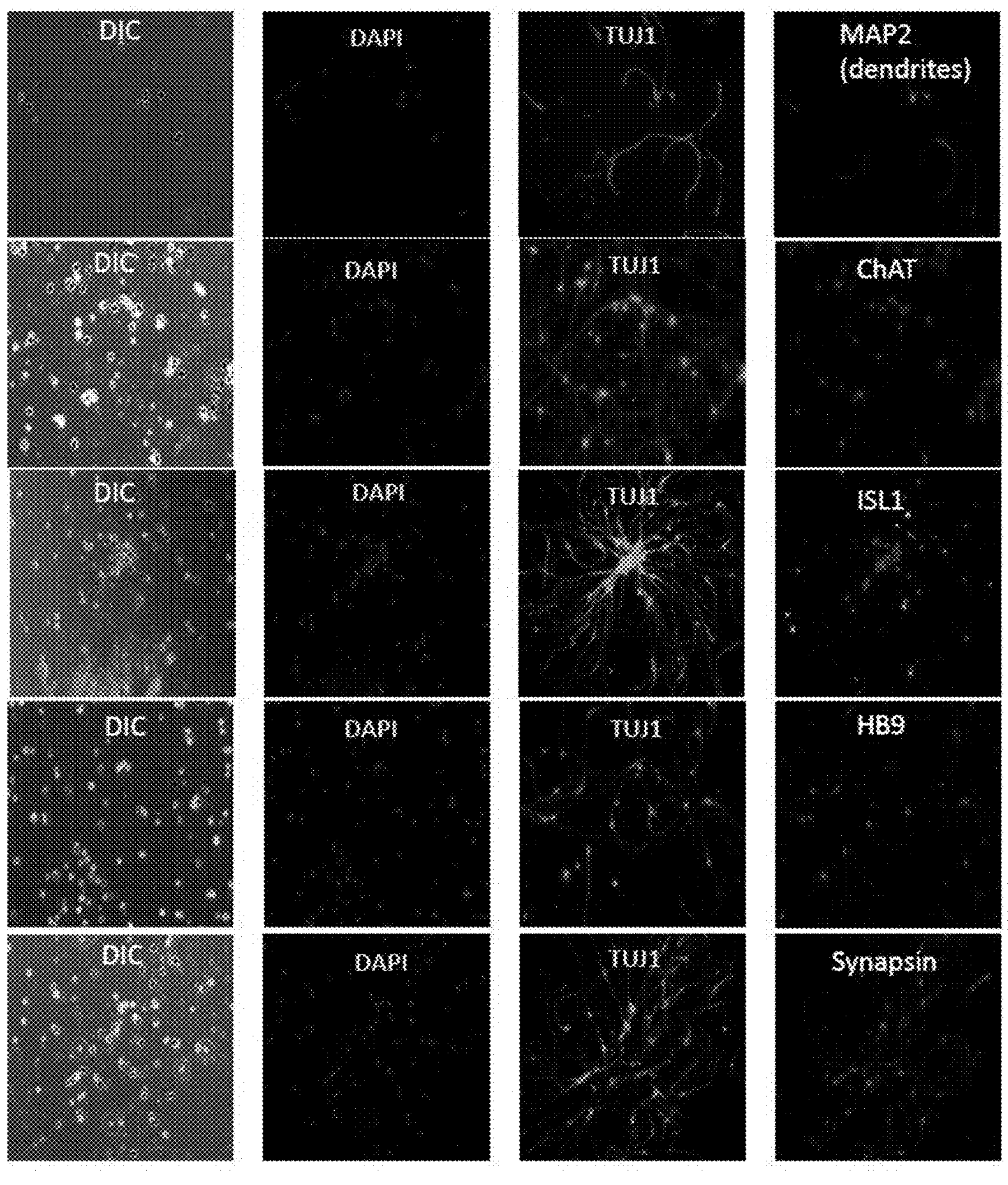
FIG. 7 is photographs of results for showing that human embryonic stem cells have been able to be differentiated into motor nerves.

The harvested cells were immunostained with a marker of nerve cells to confirm that the cells had differentiated into nerve cells (see FIG. 7). Further, electrophysiological analysis confirmed that those nerves were motor nerves on the basis of the expression of markers of choline-acetyl transferase (ChAT), ISL1, and HB9, and the like (see FIG. 7).

Culture conditions for differentiating human embryonic stem cells into nerve cells are already known. However, a related-art method generally takes from a few weeks to a month or more until a marker of nerve cells is expressed. Nonetheless, in this Example, it was confirmed that human embryonic stem cells were differentiated rapidly and highly efficiently by adding five kinds of synthetic mRNAs to the human embryonic stem cells.

Further, it was confirmed that the transfection was possible also by a method involving the first transfection with three kinds of transcription factors and the second transfection with two kinds of transcription factors.

Figure 8:
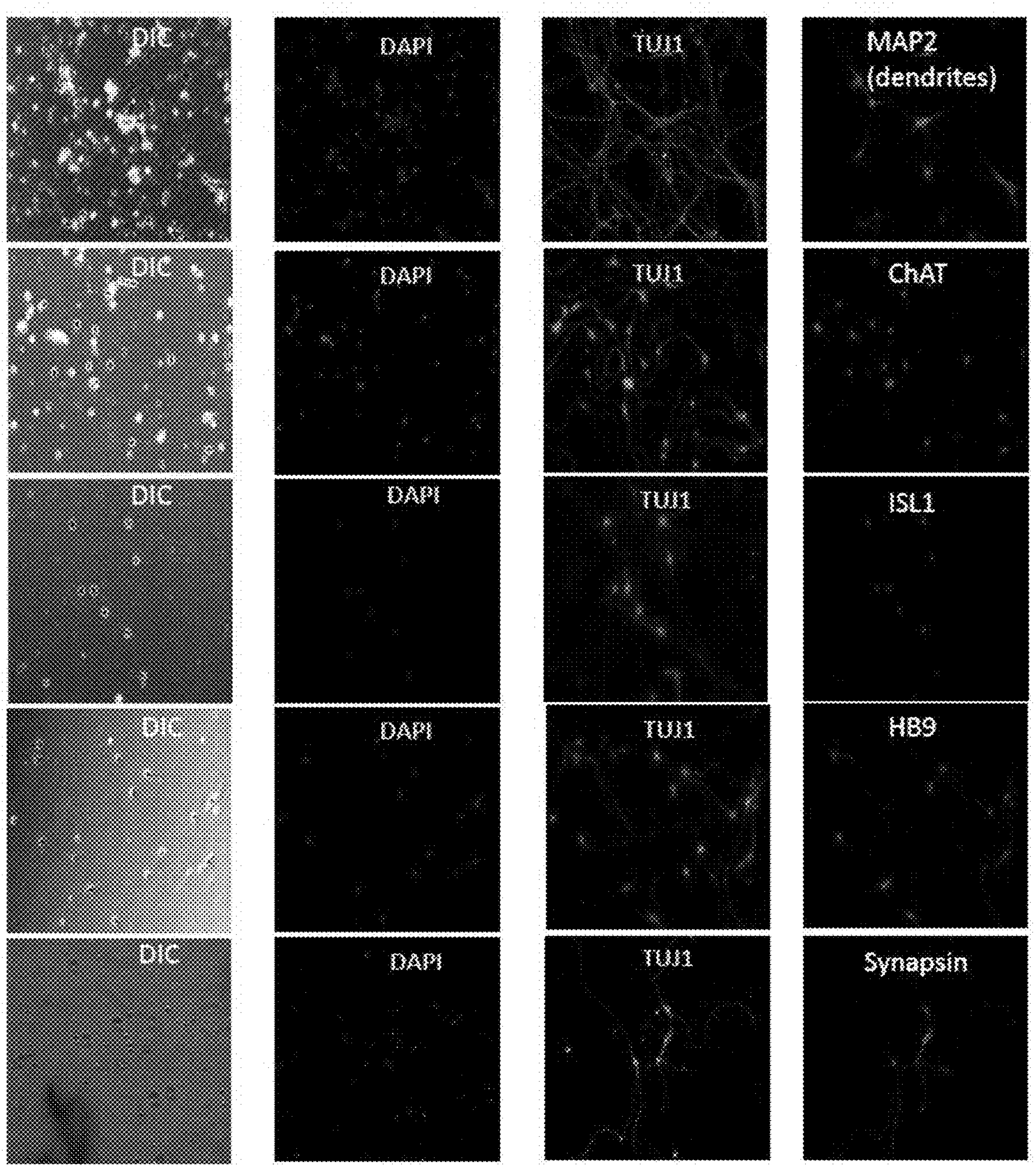
FIG. 8 is photographs of results for showing that human induced pluripotent stem cells have been able to be differentiated into motor nerves.

Human induced pluripotent stem cells were subjected to the same conditions as those for the human embryonic stem cells. The results for the human induced pluripotent stem cells confirmed rapid and highly efficient differentiation thereof as in the results for the human embryonic stem cells (see FIG. 8).

In this Example, it was confirmed for the first time that pluripotent stem cells were able to be differentiated into motor nerves (motor nerve cells, in particular, peripheral motor nerve cells).

Example 5

(Differentiation into Liver Cell)

In this Example, it was confirmed that human embryonic stem cells were able to be differentiated into liver cells/hepatoblasts by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, each transcription factor (TGIF, TCF4, PITX2, SALL4, or MEIS1) was selected. Through addition of doxycycline to human embryonic stem cells having introduced therein those transcription factors as Transgene to be induced by doxycycline, those transcription factors were forcibly expressed in human embryonic stem cells. The forced expression was performed for 24 hours on day 1, followed by culture for 8 days in a known liver cell differentiation medium, and cells on day 9 of the culture were harvested.

Figure 9:
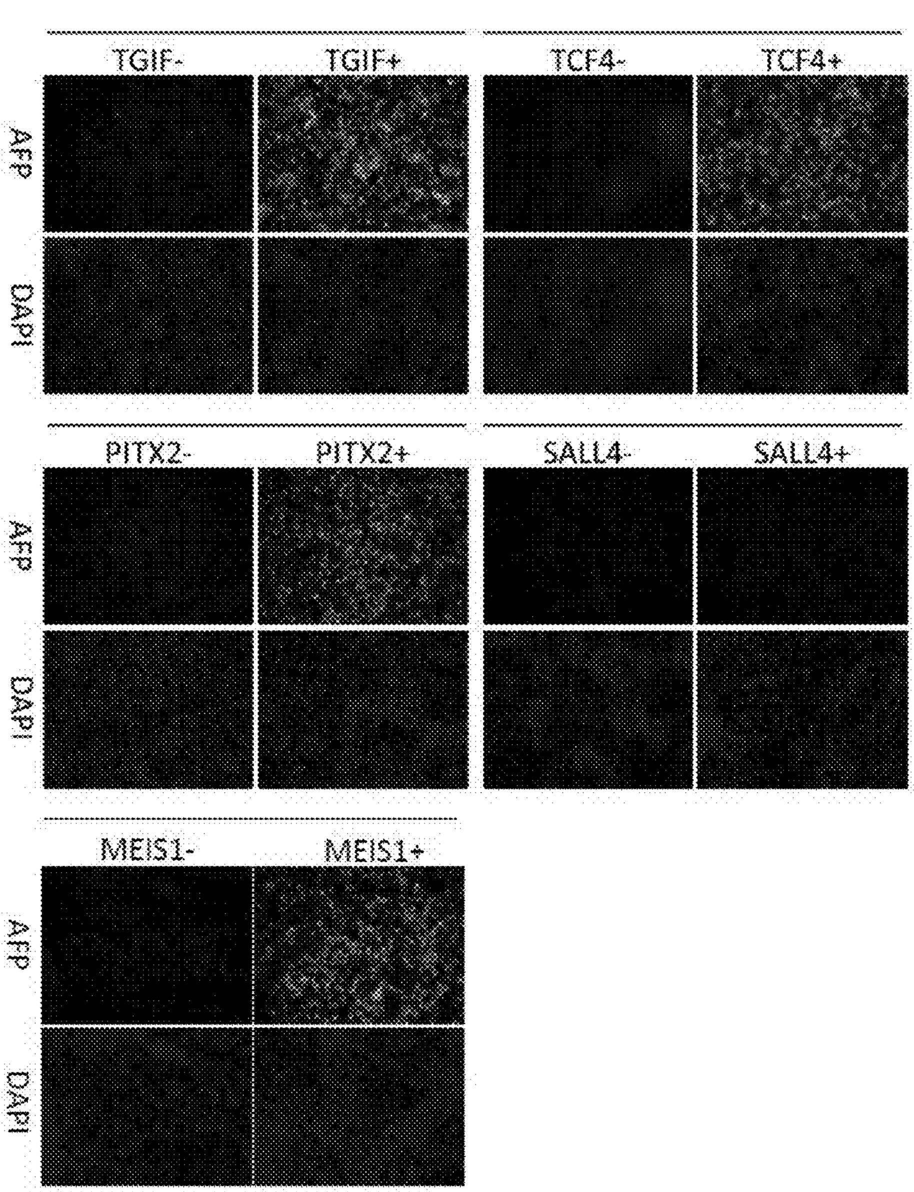
FIG. 9 is photographs of results for showing that pluripotent stem cells have been able to be differentiated into hepatoblasts/liver cells.

On the basis of the expression of albumin serving as a marker of liver cells, differentiation into liver cells/hepatoblasts was confirmed (see FIG. 9). In FIG. 9, "TGIF-, TCF4-, PITX2-, SALL4-, and MEIS1-" mean control groups having introduced therein no transcription factor.

Culture conditions for differentiating human embryonic stem cells into liver cells are already known. Such culture conditions are disclosed in, for example, Hay D C, et al. (2008), Stem Cells 26: 894-902. In addition, in the report by Kajiwara et al. (2012) {Proc Natl Acad Sci USA. 109: 12538-43}, it is reported that, when various cell growth and differentiation factors are progressively added into medium, the expression of albumin serving as a marker of hepatic cells starts on day 17. However, in this Example, under the same culture conditions, the expression of albumin was able to be confirmed on day 9 of the culture. In other words, the culture time was able to be shortened by about a half. In addition, the method disclosed in the literature requires the addition of a liver cell-specific differentiation factor HGF and the like on day 10 and thereafter. However, the addition was not required in this Example.

Inconsideration of the foregoing, the differentiation into liver cells of the present invention has the remarkable effect of rapid differentiation and the qualitatively different effect of not requiring the addition of the liver cell-specific differentiation factor HGF as compared to the related-art method.

Further, in this Example, the differentiation was able to be caused by introducing each one of the five transcription factors, but a method involving transfecting five, four, three, or two of the transcription factors simultaneously or separately is also possible.

Example 6

(Differentiation into Hematopoietic Stem Cell/Blood Cell)

In this Example, it was confirmed that human embryonic stem cells were able to be differentiated into hematopoietic stem cells/blood cells by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, each transcription factor (CDYL2, ETS2, SPI1, OVOL2, CDX2, CEBPB, or SALL4) was selected. Through addition of doxycycline to human embryonic stem cells having introduced therein those transcription factors as Transgene to be induced by doxycycline, those transcription factors were forcibly expressed in human embryonic stem cells. The forced expression was performed for 48 hours on from day 3 to day 5 of the culture, followed by culture in a known hematopoietic progenitor cell medium, and cells on day 5 of the culture were harvested.

Culture conditions for differentiating human ES cells into hematopoietic progenitor cells are already known. Such culture conditions are disclosed in, for example, the literature Wang et al. (2012) Cell Res. 22:194-207. In the literature, it is reported that, when various cell growth and differentiation factors are progressively added into a medium, the expression of CD43 serving as a marker of hematopoietic progenitor cells starts on day 17.

Figure 10:
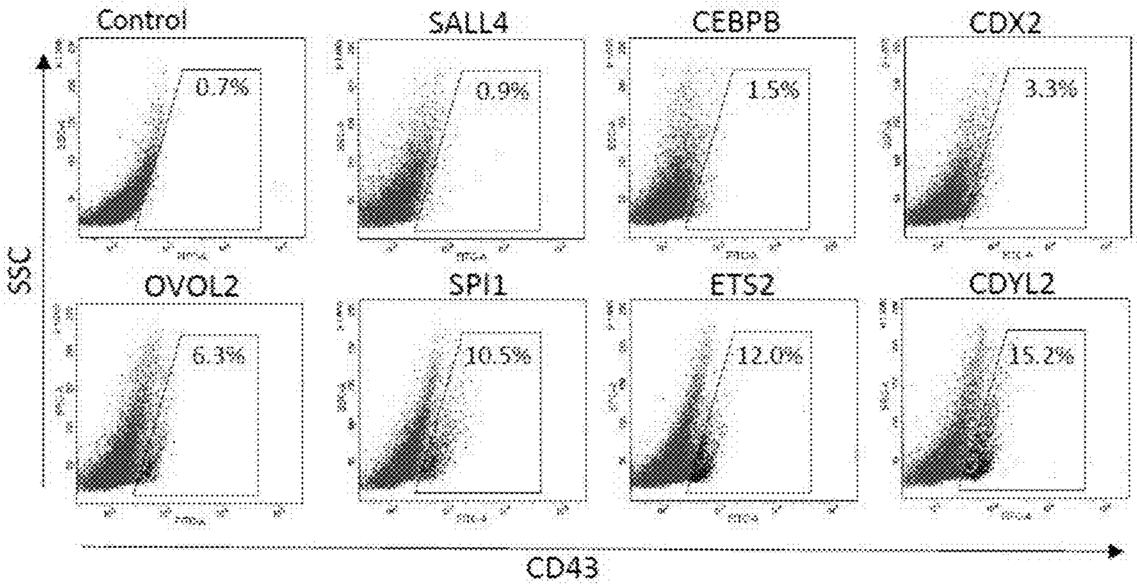
FIG. 10 is graphs of results for showing that pluripotent stem cells have been able to be differentiated into hematopoietic stem cells/blood cells.

However, in this Example, it was found that forced expression (induced with DOX) of a transcription factor under known hematopoietic progenitor cell conditions remarkably increased the speed and efficiency of the differentiation into hematopoietic progenitor cells. Irrespective of whether the transcription factors were used alone or in combination thereof, the transcription factors were able to cause the differentiation. More specifically, in this Example, the expression of CD43 serving as a marker of hematopoietic progenitor cells was confirmed on day 5 of the culture (see FIG. 10). On day 5, in the control group (related art) having introduced therein no transcription factor, the expression of CD43 was hardly recognized. Thus, the method of the present invention has an about 4-fold differentiation-inducing ability (differentiation speed) as compared to the related-art method.

Example 7

(Differentiation into Chondrocyte)

In this Example, it was confirmed that human embryonic stem cells were able to be differentiated into chondrocytes by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, SOX9 was selected. Through addition of doxycycline to human embryonic stem cells having introduced therein SOX9 as Transgene to be induced by doxycycline, SOX9 was forcibly expressed in human embryonic stem cells. The forced expression was performed for 24 hours on day 1, followed by culture for 2 days in a known human embryonic stem cell culture medium, and cells on day 3 of the culture were harvested.

Culture conditions for differentiating human embryonic stem cells into chondrocytes are already known. Such culture conditions are disclosed in, for example, the literature Oldershaw et al. (2010). Nat Biotechnol. 28:1187-94. In the literature, type II collagen-positive chondrocytes are produced on 14th day after differentiation induction in such a complicated manner that various cell growth and differentiation factors are progressively added in stages into a medium.

Figure 11:
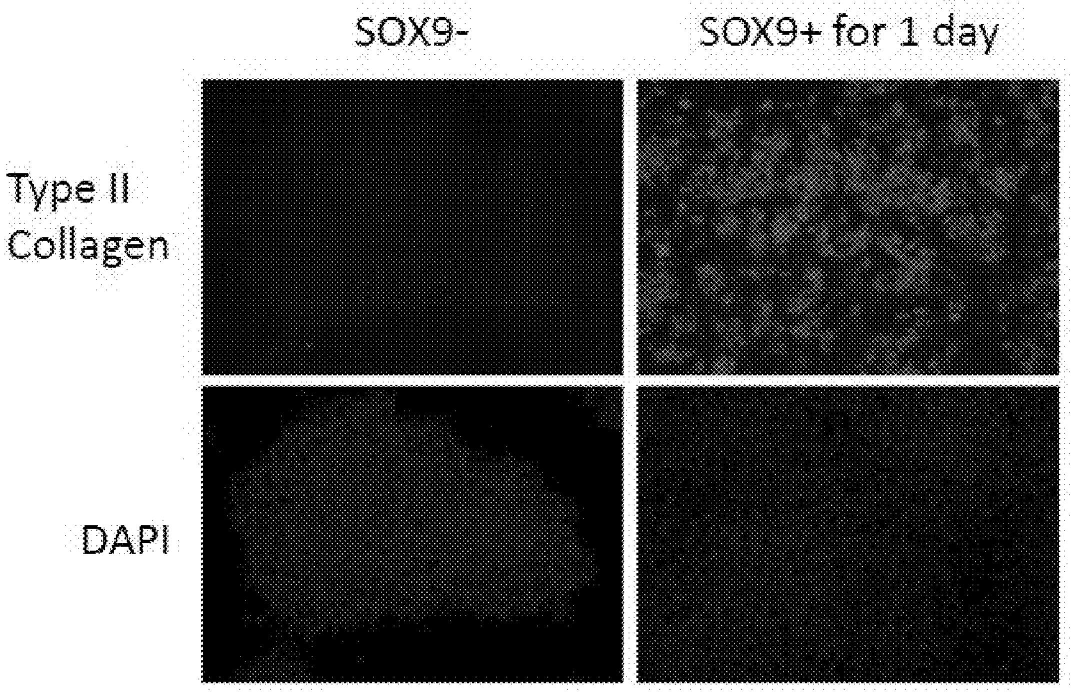
FIG. 11 is photographs of results for showing that pluripotent stem cells have been able to be differentiated into chondrocytes.

However, in this Example, it was confirmed that, as a result of forced expression of SOX9, type II collagen-positive chondrocytes were able to be produced 2 days after the forced expression (i.e., on the 3rd day after differentiation induction) (see "SOX9+ for 1 day" of FIG. 11). In this Example, the differentiation-promoting medium used in the literature was not used, and a general embryonic stem cell culture medium was used. In the control to which SOX9 had not been added (see "SOX9-" of FIG. 11), the expression of type II collagen was not able to be confirmed.

As can be seen from the above, the differentiation method of the present invention does not use any special medium, and the method of the present invention has an about 4-fold differentiation-inducing ability (differentiation speed) as compared to the related-art method.

Example 8

(Differentiation into Nerve Cell)

In this Example, a human embryonic stem cell can be differentiated into a nerve cell by introducing, into the human embryonic stem cell, a transcription factor cocktail selected from the human gene expression correlation matrix of Example 1 of the present invention by the method described in Example 2 of the present invention.

A method for differentiation into the nerve cell (in particular, a cell present in the fetal brain, the cerebellum peduncle, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons) of the present invention is as described below.

Fetal brain: NEUROG2, NEUROG1, NEUROG3, SOX11, MXI1, PDX1, NEUROD2, HOXA2, and NEUROD1 are introduced into a human pluripotent stem cell.

Cerebellum peduncle: NEUROG2, NEUROG3, NEUROG1, NEUROD1, NRF1, ASCL1, HOXA2, PITX2, and NEUROD2 are introduced into a human pluripotent stem cell.

Cerebellum: NEUROG2, NEUROG3, NEUROG1, NEUROD1, NRF1, HOXA2, ASCL1, PITX2, NEUROD2, PRDM1, and NFIB are introduced into a human pluripotent stem cell.

Whole brain: NEUROG2, NEUROG3, NEUROG1, NEUROD1, NRF1, and HOXA2 are introduced into a human pluripotent stem cell.

Brain thalamus: NEUROG2, NEUROG3, HOXA2, NEUROG1, and ASCL1 are introduced into a human pluripotent stem cell.

Hypothalamus: NEUROG2, SOX2, NEUROG1, NEUROG3, HOXA2, and SOX11 are introduced into a human pluripotent stem cell.

Prefrontal cortex: NEUROG2, NEUROG3, NEUROG1, SOX11, MXI1, SOX2, HOXA2, PDX1, ASCL1, NEUROD1, and NEUROD2 are introduced into a human pluripotent stem cell.

Occipital lobe: NEUROG2, NEUROG1, NEUROG3, HOXA2, SOX2, SOX11, PDX1, NEUROD1, ASCL1, and MXI1 are introduced into a human pluripotent stem cell.

Brain amygdala: NEUROG2, NEUROG1, NEUROG3, HOXA2, SOX2, PDX1, SOX11, MXI1, NEUROD1, and ASCL1 are introduced into a human pluripotent stem cell.

Caudate nucleus: NEUROG2, HOXA2, NEUROG1, NEUROG3, SOX2, NRF1, ASCL1, and PDX1 are introduced into a human pluripotent stem cell.

Cingulate cortex: NEUROG2, NEUROG3, NEUROG1, HOXA2, ASCL1, SOX11, PDX1, NRF1, NEUROD1, and PRDM1 are introduced into a human pluripotent stem cell.

Medulla oblongata: NEUROG2, HOXA2, NEUROG1, NEUROG3, PDX1, SOX11, SOX2, NRF1, ASCL1, NR2F2, and GLIS2 are introduced into a human pluripotent stem cell.

Globus pallidus: NEUROG2, HOXA2, NEUROG1, NEUROG3, NRF1, ASCL1, SOX11, and PDX1 are introduced into a human pluripotent stem cell.

Subthalamic nucleus: NEUROG2, HOXA2, NEUROG1, NEUROG3, NRF1, ASCL1, SOX11, and PDX1 are introduced into a human pluripotent stem cell.

Parietal lobe: NEUROG2, HOXA2, NEUROG3, NEUROG1, NRF1, SOX11, ASCL1, PDX1, and SOX2 are introduced into a human pluripotent stem cell.

Temporal lobe: NEUROG2, HOXA2, NRF1, NEUROG1, and NEUROG3 are introduced into a human pluripotent stem cell.

Pons: HOXA2, NRF1, NEUROG2, NEUROG1, NEUROG3, CTCF, NR2F2, HES1, NFIC, PDX1, SOX11, and ERG are introduced into a human pluripotent stem cell.

Example 9

(Differentiation into Pituitary)

In this Example, a human embryonic stem cell can be differentiated into the pituitary, in particular, a cell present in the pituitary by introducing, into the human embryonic stem cell, a transcription factor cocktail selected from the human gene expression correlation matrix of Example 1 of the present invention by the method described in Example 2 of the present invention.

A method for differentiation into the pituitary of the present invention is as described below.

SOX2, NANOG, ASCL1, DLX4, DLX3, and CDX2 are introduced into a human pluripotent stem cell.

Example 10

(Differentiation into Olfactory Nerve)

In this Example, a human embryonic stem cell can be differentiated into the olfactory nerve, in particular, a cell present in the olfactory nerve by introducing, into the human embryonic stem cell, a transcription factor cocktail selected from the human gene expression correlation matrix of Example 1 of the present invention by the method described in Example 2 of the present invention.

A method for differentiation into the olfactory nerve (in particular, the olfactory bulb) of the present invention is as described below.

Olfactory bulb: NFIB, TBX2, TBX3, SOX2, NFIC, HES1, JUNB, FOS, and FOXA2 are introduced into a human pluripotent stem cell.

Example 11

(Differentiation into Spinal Nerve)

In this Example, a human embryonic stem cell can be differentiated into the spinal nerve, in particular, a cell present in the spinal nerve by introducing, into the human embryonic stem cell, a transcription factor cocktail selected from the human gene expression correlation matrix of Example 1 of the present invention by the method described in Example 2 of the present invention.

A method for differentiation into the spinal nerve (in particular, the spinal cord) of the present invention is as described below.

Spinal cord: NFIB, SOX2, HOXA2, TBX3, and E2F6 are introduced into a human pluripotent stem cell.

Example 12

(Differentiation into Skeletal Muscle)

In this Example, a human embryonic stem cell can be differentiated into a skeletal muscle, in particular, a cell present in the skeletal muscle by introducing, into the human embryonic stem cell, a transcription factor cocktail selected from the human gene expression correlation matrix of Example 1 of the present invention by the method described in Example 2 of the present invention.

A method for differentiation into the skeletal muscle (in particular, the psoas or the tongue) of the present invention is as described below.

Psoas: MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, and PITX2 are introduced into a human pluripotent stem cell.

Tongue: MYOD1, TP73, HES1, JUNB, KLF4, SALL4, ZIC1, ESX1, ZNF281, TBX5, NRF1, HEY1, TFAP2C, FOS, FOXP1, TFE3, CTCF, FOSL1, GRHL2, TBX2, NFIB, PITX2, KLF9, and IRF4 are introduced into a human pluripotent stem cell.

Example 13

(Differentiation into Skin)

In this Example, a human embryonic stem cell can be differentiated into the skin, in particular, a cell present in the skin by introducing, into the human embryonic stem cell, a transcription factor cocktail selected from the human gene expression correlation matrix of Example 1 of the present invention by the method described in Example 2 of the present invention.

A method for differentiation into the skin of the present invention is as described below.

HES1, CTCF, TP73, JUNB, HEY1, ZIC1, TBX5, NFIC, TFAP2C, ESX1, NRF1, HOXA2, ELF1, NR2F2, KLF9, GRHL2, IRF4, ERG, FOS, TBX2, SALL4, and KLF4 are introduced into a human pluripotent stem cell.

Example 14

(Differentiation into Ganglion)

In this Example, a human embryonic stem cell can be differentiated into a ganglion, in particular, a cell present in the ganglion by introducing, into the human embryonic stem cell, a transcription factor cocktail selected from the human gene expression correlation matrix of Example 1 of the present invention by the method described in Example 2 of the present invention.

A method for differentiation into the ganglion (in particular, the dorsal root ganglion, the superior cervical ganglion, the atrioventricular node, the trigeminal ganglion, or the ciliary ganglion) of the present invention is as described below.

Dorsal root ganglion: HES1, HOXA2, CTCF, TBX2, NR2F2, NRF1, HEY1, NFIC, TBX3, JUNB, TBX5, E2F6, GLIS2, ZIC1, ERG, and KLF9 are introduced into a human pluripotent stem cell.

Superior cervical ganglion: HES1, CTCF, NRF1, HOXA2, HEY1, NFIC, NR2F2, TBX5, KLF9, ZIC1, ERG, FLI1, TBX2, JUNB, ELF1, GLIS2, TBX3, TFAP4, IRF4, and PDX1 are introduced into a human pluripotent stem cell.

Atrioventricular node: HES1, CTCF, NRF1, HEY1, HOXA2, NFIC, NR2F2, ZIC1, TBX5, KLF9, TBX2, ERG, JUNB, TFAP2C, ELF1, TP73, TFAP4, ESX1, E2F6, IRF4, FLI1, SALL4, TBX3, and ARNT2 are introduced into a human pluripotent stem cell.

Trigeminal ganglion: HES1, CTCF, HOXA2, HEY1, NRF1, NR2F2, NFIC, TBX5, JUNB, ZIC1, TBX2, KLF9, ERG, ELF1, TBX3, E2F6, ESX1, ARNT2, GLIS2, TP73, and IRF4 are introduced into a human pluripotent stem cell.

Ciliary ganglion: HES1, CTCF, HEY1, NFIC, JUNB, HOXA2, NRF1, NR2F2, TBX2, ZIC1, TBX5, NFIB, ARNT2, ESX1, IRF4, ERG, TBX3, TFAP2C, ELF1, FOS, TP73, HSF1, KLF9, GLIS2, E2F6, PITX2, ZNF281, FOSL1, IRF1, FOXP1, and GATA3 are introduced into a human pluripotent stem cell.

Example 15

(Differentiation into Ovary)

In this Example, a human embryonic stem cell can be differentiated into the ovary, in particular, a cell present in the ovary by introducing, into the human embryonic stem cell, a transcription factor cocktail selected from the human gene expression correlation matrix of Example 1 of the present invention by the method described in Example 2 of the present invention.

A method for differentiation into the ovary of the present invention is as described below.

HES1, HEY1, CTCF, NR2F2, NFIC, TBX2, TBX3, NRF1, ZIC1, HOXA2, TBX5, JUNB, and ERG are introduced into a human pluripotent stem cell.

Example 16

(Differentiation into Adrenal Gland)

In this Example, a human embryonic stem cell can be differentiated into the adrenal gland, in particular, a cell present in the adrenal gland by introducing, into the human embryonic stem cell, a transcription factor cocktail selected from the human gene expression correlation matrix of Example 1 of the present invention by the method described in Example 2 of the present invention.

A method for differentiation into the adrenal gland (in particular, the adrenal cortex or the adrenal gland) of the present invention is as described below.

Adrenal cortex: SALL4, HES1, HEY1, ZIC1, FOXP1, ESX1, PITX2, NRF1, TP73, JUNB, DLX6, and TGIF1 are introduced into a human pluripotent stem cell.

Adrenal gland: TGIF1, SALL4, TFE3, NFIB, ZIC1, and DLX6 are introduced into a human pluripotent stem cell.

Example 17

(Differentiation into Appendix)

In this Example, a human embryonic stem cell can be differentiated into the appendix, in particular, a cell present in the appendix by introducing, into the human embryonic stem cell, a transcription factor cocktail selected from the human gene expression correlation matrix of Example 1 of the present invention by the method described in Example 2 of the present invention.

A method for differentiation into the appendix of the present invention is as described below.

HES1, CTCF, NR2F2, HEY1, HOXA2, NFIC, TBX2, NRF1, JUNB, TBX5, ZIC1, ERG, GLIS2, KLF9, ELF1, TBX3, IRF4, ARNT2, E2F6, IRF1, HSF1, SOX2, TFAP2C, TFAP4, FLI1, PDX1, RUNX3, MYOD1, HNF1A, NFIB, ESX1, and TP73 are introduced into a human pluripotent stem cell.

Example 18

(Differentiation into Kidney)

In this Example, a human embryonic stem cell can be differentiated into the kidney, in particular, a cell present in the kidney by introducing, into the human embryonic stem cell, a transcription factor cocktail selected from the human gene expression correlation matrix of Example 1 of the present invention by the method described in Example 2 of the present invention.

A method for differentiation into the kidney of the present invention is as described below.

HNF4A, SALL4, TGIF1, HNF1A, ZIC1, NFIB, TFE3, TP73, TFAP2C, NRF1, SMAD7, and MAB21L3 are introduced into a human pluripotent stem cell.

Example 19

(Differentiation into Liver)

In this Example, a human embryonic stem cell can be differentiated into the liver, in particular, a cell present in the liver by introducing, into the human embryonic stem cell, a transcription factor cocktail selected from the human gene expression correlation matrix of Example 1 of the present invention by the method described in Example 2 of the present invention.

A method for differentiation into the liver (in particular, the liver or the fetal liver) of the present invention is as described below.

Liver: SALL4, TGIF1, MAB21L3, ZIC1, EGFLAM, PITX2, HNF4A, NRF1, ZNF281, CTCFL, TP73, TFE3, DLX6, and TCF4 are introduced into a human pluripotent stem cell.

Fetal liver: SIX5, HNF4A, SIN3A, ID1, and HNF1A are introduced into a human pluripotent stem cell.

Example 20

(Differentiation into Salivary Gland)

In this Example, a human embryonic stem cell can be differentiated into the salivary gland, in particular, a cell present in the salivary gland by introducing, into the human embryonic stem cell, a transcription factor cocktail selected from the human gene expression correlation matrix of Example 1 of the present invention by the method described in Example 2 of the present invention.

A method for differentiation into the salivary gland of the present invention is as described below.

HES1, HEY1, ELF1, CTCF, and FLI1 are introduced into a human pluripotent stem cell.

Example 21

(Differentiation into Islet)

In this Example, a human embryonic stem cell can be differentiated into the islet, in particular, a cell present in the islet by introducing, into the human embryonic stem cell, a transcription factor cocktail selected from the human gene expression correlation matrix of Example 1 of the present invention by the method described in Example 2 of the present invention.

A method for differentiation into the islet (in particular, an islet cell) of the present invention is as described below.

ASCL1, CEBPB, HES1, JUNB, and TFE3 are introduced into a human pluripotent stem cell.

Example 22

(Differentiation into Pancreas)

In this Example, a human embryonic stem cell can be differentiated into the pancreas, in particular, a cell present in the pancreas by introducing, into the human embryonic stem cell, a transcription factor cocktail selected from the human gene expression correlation matrix of Example 1 of the present invention by the method described in Example 2 of the present invention.

A method for differentiation into the pancreas of the present invention is as described below.

HNF4A, ELF1, ZIC1, SALL4, and JUNB are introduced into a human pluripotent stem cell.

Example 23

(Differentiation into Prostate)

In this Example, a human embryonic stem cell can be differentiated into the prostate, in particular, a cell present in the prostate by introducing, into the human embryonic stem cell, a transcription factor cocktail selected from the human gene expression correlation matrix of Example 1 of the present invention by the method described in Example 2 of the present invention.

A method for differentiation into the prostate of the present invention is as described below.

NFIB, TP73, FOS, IRF5, ESRRB, TFAP2C, GRHL2, HHEX, HOXA9, DLX6, ESX1, TGIF1, SALL4, CEBPB, and JUNB are introduced into a human pluripotent stem cell.

Example 24

(Differentiation into Thyroid)

In this Example, a human embryonic stem cell can be differentiated into the thymus, in particular, a cell present in the thymus by introducing, into the human embryonic stem cell, a transcription factor cocktail selected from the human gene expression correlation matrix of Example 1 of the present invention by the method described in Example 2 of the present invention.

A method for differentiation into the thyroid thymus (in particular, the thyroid or the fetal thyroid) of the present invention is as described below.

Thyroid: MYOD1, NFIB, HHEX, ASCL2, and PPARG are introduced into a human pluripotent stem cell.

Fetal thyroid: NFIB, MYOD1, HHEX, TGIF1, and TFAP2C are introduced into a human pluripotent stem cell.

Example 25

(Differentiation into Adipocyte)

In this Example, a human embryonic stem cell can be differentiated into an adipocyte by introducing, into the human embryonic stem cell, a transcription factor cocktail selected from the human gene expression correlation matrix of Example 1 of the present invention by the method described in Example 2 of the present invention.

A method for differentiation into the adipocyte (in particular, a cultured adipocyte) of the present invention is as described below.

Cultured adipocyte: JUN, NFIB, FOSL1, FOS, JUNB, and SREBF2 are introduced into a human pluripotent stem cell.

Example 26

(Differentiation into Uterus)

In this Example, a human embryonic stem cell can be differentiated into the uterus, in particular, a cell present in the uterus by introducing, into the human embryonic stem cell, a transcription factor cocktail selected from the human gene expression correlation matrix of Example 1 of the present invention by the method described in Example 2 of the present invention.

A method for differentiation into the uterus (in particular, the uterus or the uterus corpus) of the present invention is as described below.

Uterus: NFIB, JUN, FOSL1, SOX2, RUNX3, NFIC, JUNB, IRF5, PTF1A, HSF1, TBX2, TBX3, FOS, MEF2C, ARNT2, and GATA2 are introduced into a human pluripotent stem cell.

Uterus corpus: HES1, JUNB, CTCF, HEY1, FOS, ZIC1, HOXA2, NFIC, FOSL1, NRF1, TBX5, ARNT2, NFIB, TFAP2C, ESX1, TBX2, TBX3, NR2F2, TP73, IRF4, THAP11, ELF1, JUN, ERG, HSF1, and KLF9 are introduced into a human pluripotent stem cell.

Example 27

(Differentiation into Blood Cell)

In this Example, a human embryonic stem cell can be differentiated into a blood cell, into the human embryonic stem cell, a transcription factor cocktail selected from the human gene expression correlation matrix of Example 1 of the present invention by the method described in Example 2 of the present invention.

A method for differentiation into the blood cell (in particular, whole blood, the bone marrow, a monocyte, a lymphnode, the tonsil, the thymus, a natural killer cell, a dendritic cell, a B cell, a B lymphoblast, a T cell (PB_CD8 or PB_CD4), or an early erythroid) of the present invention is as described below.

Whole blood: CEBPB, SPI1, ETS1, ELF1, IRF1, ETS2, IRF2, DMRT1, and KLF4 are introduced into a human pluripotent stem cell.

Bone marrow: SALL4, CEBPB, ESX1, ELF1, ZIC1, ZNF281, ETS1, KLF4, FOXP1, NRF1, and SPI1 are introduced into a human pluripotent stem cell.

Bone marrow: CEBPB, SPI1, ETS1, ELF1, CDYL2, IRF1, and GADD45A are introduced into a human pluripotent stem cell.

Monocyte: SPI1, CEBPB, ETS1, ELF1, IRF1, CDYL2, and GADD45A are introduced into a human pluripotent stem cell.

Lymphnode: IRF1, IRF2, ELF1, ETS1, SPI1, ETS2, IRF4, and RUNX3 are introduced into a human pluripotent stem cell.

Tonsil: ELF1, SPI1, IRF1, IRF2, ESX1, IRF4, KLF4, SALL4, and ETS1 are introduced into a human pluripotent stem cell.

Thymus: SALL4, ESX1, ETS1, SPI1, and ETS2 are introduced into a human pluripotent stem cell.

Natural killer cell: ETS1, CDYL2, GADD45A, IRF1, and IRF2 are introduced into a human pluripotent stem cell.

Dendritic cell: CDYL2, SPI1, GADD45A, ETS1, and MYC are introduced into a human pluripotent stem cell.

B cell: CDYL2, MYC, ATF2, IRF2, and GBX2 are introduced into a human pluripotent stem cell.

B lymphoblast: MYC, CDYL2, GADD45A, GBX2, ATF2, RUVBL2, PLXNB3, L3MBTL2, E2F4, SMARCA4, ID1, and ZSCAN4 are introduced into a human pluripotent stem cell.

T cell (PB_CD8): CDYL2, MYC, GBX2, ETS1, and IRF2 are introduced into a human pluripotent stem cell.

T cell (PB_CD4): CDYL2, MYC, GBX2, ETS1, and ATF2 are introduced into a human pluripotent stem cell.

Early erythroid: CDYL2, E2F4, GADD45A, and ZSCAN4 are introduced into a human pluripotent stem cell.

Example 28

(Differentiation into Bone Marrow)

In this Example, a human embryonic stem cell can be differentiated into the bone marrow, in particular, a cell present in the bone marrow by introducing, into the human embryonic stem cell, a transcription factor cocktail selected from the human gene expression correlation matrix of Example 1 of the present invention by the method described in Example 2 of the present invention.

A method for differentiation into the bone marrow of the present invention is as described below.

SALL4, CEBPB, ESX1, ELF1, ZIC1, ZNF281, ETS1, KLF4, FOXP1, NRF1, and SPI1 are introduced into a human pluripotent stem cell.

Example 29

(Differentiation into Hematopoietic Stem Cell)

In this Example, a human embryonic stem cell can be differentiated into a hematopoietic stem cell by introducing, into the human embryonic stem cell, a transcription factor cocktail selected from the human gene expression correlation matrix of Example 1 of the present invention by the method described in Example 2 of the present invention.

A method for differentiation into the hematopoietic stem cell of the present invention is as described below.

MYC, GBX2, CDYL2, GADD45A, ATF2, ID1, ZSCAN4, SMARCA4, E2F4, and RUVBL2 are introduced into a human pluripotent stem cell.

Example 30

(Differentiation into Vascular Endothelial Cell)

In this Example, a human embryonic stem cell can be differentiated into a vascular endothelial cell by introducing, into the human embryonic stem cell, a transcription factor cocktail selected from the human gene expression correlation matrix of Example 1 of the present invention by the method described in Example 2 of the present invention.

A method for differentiation into the vascular endothelial cell of the present invention is as described below.

MYC, RUVBL2, GBX2, CDYL2, GADD45A, ATF2, ID1, and E2F4 are introduced into a human pluripotent stem cell.

Example 31

(Differentiation into Testis)

In this Example, a human embryonic stem cell can be differentiated into the testis, in particular, a cell present in the testis by introducing, into the human embryonic stem cell, a transcription factor cocktail selected from the human gene expression correlation matrix of Example 1 of the present invention by the method described in Example 2 of the present invention.

A method for differentiation into the testis (in particular, the testis, a testis Leydig cell, a testis germ cell, the testis seminiferous tubule, or a testis interstitial cell) of the present invention is as described below.

Testis: SALL4, MYBL2, RFX2, TGIF1, and CTCFL are introduced into a human pluripotent stem cell.

Testis Leydig cell: MYBL2, NR2F2, KLF9, GLIS2, and SIX5 are introduced into a human pluripotent stem cell.

Testis germ cell: MYBL2, L3MBTL2, E2F4, KDM5A, and DMRT1 are introduced into a human pluripotent stem cell.

Testis seminiferous tubule: MYBL2, E2F4, KLF9, YY1, and NEUROD1 are introduced into a human pluripotent stem cell.

Testis interstitial cell: MYBL2, E2F4, NR2F2, KLF9, and GTF2F1 are introduced into a human pluripotent stem cell.

Example 32

(Differentiation into Heart)

In this Example, a human embryonic stem cell can be differentiated into the heart, in particular, a cell present in the heart by introducing, into the human embryonic stem cell, a transcription factor cocktail selected from the human gene expression correlation matrix of Example 1 of the present invention by the method described in Example 2 of the present invention.

A method for differentiation into the heart (in particular, the heart or a cardiac myocyte) of the present invention is as described below.

Heart: SALL4, TGIF1, PITX2, ZNF281, NRF1, ZIC1, TP73, FOXP1, CTCFL, NFIB, TFE3, EGFLAM, DLX6, TFAP2C, MYOD1, ESX1, PRDM1, MAB21L3, FOS, TCF4, JUNB, SMAD7, KLF4, ARID3A, TBX5, HOXA9, HES1, FOXG1, FOSL2, USF2, ERG, and ARNT2 are introduced into a human pluripotent stem cell.

Cardiac myocyte: FOSL1, JUN, FOS, FOSL2, JUNB, HSF1, CUX1, IRF5, ESX1, and ETS2 are introduced into a human pluripotent stem cell.

Example 33

(Differentiation into Placenta)

In this Example, a human embryonic stem cell can be differentiated into the placenta, in particular, a cell present in the placenta by introducing, into the human embryonic stem cell, a transcription factor cocktail selected from the human gene expression correlation matrix of Example 1 of the present invention by the method described in Example 2 of the present invention.

A method for differentiation into the placenta of the present invention is as described below.

TFAP2C, ESX1, FOS, JUNB, TP73, IRF5, GATA3, TFE3, CEBPB, FOSL1, DLX6, JUN, FOXP1, ESRRB, NFIB, ETS2, HES1, ELF1, ZIC1, SALL4, TFAP2A, HSF1, HEY1, HHEX, TGIF1, THAP11, ETS1, ARNT2, IRF4, CUX1, GRHL2, HOXA9, TBX2, TBX5, and ELF5 are introduced into a human pluripotent stem cell.

Example 34

(Differentiation into Smooth Muscle)

In this Example, a human embryonic stem cell can be differentiated into a smooth muscle, in particular, a cell present in the smooth muscle by introducing, into the human embryonic stem cell, a transcription factor cocktail selected from the human gene expression correlation matrix of Example 1 of the present invention by the method described in Example 2 of the present invention.

A method for differentiation into the smooth muscle of the present invention is as described below.

JUN, FOSL1, FOS, GADD45A, FOSL2, HSF1, JUNB, CUX1, IRF5, GATA3, and ETS2 are introduced into a human pluripotent stem cell.

Example 35

(Differentiation into Lung)

In this Example, a human embryonic stem cell can be differentiated into the lung, in particular, a cell present in the lung by introducing, into the human embryonic stem cell, a transcription factor cocktail selected from the human gene expression correlation matrix of Example 1 of the present invention by the method described in Example 2 of the present invention.

A method for differentiation into the lung (in particular, the lung, a bronchial epithelial cell, the fetal lung, or the trachea) of the present invention is as described below.

Lung: SALL4, TGIF1, FOS, TP73, NFIB, TFAP2C, ESX1, DLX6, PITX2, TFE3, JUNB, FOXP1, ZNF281, CEBPB, ZIC1, IRF5, CTCFL, HOXA9, FOSL1, TCF4, GATA3, ETS2, EGFLAM, ARID3A, KLF4, FOSL2, HHEX, ETS1, ELF1, ESRRB, IRF4, NRF1, HES1, GRHL2, FOXG1, ELF5, PRDM1, RFX2, JUN, HNF4A, TFAP2A, ERG, ARNT2, and HEY1 are introduced into a human pluripotent stem cell.

Bronchial epithelial cell: GADD45A, JUN, FOSL1, MYC, CUX1, IRF5, ESRRB, FOS, L3MBTL2, TRPV2, and FOSL2 are introduced into a human pluripotent stem cell.

Fetal lung: CEBPB, GATA3, ESX1, NFIB, JUNB, IRF5, JUN, ETS2, HSF1, ESRRB, FOSL1, TGIF1, TBX2, TFAP2C, FOS, and HNF4A are introduced into a human pluripotent stem cell.

Trachea: JUNB, HES1, TP73, TFAP2C, ESX1, CEBPB, GATA3, ELF1, FOXA2, FOS, IRF5, HEY1, NFIB, IRF4, ZIC1, FOXA1, NFIC, TBX5, CTCF, ESRRB, E2F6, FOSL1, HSF1, and IRF1 are introduced into a human pluripotent stem cell.

(General Remark)

In Examples of the present invention, human embryonic stem cells can be differentiated into desired cell types by introducing, into the human embryonic stem cells, the transcription factor cocktails selected from the human gene expression correlation matrix of Example 1 of the present invention by the method described in Example 2 of the present invention.

INDUSTRIAL APPLICABILITY

According to the present invention, the novel method of differentiating a pluripotent stem cell into a desired cell type can be provided.

The invention claimed is:

1. A method of differentiating a pluripotent stem cell into a hematopoietic stem cell and/or a blood cell, comprising a step of introducing only SPI1 as a transcription factor into a pluripotent stem cell of mammalian origin.

2. A method of differentiating a pluripotent stem cell into a hematopoietic stem cell and/or a blood cell, comprising a step of introducing one or more transcription factors of CDYL2, ETS2, CEBPB and SALL4 into a pluripotent stem cell of mammalian origin.

3. The method according to claim 2, wherein the transcription factor is CDYL2.

4. The method according to claim 2, wherein the transcription factor is ETS2.

5. The method according to claim 2, wherein the transcription factor is CEBPB.

6. The method according to claim 2, wherein the transcription factor is SALL4.

* * * * *

SEQUENCE LISTING

```
Sequence total quantity: 34
SEQ ID NO: 1            moltype = DNA  length = 1071
FEATURE                 Location/Qualifiers
source                  1..1071
                        mol_type = genomic DNA
                        organism = Homo sapiens
SEQUENCE: 1
atgaccaaat cgtacagcga gagtgggctg atgggcgagc ctcagcccca aggtcctcca  60
agctggacag acgagtgtct cagttctcag gacgaggagc acgaggcaga caagaaggag  120
gacgacctcg aaaccatgaa cgcagaggag gactcactga ggaacggggg agaggaggag  180
gacgaagatg aggacctgga agaggaggaa gaagaggaag aggaggatga cgatcaaaag  240
cccaagagac gcggccccaa aaagaagaag atgactaagg ctcgcctgga gcgttttaaa  300
ttgagacgca tgaaggctaa cgcccgggag cggaaccgca tgcacggact gaacgcggcg  360
ctagacaacc tgcgcaaggt ggtgccttgc tattctaaga cgcagaagct gtccaaaatc  420
gagactctgc gcttggccaa gaactacatc tgggctctgt cggagatcct gcgctcaggc  480
```

```
aaaagcccag acctggtctc cttcgttcag acgctttgca agggcttatc ccaacccacc  540
accaacctgg ttgcgggctg cctgcaactc aatcctcgga cttttctgcc tgagcagaac  600
caggacatgc ccccccacct gccgacggcc agcgcttcct tccctgtaca cccctactcc  660
taccagtcgc ctgggctgcc cagtccgcct tacggtacca tggacagctc ccatgtcttc  720
cacgttaagc ctccgccgca cgcctacagc gcagcgctgg agcccttctt tgaaagccct  780
ctgactgatt gcaccagccc ttcctttgat ggacccctca gcccgccgct cagcatcaat  840
ggcaacttct ctttcaaaca cgaaccgtcc gccgagtttg agaaaaatta tgcctttacc  900
atgcactatc ctgcagcgac actggcaggg gcccaaagcc acggatcaat cttctcaggc  960
accgctgccc ctcgctgcga gatccccata gacaatatta tgtccttcga tagccattca  1020
catcatgagc gagtcatgag tgcccagctc aatgccatat ttcatgatta g           1071

SEQ ID NO: 2            moltype = AA  length = 356
FEATURE                 Location/Qualifiers
source                  1..356
                        mol_type = protein
                        organism = Homo sapiens
SEQUENCE: 2
MTKSYSESGL MGEPQPQGPP SWTDECLSSQ DEEHEADKKE DDLETMNAEE DSLRNGGEEE  60
DEDEDLEEEE EEEEEDDDQK PKRRGPKKKK MTKARLERFK LRRMKANARE RNRMHGLNAA  120
LDNLRKVVPC YSKTQKLSKI ETLRLAKNYI WALSEILRSG KSPDLVSFVQ TLCKGLSQPT  180
TNLVAGCLQL NPRTFLPEQN QDMPPHLPTA SASFPVHPYS YQSPGLPSPP YGTMDSSHVF  240
HVKPPPHAYS AALEPFFESP LTDCTSPSFD GPLSPPLSIN GNFSFKHEPS AEFEKNYAFT  300
MHYPAATLAG AQSHGSIFSG TAAPRCEIPI DNIMSFDSHS HHERVMSAQL NAIFHD      356

SEQ ID NO: 3            moltype = DNA  length = 1149
FEATURE                 Location/Qualifiers
source                  1..1149
                        mol_type = genomic DNA
                        organism = Homo sapiens
SEQUENCE: 3
atgctgaccc gcctgttcag cgagcccggc cttctctcgg acgtgcccaa gttcgccagc  60
tggggcgacg gcgaagacga cgagccgagg agcgacaagg gcgacgcgcc gccaccgcca  120
ccgcctgcgc ccgggccagg ggctccgggg ccagcccggg cggccaagcc agtccctctc  180
cgtggagaag aggggacgga ggccacgttg gccgaggtca aggaggaagg cgagctgggg  240
ggagaggagg aggaggaaga ggaggaggaa gaaggactgg acgaggcgga gggcgagcgg  300
cccaagaagc gcgggcccaa gaagcgcaag atgaccaagg cgcgcttgga gcgctccaag  360
cttcggcggc agaaggcgaa cgcgcgggag cgcaaccgca tgcacgacct gaacgcagcc  420
ctggacaacc tgcgcaaggt ggtgccctgc tactccaaga cgcagaagct gtccaagatc  480
gagacgctgc gcctagccaa gaactatatc tgggcgctct cggagatcct gcgctccggc  540
aagcggccag acctagtgtc ctacgtgcag actctgtgca agggtctgtc gcagcccacc  600
accaatctgg tggccggctg tctgcagctc aactctcgca acttcctcac ggagcaaggc  660
gccgacggtg ccggccgctt ccacggctcg ggcggcccgt tcgccatgca cccctacccg  720
tacccgtgct cgcgcctggc gggcgcacag tgccaggcgg ccggcggcct gggcggcggc  780
gcggcgcacg ccctgcggac ccacggctac tgcgccgcct acgagacgct gtatgcggcg  840
gcaggcggtg gcggcgcgag cccggactac aacagctccg agtacgaggg cccgctcagc  900
cccccgctct gtctcaatgg caacttctca ctcaagcagg actcctcgcc cgaccacgag  960
aaaagctacc actactctat gcactactcg gcgctgcccg gttcgcggcc cacgggccac  1020
gggctagtct tcggctcgtc ggctgtgcgc gggggcgtcc actcggagaa tctcttgtct  1080
tacgatatgc accttcacca cgaccggggc cccatgtacg aggagctcaa tgcgtttttt  1140
cataactga                                                          1149

SEQ ID NO: 4            moltype = AA  length = 382
FEATURE                 Location/Qualifiers
source                  1..382
                        mol_type = protein
                        organism = Homo sapiens
SEQUENCE: 4
MLTRLFSEPG LLSDVPKFAS WGDGEDDEPR SDKGDAPPPP PPAPGPGAPG PARAAKPVPL  60
RGEEGTEATL AEVKEEGELG GEEEEEEEEE EGLDEAEGER PKKRGPKKRK MTKARLERSK  120
LRRQKANARE RNRMHDLNAA LDNLRKVVPC YSKTQKLSKI ETLRLAKNYI WALSEILRSG  180
KRPDLVSYVQ TLCKGLSQPT TNLVAGCLQL NSRNFLTEQG ADGAGRFHGS GGPFAMHPYP  240
YPCSRLAGAQ CQAAGGLGGG AAHALRTHGY CAAYETLYAA AGGGGASPDY NSSEYEGPLS  300
PPLCLNGNFS LKQDSSPDHE KSYHYSMHYS ALPGSRPTGH GLVFGSSAVR GGVHSENLLS  360
YDMHLHHDRG PMYEELNAFF HN                                           382

SEQ ID NO: 5            moltype = DNA  length = 714
FEATURE                 Location/Qualifiers
source                  1..714
                        mol_type = genomic DNA
                        organism = Homo sapiens
SEQUENCE: 5
atgccagccc gccttgagac ctgcatctcc gacctcgact gcgccagcag cagcggcagt  60
gacctatccg gcttcctcac cgacgaggaa gactgtgcca gactccaaca ggcagcctcc  120
gcttcggggc cgcccgcgcc ggcccgcagg ggcgcgccca atatctcccg ggcgtctgag  180
gttccagggg cacaggacga cgagcaggag aggcggcggc gccgcggccg gacgcgggtc  240
cgctccgagg cgctgctgca ctcgctgcgc aggagccggc gcgtcaaggc caacgatcgc  300
gagcgcaacc gcatgcacaa cttgaacgcg gccctggacg cactgcgcag cgtgctgccc  360
tcgttccccg acgacaccaa gctcaccaaa atcgagacgc tgcgcttcgc ctacaactac  420
atctgggctc tggccgagac actgcgcctg gcggatcaag ggctgcccgg aggcggtgcc  480
```

```
cgggagcgcc tcctgccgcc gcagtgcgtc ccctgcctgc ccggtccccc aagccccgcc  540
agcgacgcgg agtcctgggg ctcaggtgcc gccgccgcct ccccgctctc tgaccccagt  600
agcccagccg cctccgaaga cttcacctac cgcccccggcg accctgtttt ctccttccca  660
agcctgccca aagacttgct ccacacaacg ccctgtttca ttccttacca ctag        714

SEQ ID NO: 6            moltype = AA  length = 237
FEATURE                 Location/Qualifiers
source                  1..237
                        mol_type = protein
                        organism = Homo sapiens
SEQUENCE: 6
MPARLETCIS DLDCASSSGS DLSGFLTDEE DCARLQQAAS ASGPPAPARR GAPNISRASE  60
VPGAQDDEQE RRRRRGRTRV RSEALLHSLR RSRRVKANDR ERNRMHNLNA ALDALRSVLP  120
SFPDDTKLTK IETLRFAYNY IWALAETLRL ADQGLPGGGA RERLLPPQCV PCLPGPPSPA  180
SDAESWGSGA AAASPLSDPS SPAASEDFTY RPGDPVFSFP SLPKDLLHTT PCFIPYH     237

SEQ ID NO: 7            moltype = DNA  length = 819
FEATURE                 Location/Qualifiers
source                  1..819
                        mol_type = genomic DNA
                        organism = Homo sapiens
SEQUENCE: 7
atgttcgtca aatccgagac cttggagttg aaggaggaag aggacgtgtt agtgctgctc  60
ggatcggcct cccccgcctt ggcggccctg accccgctgt catccagcgc cgacgaagaa  120
gaggaggagg agccgggcgc gtcaggcggg gcgcgtcggc agcgcggggc tgaggccggg  180
cagggggcgc ggggcggcgt ggctgcgggt gcggagggct gccggcccgc acggctgctg  240
ggtctggtac acgattgcaa acggcgccct tcccgggcgc gggccgtctc ccgaggcgcc  300
aagacggccg agacggtgca gcgcatcaag aagacccgta gactgaaggc caacaaccgc  360
gagcgaaacc gcatgcacaa cctcaacgcg gcactggacg cgctgcgcga ggtgctcccc  420
acgttccccg aggacgccaa gctcaccaag atcgagaccc tgcgcttcgc ccacaactac  480
atctgggcac tcaccgagac cctgcgcctg gcggatcact gcgggggcgg cggcgggggc  540
ctgccggggg cgctcttctc cgaggcagtg ttgctgagcc cgggaggagc cagcgccgcc  600
ctgagcagca gcggagacag cccctcgccc gcctccacgt ggagttgcac caacagcccc  660
gcgccgtcct cctccgtgtc ctccaattcc acctccccct acagctgcac tttatcgccc  720
gccagcccgg ccgggtcaga catggactat tggcagcccc cacctcccga caagcaccgc  780
tatgcacctc acctccccat agccagggat tgtatctag                         819

SEQ ID NO: 8            moltype = AA  length = 272
FEATURE                 Location/Qualifiers
source                  1..272
                        mol_type = protein
                        organism = Homo sapiens
SEQUENCE: 8
MFVKSETLEL KEEEDVLVLL GSASPALAAL TPLSSSADEE EEEPGASGG ARRQRGAEAG  60
QGARGGVAAG AEGCRPARLL GLVHDCKRRP SRARAVSRGA KTAETVQRIK KTRRLKANNR  120
ERNRMHNLNA ALDALREVLP TFPEDAKLTK IETLRFAHNY IWALTETLRL ADHCGGGGGG  180
LPGALFSEAV LLSPGGASAA LSSSGDSPSP ASTWSCTNSP APSSSVSSNS TSPYSCTLSP  240
ASPAGSDMDY WQPPPPDKHR YAPHLPIARD CI                                272

SEQ ID NO: 9            moltype = DNA  length = 645
FEATURE                 Location/Qualifiers
source                  1..645
                        mol_type = genomic DNA
                        organism = Homo sapiens
SEQUENCE: 9
atgacgcctc aaccctcggg tgcgcccact gtccaagtga cccgtgagac ggagcggtcc  60
ttccccagag cctcggaaga cgaagtgacc tgccccacgt ccgcccccgcc cagccccact  120
cgcacacggg ggaactgcgc agaggcggaa gagggaggct gccgaggggc cccgaggaag  180
ctccgggcac ggcgcggggg acgcagccgg cctaagagcg agttggcact gagcaagcag  240
cgacggagtc ggcgaaagaa ggccaacgac cgcgagcgca atcgaatgca caacctcaac  300
tcggcactgg acgccctgcg cggtgtcctg cccaccttcc cagacgacgc gaagctcacc  360
aagatcgaga cgctgcgctt cgcccacaac tacatctggg cgctgactca aacgctgcgc  420
atagcggacc acagcttgta cgcgctggag ccgccggcgc cgcactgcgg ggagctgggc  480
agcccaggcg gttcccccgg ggactggggg tccctctact ccccagtctc ccaggctggc  540
agcctgagtc ccgccgcgtc gctggaggag cgacccgggc tgctgggggc caccttttcc  600
gcctgcttga gcccaggcag tctggctttc tcagattttc tgtga                  645

SEQ ID NO: 10           moltype = AA  length = 214
FEATURE                 Location/Qualifiers
source                  1..214
                        mol_type = protein
                        organism = Homo sapiens
SEQUENCE: 10
MTPQPSGAPT VQVTRETERS FPRASEDEVT CPTSAPPSPT RTRGNCAEAE EGGCRGAPRK  60
LRARRGGRSR PKSELALSKQ RRSRRKKAND RERNRMHNLN SALDALRGVL PTFPDDAKLT  120
KIETLRFAHN YIWALTQTLR IADHSLYALE PPAPHCGELG SPGGSPGDWG SLYSPVSQAG  180
SLSPAASLEE RPGLLGATFS ACLSPGSLAF SDFL                              214

SEQ ID NO: 11           moltype = DNA  length = 819
```

```
FEATURE                Location/Qualifiers
source                 1..819
                       mol_type = genomic DNA
                       organism = Homo sapiens
SEQUENCE: 11
atgaaaggca agaaaggtat tgttgcagca tctggcagtg agactgagga tgaggacagc  60
atggacattc ccttggacct ttcttcatcc gctggctcag gcaagagaag gagaaggggc  120
aacctaccca aggagtctgt gcagattctt cgggattggc tgtatgagca ccgttacaat  180
gcctatcctt cagagcaaga aaaagcgttg ctgtcccagc aaacacacct gtctacgcta  240
caggtctgta actggttcat caacgcccgc cgcaggctcc tccctgacat gctgagaaag  300
gatggcaaag atccaaatca gttcacaatt tcccgccgtg ggccaagat ttctgaaacg  360
agctctgtgg agtccgtgat gggcatcaaa aacttcatgc cagctctaga ggagacccca  420
tttcattcct gtacagctgg gccaaaccca accctaggga ggccactgtc tcctaagccg  480
tcatccccgg gatcagtttt ggctcgtcca tcagtgatct gccataccac tgtgactgca  540
ttgaaagatg tccctttctc tctctgccag tcggtcggtg tgggacaaaa cacagatata  600
cagcagatag cggccaaaaa cttcacagac acctctctca tgtacccaga ggacacttgt  660
aaatctggac caagtacgaa tacacagagt ggtcttttca acactcctcc ccctactcca  720
ccggacctca accaggactt cagtggattt cagcttctag tggatgttgc actcaaacgg  780
gctgcagaga tggagcttca ggcaaaactt acagcttaa                        819

SEQ ID NO: 12          moltype = AA  length = 272
FEATURE                Location/Qualifiers
source                 1..272
                       mol_type = protein
                       organism = Homo sapiens
SEQUENCE: 12
MKGKKGIVAA SGSETEDEDS MDIPLDLSSS AGSGKRRRRG NLPKESVQIL RDWLYEHRYN  60
AYPSEQEKAL LSQQTHLSTL QVCNWFINAR RRLLPDMLRK DGKDPNQFTI SRRGAKISET  120
SSVESVMGIK NFMPALEETP FHSCTAGPNP TLGRPLSPKP SSPGSVLARP SVICHTTVTA  180
LKDVPFSLCQ SVGVGQNTDI QQIAAKNFTD TSLMYPEDTC KSGPSTNTQS GLFNTPPPTP  240
PDLNQDFSGF QLLVDVALKR AAEMELQAKL TA                                272

SEQ ID NO: 13          moltype = DNA  length = 2016
FEATURE                Location/Qualifiers
source                 1..2016
                       mol_type = genomic DNA
                       organism = Homo sapiens
SEQUENCE: 13
atgcatcacc aacagcgaat ggctgcctta gggacggaca aagagctgag tgatttactg  60
gatttcagtg cgatgttttc acctcctgtg agcagtggga aaaatggacc aacttctttg  120
gcaagtggac attttactgg ctcaaatgta gaagacagaa gtagctcagg gtcctggggg  180
aatggaggac atccaagccc gtccaggaac tatggagatg ggactcccta tgaccacatg  240
accagcaggg accttgggtc acatgacaat ctctctccac cttttgtcaa ttccagaata  300
caaagtaaaa cagaaagggg ctcatactca tcttatggga gagaatcaaa cttacagggt  360
tgccaccagc agagtctcct tggaggtgac atggatatgg gcaacccagg aaccctttcg  420
cccaccaaac ctggttccca gtactatcag tattctagca ataatccccg aaggaggcct  480
cttcacagta gtgccatgga ggtacagaca aagaaagttc gaaaagttcc tccaggtttg  540
ccatcttcag tctatgctcc atcagcaagc actgccgact acaataggga ctcgccaggc  600
tatccttcct ccaaaccagc aaccagcact ttccctagct ccttcttcat gcaagatggc  660
catcacagca gtgaccctttg gagctcctcc agtgggatga atcagcctgg ctatgcagga  720
atgttgggca actcttctca tattccacag tccagcagct actgtagcct gcatccacat  780
gaacgtttga gctatccatc acactcctca gcagacatca attccagtct tcctccgatg  840
tccactttcc atcgtagtgg tacaaaccat tacagcacct cttcctgtac gcctcctgcc  900
aacgggacag acagtataat ggcaaataga ggaagcgggg cagccggcag ctcccagact  960
ggagatgctc tggggaaagc acttgcttcg atctattctc cagatcacac taacaacagc  1020
ttttcatcaa acccttcaac tcctgttggc tctcctccat ctctctcagc aggcacagct  1080
gtttggtcta gaaatggagg acaggcctca tcgtctccta attatgaagg acccttacac  1140
tctttgcaaa gccgaattga agatcgttta gaaagactgg atgatgctat tcatgttctc  1200
cggaaccatg cagtgggccc atccacagct atgcctggtg gtcatgggga catgcatgga  1260
atcattggac cttctcataa tggagccatg ggtggtctgg gctcagggta tggaaccggc  1320
cttctttcag ccaacagaca ttcactcatg gtggggaccc atcgtgaaga tggcgtggcc  1380
ctgagaggca gccattctct tctgccaaac caggttccgg ttccacagct tcctgtccag  1440
tctgcgactt cccctgacct gaacccaccc caggaccctt acagaggcat gccaccagga  1500
ctacaggggc agagtgtctc ctctggcagc tctgagatca aatccgatga cgagggtgat  1560
gagaacctgc aagacacgaa atcttcggag gacaagaaat tagatgacga caagaaggat  1620
atcaaatcaa ttactaggtc aagatctagc aataatgacg atgaggacct gacaccagag  1680
cagaaggcag agcgtgagaa ggagcggagg atggccaaca atgcccgaga gcgtctgcgg  1740
gtccgtgaca tcaacgaggc tttcaaagag ctcggccgca tggtgcagct ccacctcaag  1800
agtgacaagc cccagaccaa gctcctgatc ctccaccagg cggtggccgt catcctcagt  1860
ctggagcagc aagtccgaga aaggaatctg aatccgaaag ctgcgtgtct gaaaagaagg  1920
gaggaagaga aggtgtcctc agagcctccc cctctctcct tggccggccc acaccctgga  1980
atgggagacg catcgaatca catgggacag atgtaa                            2016

SEQ ID NO: 14          moltype = AA  length = 671
FEATURE                Location/Qualifiers
source                 1..671
                       mol_type = protein
                       organism = Homo sapiens
SEQUENCE: 14
```

```
MHHQQRMAAL GTDKELSDLL DFSAMFSPPV SSGKNGPTSL ASGHFTGSNV EDRSSSGSWG  60
NGGHPSPSRN YGDGTPYDHM TSRDLGSHDN LSPPFVNSRI QSKTERGSYS SYGRESNLQG  120
CHQQSLLGGD MDMGNPGTLS PTKPGSQYYQ YSSNNPRRRP LHSSAMEVQT KKVRKVPPGL  180
PSSVYAPSAS TADYNRDSPG YPSSKPATST FPSSFFMQDG HHSSDPWSSS SGMNQPGYAG  240
MLGNSSHIPQ SSSYCSLHPH ERLSYPSHSS ADINSSLPPM STFHRSGTNH YSTSSCTPPA  300
NGTDSIMANR GSGAAGSSQT GDALGKALAS IYSPDHTNNS FSSNPSTPVG SPPSLSAGTA  360
VWSRNGGQAS SSPNYEGPLH SLQSRIEDRL ERLDDAIHVL RNHAVGPSTA MPGGHGDMHG  420
IIGPSHNGAM GGLGSGYGTG LLSANRHSLM VGTHREDGVA LRGSHSLLPN QVPVPQLPVQ  480
SATSPDLNPP QDPYRGMPPG LQGQSVSSGS SEIKSDDEGD ENLQDTKSSE DKKLDDDKKD  540
IKSITRSRSS NNDDEDLTPE QKAEREKERR MANNARERLR VRDINEAFKE LGRMVQLHLK  600
SDKPQTKLLI LHQAVAVILS LEQQVRERNL NPKAACLKRR EEEKVSSEPP PLSLAGPHPG  660
MGDASNHMGQ M                                                    671

SEQ ID NO: 15          moltype = DNA  length = 975
FEATURE                Location/Qualifiers
source                 1..975
                       mol_type = genomic DNA
                       organism = Homo sapiens
SEQUENCE: 15
atgaactgca tgaaaggccc gcttcacttg gagcaccgag cagcggggac caagctgtcg  60
gccgtctcct catcttcctg tcaccatccc cagccgttag ccatggcttc ggttctggct  120
cccggtcagc cccggtcgct ggactcctcc aagcacaggc tggaggtgca caccatctcc  180
gacacctcca gccccggaggc cgcagagaaa gataaaagcc agcaggggaa gaatgaggac  240
gtgggcgccg aggacccgtc taagaagaag cggcaaaggc ggcagcggac tcactttacc  300
agccagcagc tccaggagct ggaggccact ttccagagga accgctaccc ggacatgtcc  360
acacgcgaag aaatcgctgt gtggaccaac cttacggaag cccgagtccg ggtttggttc  420
aagaatcgtc gggccaaatg gagaaagagg gagcgcaacc agcaggccga gctatgcaag  480
aatggcttcg ggccgcagtt caatgggctc atgcagccct acgacgacat gtacccaggc  540
tattcctaca acaactgggc cgccaagggc cttacatccg cctccctatc caccaagagc  600
ttccccttct tcaactctat gaacgtcaac cccctgtcat cacagagcat gttttcccca  660
cccaactcta tctcgtccat gagcatgtcg tccagcatgg tgccctcagc agtgacaggc  720
gtcccgggct ccagtctcaa cagcctgaat aacttgaaca acctgagtag cccgtcgctg  780
aattccgcgg tgccgacgcc tgcctgtcct tacgcgccgc cgactcctcc gtatgtttat  840
agggacacgt gtaactcgag cctggccagc ctgagactga aagcaaagca gcactccagc  900
ttcggctacg ccagcgtgca gaacccggcc tccaacctga gtgcttgcca gtatgcagtg  960
gaccggcccg tgtga                                                  975

SEQ ID NO: 16          moltype = AA  length = 324
FEATURE                Location/Qualifiers
source                 1..324
                       mol_type = protein
                       organism = Homo sapiens
SEQUENCE: 16
MNCMKGPLHL EHRAAGTKLS AVSSSSCHHP QPLAMASVLA PGQPRSLDSS KHRLEVHTIS  60
DTSSPEAAEK DKSQQGKNED VGAEDPSKKK RQRRQRTHFT SQQLQELEAT FQRNRYPDMS  120
TREEIAVWTN LTEARVRVWF KNRRAKWRKR ERNQQAELCK NGFGPQFNGL MQPYDDMYPG  180
YSYNNWAAKG LTSASLSTKS FPFFNSMNVN PLSSQSMFSP PNSISSMSMS SSMVPSAVTG  240
VPGSSLNSLN NLNNLSSPSL NSAVPTPACP YAPPTPPYVY RDTCNSSLAS LRLKAKQHSS  300
FGYASVQNPA SNLSACQYAV DRPV                                        324

SEQ ID NO: 17          moltype = DNA  length = 3162
FEATURE                Location/Qualifiers
source                 1..3162
                       mol_type = genomic DNA
                       organism = Homo sapiens
SEQUENCE: 17
atgtcgaggc gcaagcaggc gaaaccccag cacatcaact cggaggagga ccagggcgag  60
cagcagccgc agcagcagac cccggagttt gcagatgcgg ccccagcggc gccccgcggcg  120
ggggagctgg gtgctccagt gaaccaccca gggaatgacg aggtggcgag tgaggatgaa  180
gccacagtaa agcggcttcg tcgggaggag acgcacgtct gtgagaaatg ctgtgcggag  240
ttcttcagca tctctgagtt cctggaacat aagaaaaatt gcactaaaaa tccacctgtc  300
ctcatcatga atgacagcga ggggcctgtg ccttcagaag acttctccgg agctgtactg  360
agccaccagc ccaccagtcc cggcagtaag gactgtcaca gggagaatgg cggcagctca  420
gaggacatga aggagaagcc ggatgcggag tctgtggtgt acctaaagac agagacagcc  480
ctgccaccca ccccccagga cataagctat ttagccaaag gcaaagtggc caacactaat  540
gtgaccttgc aggcactacg gggcaccaag gtggcggtga atcagcggag cgcggatgca  600
ctccctgccc ccgtgcctgg tgccaacagc atcccgtggg tcctcgagca gatcttgtgt  660
ctgcagcagc agcagctaca gcagatccag ctcaccgagc agatccgcat ccaggtgaac  720
atgtgggcct cccacgccct ccactcaagc ggggcagggg ccgacactct gaagaccttg  780
ggcagccaca tgtctcagca ggtttctgca gctgtggctt tgctcagcca gaaagctgga  840
agccaaggtc tgtctctgga tgccttgaaa caagccaagc tacctcacgc caacatccct  900
tctgccacca gctccctgtc cccagggctg gcaccccttca ctctgaagcc ggatgggacc  960
cgggtgctcc cgaacgtcat gtcccgcctc ccgagcgctt tgcttcctca ggccccgggc  1020
tcggtgctct tccagagccc tttctccact gtggcgctag acacatccaa gaaagggaag  1080
gggaagccac cgaacatctc cgcggtggat gtcaaaccca aagacgaggc ggccctctac  1140
aagcacaagt gtaagtactg tagcaaggtt tttgggactg atagctcctt gcagatccac  1200
ctccgctccc acactggaga gagacccttc gtgtgctctg tctgtggtca tcgcttcacc  1260
accaagggca acctcaaggt gcactttcac cgacatcccc aggtgaaggc aaacccccag  1320
ctgtttgccg agttccagga caaagtggcg gccggcaatg gcatccccta tgcactctct  1380
```

```
gtacctgacc ccatagatga accgagtctt tctttagaca gcaaacctgt ccttgtaacc  1440
acctctgtag ggctacctca gaatctttct tcggggacta atcccaagga cctcacgggt  1500
ggctccttgc ccggtgacct gcagcctggg ccttctccag aaagtgaggg tggacccaca  1560
ctccctgggg tgggaccaaa ctataattcc ccaagggctg gtggcttcca agggagtggg  1620
acccctgagc cagggtcaga gaccctgaaa ttgcagcagt tggtggagaa cattgacaag  1680
gccaccactg atcccaacga atgtctcatt tgccaccgag tcttaagctg tcagagctcc  1740
ctcaagatgc attatcgcac ccacaccggg gagagaccgt tccagtgtaa gatctgtggc  1800
cgagcctttt ctaccaaagg taacctgaag acacaccttg ggttcaccg aaccaacaca  1860
tccattaaga cgcagcattc gtgccccatc tgccagaaga agttcactaa tgccgtgatg  1920
ctgcagcaac atattcggat gcacatgggc ggtcagattc ccaacacgcc cctgccagag  1980
aatccctgtg actttacggg ttctgagcca atgaccgtgg gtgagaacgg cagcaccggc  2040
gctatctgcc atgatgatgt catcgaaagc atcgatgtag aggaagtcag ctcccaggag  2100
gctcccagca gctcctccaa ggtccccacg cctcttccca gcatccactc ggcatcaccc  2160
acgctagggt ttgccatgat ggcttcctta gatgccccag ggaaagtggg tcctgcccct  2220
tttaacctgc agcgccaggg cagcagagaa aacggttccg tggagagcga tggcttgacc  2280
aacgactcat cctcgctgat gggagaccag gagtatcaga gccgaagccc agatatcctg  2340
gaaaccacat ccttccaggc actctccccg gccaatagtc aagccgaaag catcaagtca  2400
aagtctcccg atgctgggag caaagcagag agctccgaga acagccgcac tgagatggaa  2460
ggtcggagca gtctcccttc cacgtttatc cgagccccgc cgacctatgt caaggttgaa  2520
gttcctggca catttgtggg accctcgaca ttgtccccag ggatgacccc tttgttagca  2580
gcccagccac gccgacaggc caagcaacat ggctgcacac ggtgtgggaa gaacttctcg  2640
tctgctagcg ctcttcagat ccacgagcgg actcacactg gagagaagcc ttttgtgtgc  2700
aacatttgtg ggcgagcttt taccaccaaa ggcaacttaa aggttcacta catgacacac  2760
ggggcgaaca ataactcagc ccgccgtgga aggaagttgg ccatcgagaa caccatggct  2820
ctgttaggta cggacggaaa aagagtctca gaaatctttc ccaaggaaat cctggcccct  2880
tcagtgaatg tggaccctgt tgtgtggaac cagtacacca gcatgctcaa tggcggtctg  2940
gccgtgaaga ccaatgagat ctctgtgatc cagagtgggg gggttcctac cctcccggtt  3000
tccttggggg ccacctccgt tgtgaataac gccactgtct ccaagatgga tggctcccag  3060
tcgggtatca gtgcagatgt ggaaaaacca agtgctactg acggcgttcc caaacaccag  3120
tttcctcact tcctggaaga aaacaagatt gcggtcagct aa                      3162
```

```
SEQ ID NO: 18           moltype = AA  length = 1053
FEATURE                 Location/Qualifiers
source                  1..1053
                        mol_type = protein
                        organism = Homo sapiens
SEQUENCE: 18
MSRRKQAKPQ HINSEEDQGE QQPQQQTPEF ADAAPAAPAA GELGAPVNHP GNDEVASEDE  60
ATVKRLRREE THVCEKCCAE FFSISEFLEH KKNCTKNPPV LIMNDSEGPV PSEDFSGAVL  120
SHQPTSPGSK DCHRENGGSS EDMKEKPDAE SVVYLKTETA LPPTPQDISY LAKGKVANTN  180
VTLQALRGTK VAVNQRSADA LPAPVPGANS IPWVLEQILC LQQQQLQQIQ LTEQIRIQVN  240
MWASHALHSS GAGADTLKTL GSHMSQQVSA AVALLSQKAG SQGLSLDALK QAKLPHANIP  300
SATSSLSPGL APFTLKPDGT RVLPNVMSRL PSALLPQAPG SVLFQSPFST VALDTSKKGK  360
GKPPNISAVD VKPKDEAALY KHKCKYCSKV FGTDSSLQIH LRSHTGERPF VCSVCGHRFT  420
TKGNLKVHFH RHPQVKANPQ LFAEFQDKVA AGNGIPYALS VPDPIDEPSL SLDSKPVLVT  480
TSVGLPQNLS SGTNPKDLTG GSLPGDLQPG PSPESEGGPT LPGVGPNYNS PRAGGFQGSG  540
TPEPGSETLK LQQLVENIDK ATTDPNECLI CHRVLSCQSS LKMHYRTHTG ERPFQCKICG  600
RAFSTKGNLK THLGVHRTNT SIKTQHSCPI CQKKFTNAVM LQQHIRMHMG GQIPNTPLPE  660
NPCDFTGSEP MTVGENGSTG AICHDDVIES IDVEEVSSQE APSSSSKVPT PLPSIHSASP  720
TLGFAMMASL DAPGKVGPAP FNLQRQGSRE NGSVESDGLT NDSSSLMGDQ EYQSRSPDIL  780
ETTSFQALSP ANSQAESIKS KSPDAGSKAE SSENSRTEME GRSSLPSTFI RAPPTYVKVE  840
VPGTFVGPST LSPGMTPLLA AQPRRQAKQH GCTRCGKNFS SASALQIHER THTGEKPFVC  900
NICGRAFTTK GNLKVHYMTH GANNNSARRG RKLAIENTMA LLGTDGKRVS EIFPKEILAP  960
SVNVDPVVWN QYTSMLNGGL AVKTNEISVI QSGGVPTLPV SLGATSVVNN ATVSKMDGSQ  1020
SGISADVEKP SATDGVPKHQ FPHFLEENKI AVS                                1053
```

```
SEQ ID NO: 19           moltype = DNA  length = 1173
FEATURE                 Location/Qualifiers
source                  1..1173
                        mol_type = genomic DNA
                        organism = Homo sapiens
SEQUENCE: 19
atggcgcaaa ggtacgacga tctaccccat tacgggggca tggatggagt aggcatcccc  60
tccacgatgt atggggaccc gcatgcagcc aggtccatgc agccggtcca ccacctgaac  120
cacgggcctc ctctgcactc gcatcagtac ccgcacacag ctcataccaa cgccatggcc  180
cccagcatgg gctcctctgt caatgacgct ttaaagagag ataaagatgc catttatgga  240
caccccctct tccctctctt agcactgatt tttgagaaat gtgaattagc tacttgtacc  300
ccccgcgagc cgggggtggc gggcggggac gtctgctcgt cagagtcatt caatgaagat  360
atagccgtgt tcgccaaaca gattcgcgca gaaaaacctc tattttcttc taatccagaa  420
ctggataact tgatgattca agccatacaa gtattaaggt ttcatctatt ggaattagag  480
aaggtacacg aattatgtga caatttctgc caccggtata ttagctgttt gaaagggaaa  540
atgcctatcg atttggtgat agacgataga gaaggaggat caaaatcaga cagtgaagat  600
ataacaagat cagcaaatct aactgaccag ccctcttgga acagagatca tgatgacacg  660
gcatctactc gttcaggagg aaccccaggc ccttccagcg gtggccacac gtcacacagt  720
ggggacaaca gcagtgagca aggtgatggc ttggacaaca gtgtagcttc ccccagcaca  780
ggtgacgatg atgaccctga taaggacaaa aagcgtcaca aaaagcgtgg catctttccc  840
aaagtagcca caaatatcat gagggcgtgg ctgttccagc atctaacaca cccttaccct  900
tctgaagaac agaaaaagca gttggcacaa gacacgggac tcaccatcct tcaagtgaac  960
aattggttta ttaatgcccg gagaagaata gtgcagccca tgatagacca gtccaaccga  1020
```

```
gcagtaagtc aaggaacacc ttataatcct gatggacagc ccatgggagg tttcgtaatg  1080
gacggtcagc aacatatggg aattagagca ccaggaccta tgagtggaat gggcatgaat  1140
atgggcatgg aggggcagtg gcactacatg taa                                1173

SEQ ID NO: 20          moltype = AA  length = 390
FEATURE                Location/Qualifiers
source                 1..390
                       mol_type = protein
                       organism = Homo sapiens
SEQUENCE: 20
MAQRYDDLPH YGGMDGVGIP STMYGDPHAA RSMQPVHHLN HGPPLHSHQY PHTAHTNAMA  60
PSMGSSVNDA LKRDKDAIYG HPLFPLLALI FEKCELATCT PREPGVAGGD VCSSESFNED  120
IAVFAKQIRA EKPLFSSNPE LDNLMIQAIQ VLRFHLLELE KVHELCDNFC HRYISCLKGK  180
MPIDLVIDDR EGGSKSDSED ITRSANLTDQ PSWNRDHDDT ASTRSGGTPG PSSGGHTSHS  240
GDNSSEQGDG LDNSVASPST GDDDDPDKDK KRHKKRGIFP KVATNIMRAW LFQHLTHPYP  300
SEEQKKQLAQ DTGLTILQVN NWFINARRRI VQPMIDQSNR AVSQGTPYNP DGQPMGGFVM  360
DGQQHMGIRA PGPMSGMGMN MGMEGQWHYM                                    390

SEQ ID NO: 21          moltype = DNA  length = 1521
FEATURE                Location/Qualifiers
source                 1..1521
                       mol_type = genomic DNA
                       organism = Homo sapiens
SEQUENCE: 21
atggcttctg ggacctttta cgaggttgaa aggattgtag acaagaggaa gaacaagaaa  60
ggaaaaatggg agtatcttat ccgatggaaa ggctacggga gcaccgagga cacgtgggag  120
ccggagcacc acctcttgca ctgtgaggag tttattgatg aattcaatgg gttgcacatg  180
tccaaggaca agaggatcaa gtcagggaag cagtccagta cctccaagct gctgcgtgac  240
agtcgaggcc cgtcggttga gaaactgtcc cacagacctt cagatcctgg aaagagcaag  300
gggacctccc ataaacggaa gcgaattaac cctcccctgg ccaagccaaa aaaagggtat  360
tcaggcaagc cctcttcagg aggtgacagg gccaccaaga cggtgtctta caggactacc  420
cccagtggtt tgcaaataat gcccctgaaa aagtctcaga acgggatgga aaatggggac  480
gccggctctg agaaggatga gaggcacttt ggaaatgggt cccatcagcc tggcttggat  540
ttgaatgatc atgttggaga gcaagatatg ggtgaatgtg acgtgaatca cgctacactg  600
gcggagaacg ggctcggctc tgctctgacc aacgggggat tgaacctgca cagtccagtg  660
aagaggaagc tggaagcgga gaaggactac gtctttgaca aaaggctcag atacagtgtc  720
cgccagaatg aaagcaactg tcggtttcga gacatcgttg tgcggaagga agaagggttc  780
acgcacatcc tgctgtccag tcagacctcg gataacaatg ccctgacacc tgagatcatg  840
aaagaagtcc ggcgagcgct ctgcaacgca gccacagacg acagcaaact gctgctcctc  900
agcgcagtgg ggagcgtgtt ctgcagcggc ctggattatt cctacctaat tggccggttg  960
tccagcgacc ggcgaaagga gagcactcgg attgcagaag ccatcaggga ctttgtgaag  1020
gcctttatcc agtttaagaa gcctatcgtg gtggccatca atgggccggc cctgggcctg  1080
ggtgcctcca tcctgcccct ctgtgacatc gtgtgggcca gtgagaaggc ctggttccag  1140
acgccctacg ccaccatccg cctcacgcct gctggctgct cctcctacac cttcccccag  1200
atcctgggcg tcgcgctggc caatgagatg ctgttctgtg ggcggaagct caccgcccag  1260
gaggcctgca gcagggggct ggtgtcgcag gtcttctggc ccaccacgtt cagccaggag  1320
gtcatgctgc gggtcaagga gatggcatcc tgcagtgccg tggtgttaga ggagtccaaa  1380
tgcctcgtgc ggagcttcct gaaatcagtg ctggaagacg tgaacgagaa ggaatgcctc  1440
atgctcaagc agctctggag ctcctccaaa ggccttgact ccctttttcag ctacctgcag  1500
gacaaaattt atgaagtctg a                                             1521

SEQ ID NO: 22          moltype = AA  length = 506
FEATURE                Location/Qualifiers
source                 1..506
                       mol_type = protein
                       organism = Homo sapiens
SEQUENCE: 22
MASGDLYEVE RIVDKRKNKK GKWEYLIRWK GYGSTEDTWE PEHHLLHCEE FIDEFNGLHM  60
SKDKRIKSGK QSSTSKLLRD SRGPSVEKLS HRPSDPGKSK GTSHKRKRIN PPLAKPKKGY  120
SGKPSSGGDR ATKTVSYRTT PSGLQIMPLK KSQNGMENGD AGSEKDERHF GNGSHQPGLD  180
LNDHVGEQDM GECDVNHATL AENGLGSALT NGGLNLHSPV KRKLEAEKDY VFDKRLRYSV  240
RQNESNCRFR DIVVRKEEGF THILLSSQTS DNNALTPEIM KEVRRALCNA ATDDSKLLLL  300
SAVGSVFCSG LDYSYLIGRL SSDRRKESTR IAEAIRDFVK AFIQFKKPIV VAINGPALGL  360
GASILPLCDI VWASEKAWFQ TPYATIRLTP AGCSSYTFPQ ILGVALANEM LFCGRKLTAQ  420
EACSRGLVSQ VFWPTTFSQE VMLRVKEMAS CSAVVLEESK CLVRSFLKSV LEDVNEKECL  480
MLKQLWSSSK GLDSLFSYLQ DKIYEV                                        506

SEQ ID NO: 23          moltype = DNA  length = 1461
FEATURE                Location/Qualifiers
source                 1..1461
                       mol_type = genomic DNA
                       organism = Homo sapiens
SEQUENCE: 23
atgattcaga ctgtcccgga cccagcagct catatcaagg aagccttatc agttgtgagt  60
gaggaccagt cgttgtttga gtgtgcctac ggaacgccac acctggctaa gacagagatg  120
accgcgtcct cctccagcga ctatggacag acttccaaga tgagcccacg cgtccctcag  180
caggattggc tgtctcaacc cccagccagg gtcaccatca aaatggaatg taaccctagc  240
caggtgaatg gctcaaggaa ctctcctgat gaatgcagtg tggccaaagg cgggaagatg  300
gtgggcagcc cagacaccgt tgggatgaac tacggcagct acatggagga gaagcacatg  360
```

```
ccacccccaa acatgaccac gaacgagcgc agagttatcg tgccagcaga tcctacgcta  420
tggagtacag accatgtgcg gcagtggctg gagtgggcgg tgaaagaata tggccttcca  480
gacgtcaaca tcttgttatt ccagaacatc gatgggaagg aactgtgcaa gatgaccaag  540
gacgacttcc agaggctcac ccccagctac aacgccgaca tccttctctc acatctccac  600
tacctcagag agactcctct tccacatttg acttcagatg atgttgataa agccttacaa  660
aactctccac ggttaatgca tgctagaaac acagggggtg cagcttttat tttcccaaat  720
acttcagtat atcctgaagc tacgcaaaga attacaacta ggccagattt accatatgag  780
ccccccagga gatcagcctg gaccggtcac ggccacccca cgccccagtc gaaagctgct  840
caaccatctc cttccacagt gcccaaaact gaagaccagc gtcctcagtt agatccttat  900
cagattcttg gaccaacaag tagccgcctt gcaaatccag gcagtggcca gatccagctt  960
tggcagttcc tcctggagct cctgtcggac agctccaact ccagctgcat cacctgggaa  1020
ggcaccaacg gggagttcaa gatgacggat cccgacgagg tggcccggcg ctggggagag  1080
cggaagagca aacccaacat gaactacgat aagctcagcc gcgccctccg ttactactat  1140
gacaagaaca tcatgaccaa ggtccatggg aagcgctacg cctacaagtt cgacttccac  1200
gggatcgccc aggccctcca gccccacccc ccggagtcat ctctgtacaa gtacccctca  1260
gacctcccgt acatgggctc ctatcacgcc cacccacaga agatgaactt tgtggcgccc  1320
caccctccag ccctccccgt gacatcttcc agttttttg ctgccccaaa cccatactgg  1380
aattcaccaa ctgggggtat ataccccaac actaggctcc ccaccagcca tatgccttct  1440
catctgggca cttactacta a                                            1461
```

```
SEQ ID NO: 24          moltype = AA  length = 486
FEATURE                Location/Qualifiers
source                 1..486
                       mol_type = protein
                       organism = Homo sapiens
SEQUENCE: 24
MIQTVPDPAA HIKEALSVVS EDQSLFECAY GTPHLAKTEM TASSSSDYGQ TSKMSPRVPQ  60
QDWLSQPPAR VTIKMECNPS QVNGSRNSPD ECSVAKGGKM VGSPDTVGMN YGSYMEEKHM  120
PPPNMTTNER RVIVPADPTL WSTDHVRQWL EWAVKEYGLP DVNILLFQNI DGKELCKMTK  180
DDFQRLTPSY NADILLSHLH YLRETPLPHL TSDDVDKALQ NSPRLMHARN TGGAAFIFPN  240
TSVYPEATQR ITTRPDLPYE PPRRSAWTGH GHPTPQSKAA QPSPSTVPKT EDQRPQLDPY  300
QILGPTSSRL ANPGSGQIQL WQFLLELLSD SSNSSCITWE GTNGEFKMTD PDEVARRWGE  360
RKSKPNMNYD KLSRALRYYY DKNIMTKVHG KRYAYKFDFH GIAQALQPHP PESSLYKYPS  420
DLPYMGSYHA HPQKMNFVAP HPPALPVTSS SFFAAPNPYW NSPTGGIYPN TRLPTSHMPS  480
HLGTYY                                                             486
```

```
SEQ ID NO: 25          moltype = DNA  length = 816
FEATURE                Location/Qualifiers
source                 1..816
                       mol_type = genomic DNA
                       organism = Homo sapiens
SEQUENCE: 25
atgttacagg cgtgcaaaat ggaagggttt cccctcgtcc cccctcagcc atcagaagac  60
ctggtgccct atgacacgga tctataccaa cgccaaacgc acgagtatta cccctatctc  120
agcagtgatg gggagagcca tagcgaccat tactgggact tccaccccca ccacgtgcac  180
agcgagttcg agagcttcgc cgagaacaac ttcacggagc tccagagcgt gcagcccccg  240
cagctgcagc agctctaccg ccacatggag ctggagcaga tgcacgtcct cgataccccc  300
atggtgccac cccatcccag tcttggccac caggtctcct acctgccccg gatgtgcctc  360
cagtacccat ccctgtcccc agcccagccc agctcagatg aggaggaggg cgagcggcag  420
agcccccccac tggaggtgtc tgacggcgag gcggatggcc tggagcccgg gcctgggctc  480
ctgcctgggg agacaggcag caagaagaag atccgcctgt accagttcct gttggacctg  540
ctccgcagcg gcgacatgaa ggacagcatc tggtgggtgg acaaggacaa gggcaccttc  600
cagttctcgt ccaagcacaa ggaggcgctg gcgcaccgct ggggcatcca gaagggcaac  660
cgcaagaaga tgacctacca gaagatggcg cgcgcgctgc gcaactacgg caagacgggc  720
gaggtcaaga aggtgaagaa gaagctcacc taccagttca gcggcgaagt gctgggccgc  780
gggggcctgg ccgagcggcg ccacccgccc cactga                            816
```

```
SEQ ID NO: 26          moltype = AA  length = 271
FEATURE                Location/Qualifiers
source                 1..271
                       mol_type = protein
                       organism = Homo sapiens
SEQUENCE: 26
MLQACKMEGF PLVPPQPSED LVPYDTDLYQ RQTHEYYPYL SSDGESHSDH YWDFHPHHVH  60
SEFESFAENN FTELQSVQPP QLQQLYRHME LEQMHVLDTP MVPPHPSLGH QVSYLPRMCL  120
QYPSLSPAQP SSDEEEGERQ SPPLEVSDGE ADGLEPGPGL LPGETGSKKK IRLYQFLLDL  180
LRSGDMKDSI WWVDKDKGTF QFSSKHKEAL AHRWGIQKGN RKKMTYQKMA RALRNYGKTG  240
EVKKVKKKLT YQFSGEVLGR GGLAERRHPP H                                 271
```

```
SEQ ID NO: 27          moltype = DNA  length = 828
FEATURE                Location/Qualifiers
source                 1..828
                       mol_type = genomic DNA
                       organism = Homo sapiens
SEQUENCE: 27
atgcccaaag tcttcctggt gaagaggagg agcctggggg tctcggtccg cagctgggat  60
gagctcccgg atgagaaaag ggcagacacc tacatcccag tgggcctagg ccgcctgctc  120
cacgaccccc ccgaggactg ccgcagcgac ggcggcagca gcagcggcag cggcagcagc  180
agcgcggggg agcctggagg agcagagagc agctcgtccc cgcacgcccc cgagagcgaa  240
```

```
acccccgagc ccggcgacgc cgagggcccc gatggacacc tggcgaccaa gcagcgcccg  300
gtcgccagat cgaaaatcaa gttcaccaca ggcacgtgca gcgactcggt ggttcacagc  360
tgtgacctgt gtggcaaggg cttccgtctg cagcgcatgc tgaaccgtca cctcaagtgc  420
cacaaccagg tgaaaagaca cctgtgcacc ttctgcggca agggcttcaa cgacaccttc  480
gacctgaaga ggcacgtccg cacacacaca ggcattcgtc cctacaaatg caacgtctgc  540
aataaagcct tcacccagcg ctgctctctg gagtcccacc tgaagaaaat ccatggggtg  600
cagcagcagt atgcctataa gcagcggcgg gacaagctct acgtctgcga ggattgcggc  660
tacacgggcc ccacccagga ggacctgtac ctgcacgtga acagtgccca tccgggcagc  720
tcgtttctca aaaagacatc taaaaaactg gcagcccttc tgcagggcaa gctgacatcc  780
gcacaccagg agaataccag cctgagtgag gaggaggaga ggaagtga                828

SEQ ID NO: 28           moltype = AA  length = 275
FEATURE                 Location/Qualifiers
source                  1..275
                        mol_type = protein
                        organism = Homo sapiens
SEQUENCE: 28
MPKVFLVKRR SLGVSVRSWD ELPDEKRADT YIPVGLGRLL HDPPEDCRSD GGSSSGSGSS  60
SAGEPGGAES SSSPHAPESE TPEPGDAEGP DGHLATKQRP VARSKIKFTT GTCSDSVVHS  120
CDLCGKGFRL QRMLNRHLKC HNQVKRHLCT FCGKGFNDTF DLKRHVRTHT GIRPYKCNVC  180
NKAFTQRCSL ESHLKKIHGV QQQYAYKQRR DKLYVCEDCG YTGPTQEDLY LHVNSAHPGS  240
SFLKKTSKKL AALLQGKLTS AHQENTSLSE EEERK                               275

SEQ ID NO: 29           moltype = DNA  length = 942
FEATURE                 Location/Qualifiers
source                  1..942
                        mol_type = genomic DNA
                        organism = Homo sapiens
SEQUENCE: 29
atgtacgtga gctacctcct ggacaaggac gtgagcatgt accctagctc cgtgcgccac  60
tctggcggcc tcaacctggc gccgcagaac ttcgtcagcc ccccgcagta cccggactac  120
ggcggttacc acgtggcggc cgcagctgca gcggcagcga acttggacag cgcgcagtcc  180
ccggggccat cctggccggc agcgtatggc gccccactcc gggaggactg gaatggctac  240
gcgcccggag gcgccgcggc cgccgccaac gccgtggctc acggcctcaa cggtggctcc  300
ccggccgcag ccatgggcta cagcagcccc gcagactacc atccgcacca ccacccgcat  360
caccacccgc accacccggc cgccgcgcct tcctgcgctt ctgggctgct gcaaacgctc  420
aaccccggcc ctcctgggcc cgccgccacc gctgccgccg agcagctgtc tcccggcggc  480
cagcggcgga acctgtgcga gtggatgcgg aagccggcgc agcagtccct cggcagccaa  540
gtgaaaacca ggacgaaaga caaatatcga gtggtgtaca cggaccacca gcggctggag  600
ctggagaagg agtttcacta cagtcgctac atcaccatcc ggaggaaagc cgagctagcc  660
gccacgctgg ggctctctga gaggcaggtt aaaatctggt ttcagaaccg cagagcaaag  720
gagaggaaaa tcaacaagaa gaagttgcag cagcaacagc agcagcagcc accacagccg  780
cctccgccgc caccacagcc tccccagcct cagccaggtc ctctgagaag tgtcccagag  840
cccttgagtc cggtgtcttc cctgcaagcc tcagtgcctg gctctgtccc tggggttctg  900
gggccaactg ggggggtgct aaaccccacc gtcacccagt ga                       942

SEQ ID NO: 30           moltype = AA  length = 313
FEATURE                 Location/Qualifiers
source                  1..313
                        mol_type = protein
                        organism = Homo sapiens
SEQUENCE: 30
MYVSYLLDKD VSMYPSSVRH SGGLNLAPQN FVSPPQYPDY GGYHVAAAAA AAANLDSAQS  60
PGPSWPAAYG APLREDWNGY APGGAAAAAN AVAHGLNGGS PAAAMGYSSP ADYHPHHHPH  120
HHPHHPAAAP SCASGLLQTL NPGPPGPAAT AAAEQLSPGG QRRNLCEWMR KPAQQSLGSQ  180
VKTRTKDKYR VVYTDHQRLE LEKEFHYSRY ITIRRKAELA ATLGLSERQV KIWFQNRRAK  240
ERKINKKKLQ QQQQQPPQP PPPPPQPPQP QPGPLRSVPE PLSPVSSLQA SVPGSVPGVL  300
GPTGGVLNPT VTQ                                                       313

SEQ ID NO: 31           moltype = DNA  length = 1038
FEATURE                 Location/Qualifiers
source                  1..1038
                        mol_type = genomic DNA
                        organism = Homo sapiens
SEQUENCE: 31
atgcaacgcc tggtggcctg ggacccagca tgtctccccc tgccgccgcc gccgcctgcc  60
tttaaatcca tggaagtggc caacttctac tacgaggcgg actgcttggc tgctgcgtac  120
ggcggcaagg cggcccccgc ggcgccccccc gcggccagac ccgggccgcg ccccccccgcc  180
ggcgagctgg gcagcatcgg cgaccacgag cgcgccatcg acttcagccc gtacctggag  240
ccgctgggcg cgccgcaggc cccggcgccc gccacggcca cggacacctt cgaggcggct  300
ccgcccgcgc ccgccccccgc gcccgcctcc tccgggcagc accacgactt cctctccgac  360
ctcttctccg acgactacgg gggcaagaac tgcaagaagc cggccgagta cggctacgtg  420
agcctggggc gcctgggggc cgccaagggc gcgctgcacc ccggctgctt cgcgcccctg  480
cacccaccgc ccccgccgcc gccgccgccc gccgagctca aggcggagcc gggcttcgag  540
cccgcggact gcaagcggaa ggaggaggcc ggggcgccgg gcggcggcgc aggcatggcg  600
gcgggcttcc cgtacgcgct gcgcgcttac ctcggctacc aggcggtgcc gagcggcagc  660
agcgggagcc tctccacgtc ctcctcgtcc agcccgcccg gcacgccgag ccccgctgac  720
gccaaggcgc ccccgaccgc ctgctacgcg ggggccgcgc cggcgccctc gcaggtcaag  780
agcaaggcca agaagaccgt ggacaagcac agcgacgagt acaagatccg gcgcgagcgc  840
```

-continued

```
aacaacatcg ccgtgcgcaa gagccgcgac aaggccaaga tgcgcaacct ggagacgcag  900
cacaaggtcc tggagctcac ggccgagaac gagcggctgc agaagaaggt ggagcagctg  960
tcgcgcgagc tcagcaccct gcggaacttg ttcaagcagc tgcccgagcc cctgctcgcc  1020
tcctccggcc actgctag                                                1038

SEQ ID NO: 32          moltype = AA  length = 345
FEATURE                Location/Qualifiers
source                 1..345
                       mol_type = protein
                       organism = Homo sapiens
SEQUENCE: 32
MQRLVAWDPA CLPLPPPPPA FKSMEVANFY YEADCLAAAY GGKAAPAAPP AARPGPRPPA  60
GELGSIGDHE RAIDFSPYLE PLGAPQAPAP ATATDTFEAA PPAPAPAPAS SGQHHDFLSD  120
LFSDDYGGKN CKKPAEYGYV SLGRLGAAKG ALHPGCFAPL HPPPPPPPPP AELKAEPGFE  180
PADCKRKEEA GAPGGGAGMA AGFPYALRAY LGYQAVPSGS SGSLSTSSSS SPPGTPSPAD  240
AKAPPTACYA GAAPAPSQVK SKAKKTVDKH SDEYKIRRER NNIAVRKSRD KAKMRNLETQ  300
HKVLELTAEN ERLQKKVEQL SRELSTLRNL FKQLPEPLLA SSGHC                  345

SEQ ID NO: 33          moltype = DNA  length = 1530
FEATURE                Location/Qualifiers
source                 1..1530
                       mol_type = genomic DNA
                       organism = Homo sapiens
SEQUENCE: 33
atgaatctcc tggacccctt catgaagatg accgacgagc aggagaaggg cctgtccggc  60
gcccccagcc ccaccatgtc cgaggactcc gcgggctcgc cctgcccgtc gggctccggc  120
tcggacaccg agaacacgcg gccccaggag aacacgttcc ccaagggcga gcccgatctg  180
aagaaggaga gcgaggagga caagttcccc gtgtgcatcc gcgaggcggt cagccaggtg  240
ctcaaaggct acgactggac gctggtgccc atgccggtgc gcgtcaacgg ctccagcaag  300
aacaagccgc acgtcaagcg gcccatgaac gccttcatgg tgtgggcgca ggcggcgcgc  360
aggaagctcg cggaccagta cccgcacttg cacaacgccg agctcagcaa gacgctgggc  420
aagctctgga gacttctgaa cgagagcgag aagcggccct tcgtggagga ggcggagcgg  480
ctgcgcgtgc agcacaagaa ggaccacccg gattacaagt accagccgcg gcggaggaag  540
tcggtgaaga acgggcaggc ggaggcagag gaggccacgg agcagacgca catctccccc  600
aacgccatct tcaaggcgct gcaggccgac tcgccacact cctcctccgg catgagcgag  660
gtgcactccc ccggcgagca ctcggggcaa tcccagggcc caccgacccc acccaccacc  720
cccaaaaccg acgtgcagcc gggcaaggct gacctgaagc gagaggggcg cccccttgcca  780
gaggggggca gacagccccc tatcgacttc cgcgacgtgg acatcggcga gctgagcagc  840
gacgtcatct ccaacatcga gaccttcgat gtcaacgagt ttgaccagta cctgccgccc  900
aacggccacc cgggggtgcc ggccacgcac ggccaggtca cctacacggg cagctacggc  960
atcagcagca ccgcggccac cccggcgagc gcgggccacg tgtggatgtc caagcagcag  1020
gcgccgccgc caccccgca gcagccccca caggccccgc cggccccgca ggcgcccccg  1080
cagccgcagg cggcgccccc acagcagccg gcggcacccc cgcagcagcc acaggcgcac  1140
acgctgacca cgctgagcag cgagccgggc cagtcccagc gaacgcacat caagacggag  1200
cagctgagcc ccagccacta cagcgagcag cagcagcact cgccccaaca gatcgcctac  1260
agccccttca acctcccaca ctacagcccc tcctacccgc ccatcacccg ctcacagtac  1320
gactacaccg accaccagaa ctccagctcc tactacagcc acgcggcagg ccagggcacc  1380
ggcctctact ccaccttcac ctacatgaac cccgctcagc gccccatgta cacccccatc  1440
gccgacacct ctggggtccc ttccatcccg cagacccaca gcccccagca ctgggaacaa  1500
cccgtctaca cacagctcac tcgaccttga                                   1530

SEQ ID NO: 34          moltype = AA  length = 509
FEATURE                Location/Qualifiers
source                 1..509
                       mol_type = protein
                       organism = Homo sapiens
SEQUENCE: 34
MNLLDPFMKM TDEQEKGLSG APSPTMSEDS AGSPCPSGSG SDTENTRPQE NTFPKGEPDL  60
KKESEEDKFP VCIREAVSQV LKGYDWTLVP MPVRVNGSSK NKPHVKRPMN AFMVWAQAAR  120
RKLADQYPHL HNAELSKTLG KLWRLLNESE KRPFVEEAER LRVQHKKDHP DYKYQPRRRK  180
SVKNGQAEAE EATEQTHISP NAIFKALQAD SPHSSSGMSE VHSPGEHSGQ SQGPPTPPTT  240
PKTDVQPGKA DLKREGRPLP EGGRQPPIDF RDVDIGELSS DVISNIETFD VNEFDQYLPP  300
NGHPGVPATH GQVTYTGSYG ISSTAATPAS AGHVWMSKQQ APPPPPQQPP QAPPAPQAPP  360
QPQAAPPQQP AAPPQQPQAH TLTTLSSEPG QSQRTHIKTE QLSPSHYSEQ QQHSPQQIAY  420
SPFNLPHYSP SYPPITRSQY DYTDHQNSSS YYSHAAGQGT GLYSTFTYMN PAQRPMYTPI  480
ADTSGVPSIP QTHSPQHWEQ PVYTQLTRP                                    509
```